(12) United States Patent
Graham

(10) Patent No.: US 7,189,561 B2
(45) Date of Patent: Mar. 13, 2007

(54) PRODUCTION OF ADENOVIRUS VECTORS WITH REDUCED LEVELS OF REPLICATION COMPETENT ADENOVIRUS CONTAMINATION

(75) Inventor: Frank L. Graham, Rome (IT)

(73) Assignee: AdVec, Inc., Ancaster (CA)

( * ) Notice: Subject to any disclaimer, the term of this patent is extended or adjusted under 35 U.S.C. 154(b) by 121 days.

(21) Appl. No.: 10/946,484

(22) Filed: Sep. 21, 2004

(65) Prior Publication Data

US 2006/0063259 A1 Mar. 23, 2006

(51) Int. Cl.
| | |
|---|---|
| C12N 15/34 | (2006.01) |
| C12N 15/64 | (2006.01) |
| C12N 15/63 | (2006.01) |
| C12N 5/10 | (2006.01) |
| C12N 15/861 | (2006.01) |
| C07H 21/04 | (2006.01) |

(52) U.S. Cl. ............... 435/320.1; 435/91.4; 435/455; 435/456; 435/366; 536/23.72; 424/93.2

(58) Field of Classification Search ............. None
See application file for complete search history.

(56) References Cited

U.S. PATENT DOCUMENTS

| 5,880,102 A * | 3/1999 | George et al. ............. 514/44 |
| 6,265,212 B1 * | 7/2001 | Fallaux et al. ........... 435/320.1 |
| 6,692,966 B2 | 2/2004 | Fallaux et al. |

OTHER PUBLICATIONS

Ng, P. et al. "Cre Levels Limit Packaging Signal Excision Efficiency in the Cre/loxP Helper-Dependent Adenoviral Vector System", 2002, J. Virol., vol. 76: pp. 4181-4189.*

Parks, R. et al., "A helper-dependent adenovirus vector system: Removal of helper virus by Cre-mediated excision of the viral packaging signal", 1996, PNAS, vol. 93: pp. 13565-13570.*

Palmer, Donna et al., *Improved System for Helper-Dependent Adenoviral Vector Production*, Molecular Therapy, vol. 8, No. 5, Nov. 2003, pp. 846-852.

Hearing, Patrick, et al., *Identification of a Repeated Sequence Element Required for Efficient Encapsidation of the Adenovirus Type 5 Chromosome*, Journal of Virology, vol. 61, No. 8, Aug. 1987, pp. 2555-2558.

Suzuki, Erika et al., *A Simple Method for the Simultaneous Detection of E1A and E1B in Adenovirus Stocks*, Oncology Reports 11, 2004, pp. 173-178.

Soudais, Claire, *Characterization of cis-Acting Sequences Involved in Canine Adenovirus Packaging*, Molecular Therapy, vol. 3, No. 4, Apr. 2001, pp. 631-640.

Schmid, Susanne I. Et al., *Cellular Components Interact with Adenovirus Type 5 Minimal DNA Packaging Domains*, Journal of Virology, vol. 72, No. 8, Aug. 1998, pp. 6339-6347.

Sandig, Volker et al., *Optimization of the Helper-Dependent Adenovirus System for Production and Potency in Vivo*, PNAS, vol. 97, No. 3, Feb. 2000, pp. 1002-1007.

* cited by examiner

*Primary Examiner*—Scott D. Priebe
*Assistant Examiner*—Michael Burkhart
(74) *Attorney, Agent, or Firm*—Joseph Fischer; Beusse, Wolter, Sanks, Mora & Maire, P.A.

(57) ABSTRACT

Methods, cells and recombinant adenoviral vectors are disclosed that permit the production of recombinant adenoviral vector stocks with reduced levels of contamination by replication competent adenoviruses (RCA). In certain embodiments are disclosed early region 1 (E1) deficient recombinant adenoviral vectors and complementing E1 positive host cells whose sequences are designed to avoid formation of RCA by homologous recombination between sequences in the vector and E1 sequences in the cells. One aspect of the invention involves the inversion of the packaging signal in a recombinant adenoviral vector relative to an adjacent or nearby inverted terminal repeat (ITR). Methods include use of site-specific intregrase family recombinases such as Cre or FLP and recombinase recognition sites such as lox sites or frt sites.

12 Claims, 36 Drawing Sheets

SEQ ID NO:1: oligo a: 5'CCCGAATTCTAGTAGTGTGGCGGAAGTGTG 3'

SEQ ID NO:2: oligo b: 5'GTCACAGCTATCCGTACT 3'

Construction of pUCITRPack2

Cut with MseI, Klenow, cut with EcoRI
purify 480 bp fragment containing
packaging signal and ITR junction,
clone into EcoRI SmaI site of pUC19

Construction of pFG190D1, D2, D3, D4

Delete from EagI to StuI (D1) or AccI (D2) or HindIII(D3) or to SmaI (D4)

Predicted structure for RCA generated as illustrated in Figure 5

Numbers in brackets represent HindIII sites

Oligonucleotides used as primers for Strategy I PCR

```
SEQ ID NO:3:  5' CC TCCGGA CTTCCGCCAC ACTAGT ACGTCACC 3'           (primer 1)

SEQ ID NO:4:  5' CC TCCGGA ACGCGT CATTAGGGACTTTCCAATGGG 3'         (primer 2)

SEQ ID NO:5:  5' CC ACGCGT GGCGGAAGTGTGATGTTGCAAG 3'               (primer 3)

SEQ ID NO:6:  5' CC ACTAGT ATAATAAAACGCCAACTTTGACCC 3'             (primer 4)
```

Spe I sites are indicated in bold, and Mlu I sites are underlined

Figure 10B

Cotransfection of 293 cells with pBHGloxΔE1,3Cre and pDCMH4loxPkgnginv to generate a vector with an inverted packaging signal

Oligonucleotides used for PCR in Strategy II

5' atatTAATGAGGGGGTGGAGTTTGTGACGTGGCGCGGGGCGTGGGAA
CGGGGCGGGTGACGTAGgctagCCGCCTATAATAAACGCCAAC 3'

SEQ ID NO:7,
Oligo 7 (the portion indicated in bold) anneals to the sequence from nts 457 to 433 in pMRK and primes leftward. The 60 nts that are capitalized but not in bold are homologous to nts 47 to 106 in pMRK Underlined sequences (atTAAT and gctagC) represent Ase I and Nhe I sites respectively.

5' cgccCATGGCGGTAATGTTTGGACATGAGCCAATATAAATGTACATAT
TATGATATGGATACAACGTcctaggTAGTGTGGGCGGAAGTGTGATGTTG 3'

SEQ ID NO:8,
Oligo 8 (the portion indicated in bold) anneals to the sequence from nts 107 to 130 in pMRK and primes rightward. The 62 nts that are capitalized but not in bold are homologous to nts 535 to 474 in pMRK Underlined sequences (cCATGG and cctagg) represent Nco I and Avr II sites respectively.

Figure 12C

Packaging signal inversion. Strategy III, step 1.

Packaging signal inversion. Strategy III, step 4.

Oligonucleotides used for PCR in Strategy III

5' tacaatcaagctt att gctagc CTACGTCACCCGCCCCGTTCCC 3'

SEQ ID NO:9,
Oligo 9 (portion shown in uppercase) anneals to the sequence from nts 106 to 85 in pMRK and primes leftward. The underlined nts represent a Hind III site and nts in bold indicate a Nhe I site 5' tcactgaaagctt cctagg CCATTGCATACGTTGTATCCATATC 3'

SEQ ID NO:10,
Oligo 10 (portion indicated in uppercase) anneals to the sequence from nts 465 to 489 in pMRK and primes rightward. The underlined nts represent a Hind III site and nts in bold indicate an Avr II site.

Figure 13F

SEQUENCE LISTING

```
<160> NUMBER OF SEQ ID NOS: 10

<210> SEQ ID NO 1
<211> LENGTH: 30
<212> TYPE: DNA
<213> ORGANISM: ARTIFICIAL SEQUENCE
<220> FEATURE:
<223> OTHER INFORMATION: PRIMER

<400> SEQUENCE: 1
cccgaattct agtagtgtgg cggaagtgtg                                    30

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: PRIMER

<400> SEQUENCE: 2
gtcacagcta tccgtact                                                 18

<210> SEQ ID NO 3
<211> LENGTH: 32
<212> TYPE: DNA
<213> ORGANISM: ARTIFICIAL SEQUENCE
<220> FEATURE:
<223> OTHER INFORMATION: PRIMER
```

<400> SEQUENCE: 3
cctccggact tccgccacac tagtacgtca cc                     32

<210> SEQ ID NO 4
<211> LENGTH: 35
<212> TYPE: DNA
<213> ORGANISM: ARTIFICIAL SEQUENCE
<220> FEATURE:
<223> OTHER INFORMATION: PRIMER

<400> SEQUENCE: 4
cctccggaac gcgtcattag ggactttcca atggg                  35

<210> SEQ ID NO 5
<211> LENGTH: 30
<212> TYPE: DNA
<213> ORGANISM: ARTIFICIAL SEQUENCE
<220> FEATURE:
<223> OTHER INFORMATION: PRIMER

<400> SEQUENCE: 5
ccacgcgtgg cggaagtgtg atgttgcaag                        30

<210> SEQ ID NO 6
<211> LENGTH: 32
<212> TYPE: DNA
<213> ORGANISM: ARTIFICIAL SEQUENCE
<220> FEATURE:
<223> OTHER INFORMATION: PRIMER

<400> SEQUENCE: 6
ccactagtat aataaaacgc caactttgac cc                     32

<210> SEQ ID NO 7
<211> LENGTH: 25
<212> TYPE: DNA
<213> ORGANISM: ARTIFICIAL SEQUENCE
<220> FEATURE:
<223> OTHER INFORMATION: PRIMER

<400> SEQUENCE: 7
ccgcctataa aataaaacg ccaac                              25

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: PRIMER

<400> SEQUENCE: 8
tagtgtggcg gaagtgtgat gttg                              24

<210> SEQ ID NO 9
<211> LENGTH: 22
<212> TYPE: DNA
<213> ORGANISM: ARTIFICIAL SEQUENCE
<220> FEATURE:
<223> OTHER INFORMATION: PRIMER

<400> SEQUENCE: 9
ctacgtcacc cgccccgttc cc                                22

<210> SEQ ID NO 10

```
-continued
<211> LENGTH: 25
<212> TYPE: DNA
<213> ORGANISM: ARTIFICIAL SEQUENCE
<220> FEATURE:
<223> OTHER INFORMATION: PRIMER

<400> SEQUENCE: 10
ccattgcata cgttgtatcc atatc                                              25
```

PRODUCTION OF ADENOVIRUS VECTORS WITH REDUCED LEVELS OF REPLICATION COMPETENT ADENOVIRUS CONTAMINATION

REFERENCE TO SEQUENCE LISTING ON COMPACT DISC

A compact disc containing a file named "10524-005" that contains the computer readable form of the sequence listing of the ten sequences disclosed herein is hereby incorporated by reference. The information recorded in the computer readable form is identical to the written (paper) sequence listing provided with this specification.

BACKGROUND OF THE INVENTION

1. Field of the Invention

This invention relates to the field of recombinant technology of viruses and to production of recombinant viral vectors, and is particularly related to production of recombinant adenoviral vectors with reduced levels of contamination by replication competent adenoviruses (RCA).

2. Background of the Invention

As taught in WO95/00655, adenoviruses (Ads) in the form of recombinant adenoviral vectors can be used as mammalian cell expression vectors, with excellent potential as live recombinant viral vaccines, as transducing vectors for gene therapy, for research, and for production of proteins in mammalian cells (see Hitt, M., Addison, C. and Graham, F. L Human adenovirus vectors for gene transfer into mammalian cells. In: "Advances in Pharmacology—Gene Therapy" Ed. J. Thomas August, Academic Press. San Diego, Calif. 40: 137–206, 1997 for review). General uses for recombinant adenoviral vectors also include use in functional genomics research, protein over-expression, preclinical studies and clinical trials.

In the human Ad genome, early region 1 (E1), E3, and a site upstream of E4 have been utilized as sites for introducing foreign DNA sequences to generate adenovirus recombinants. In the absence of compensating deletions in E1 or E3, a maximum of about 2 kb can be inserted into the Ad genome to generate viable virus progeny (Bett, A. J., Prevec, L., and Graham, F. L. Packaging capacity and stability of human adenovirus type 5 vectors. J. Virol. 67: 5911–5921, 1993.). The E1 region is not required for viral replication in complementing 293 cells (Graham, F. L., Smiley, J., Russell, W. C., and Nairn, R. Characteristics of a human cell line transformed by DNA from human adenovirus type 5. J. Gen. Virol. 36, 59–72, 1977.), or other cells known to complement E1, and up to approximately 3.2 kb can be deleted in this region to generate vectors with a capacity of 5.0–5.2 kb. Besides expanding the capacity of the vector to permit insertion of larger amounts of foreign DNA, deletion of E1 results in a defective Ad which is essentially unable to replicate in normal cells and thus provides a measure of safety as well as increased utility for many applications employing these vectors. In the E3 region, which is not required for viral replication in cultured cells, deletions of various sizes have been utilized to generate nonconditional helper independent vectors with a capacity of up to 4.5–4.7 kb. The combination of deletions in E1 and E3 permits the construction and propagation of adenovirus vectors with a capacity for insertions of up to approximately 8 kb of foreign DNA.

Recombinant adenoviral vectors with foreign DNA inserted in place of E1 sequences, and optionally also carrying deletions of E3 sequences, are conventionally known as "first generation" (FG) recombinant adenoviral vectors. FG vectors are of proven utility for many applications. They can be used as research tools for high-efficiency transfer and expression of foreign genes in mammalian cells derived from many tissues and from many species. First generation vectors can be used in development of recombinant viral vaccines when the vectors contain and express antigens derived from pathogenic organisms. Importantly, Recombinant adenoviral vectors have become extensively used for human gene therapy, because of their ability to efficiently transfer and express foreign genes in vivo, and due to their ability to transduce both replicating and non-replicating cells in many different tissues. Adenovirus vectors are widely used in these applications, as well as other applications disclosed herein and in the references cited herein. The biology and applications for adenoviruses is described in Adenoviral Vectors for Gene Therapy, David T. Curiel and Joanne T. Douglas, Academic Press, 2002 (and in particular Chapters 3, 4, 5, 6, 15 and 16).

The construction of recombinant adenoviral vectors can be performed in many ways (reviewed by Ng, P. and Graham, F. L. Construction of first generation adenoviral vectors. In: Methods in Molecular Medicine. Gene Therapy Protocols, $2^{nd}$ edition. Jeffrey R. Morgan (Ed). Humana Press Inc. Totawa, N.J. Vol. 69, pp. 389–414, 2002 and by Hitt, M., Bett, A. J., Prevec, L. and Graham, F. L Construction and propagation of human adenovirus vectors. In: "Cell Biology: A Laboratory Handbook" Ed. J. E. Celis. Academic Press. 2nd Edition, Vol. 1, pp 500–512, 1998.) The most popular methods for isolation make use of recombination between a small shuttle plasmid containing sequences from the left end of the viral genome and typically comprising an insert of foreign DNA and a genomic plasmid that comprises the remainder of the viral genome. Recombination in cotransfected E1+ host cells such as 293 cells results in formation of the desired FG vector. (See Bett, A. J., Haddara, W., Prevec, L. and Graham, F. L An efficient and flexible system for construction of adenovirus vectors with insertions or deletions in early regions 1 and 3. Proc. Natl. Acad. Sci. US 91: 8802–8806, 1994. and U.S. Pat. No. 6,140,087 for details). An improvement in this system was made by utilizing site specific recombinases such as Cre or FLP acting on loxP and frt target sites respectively to induce recombination between the shuttle plasmid and the genomic plasmid. Example of such systems are described in Ng, P., Parks, R. J., Cummings, D. T., Evelegh, C. M., Sankar, U. and Graham, F. L. An enhanced system for construction of adenoviral vectors by the two-plasmid rescue method. Human Gene Therapy 11: 693–699, 2000; Ng, P., Cummings, D. T., Evelegh, C. M. and Graham, F. L. The yeast recombinase FLP functions effectively in human cells for construction of adenovirus vectors. BioTechniques 29: 524–528, 2000; Ng, P. and Graham, F. L. Adenoviral Vector Construction I: Mammalian Systems In: Adenoviral Vectors for Gene Therapy. D. T. Curiel & J. T. Douglas (Eds) Academic Press, NY. 2002, pp 71–104. Site-specific recombination catalyzed by an efficient recombinase, such as the Cre or FLP recombinase, can be many-fold more efficient than homologous recombination. This methodology is also applicable to insertion of foreign DNA sequences into various regions of the viral DNA in addition to, or instead of, the E1 region classically used for that purpose.

Another popular method for construction of Recombinant adenoviral vectors makes use of homologous recombination in bacteria to substitute viral DNA sequences with foreign DNA (C. Chartier, Degryse, E; Gantzer, M; Dieterle, A;

Pavirani, A; Mehtali, M Efficient generation of recombinant adenovirus vectors by homologous recombination in *Escherichia coli*. J. Virol. 70 (1996), pp. 4805–4810.). The use of homologous recombination in bacteria is also applicable to insertion of foreign DNA sequences into various regions of the viral DNA, in addition to the E1.

A typical first generation recombinant adenoviral vector is illustrated in FIG. 1. It has a deletion of the E1A and E1B gene sequences of the Early Region I and a substitution of those E1 sequences with foreign DNA usually comprising a promoter, a cDNA, and a polyadenylation signal together comprising an expression cassette. Because E1 encoded functions are necessary for replication of adenoviruses FG vectors must be propagated in mammalian cells that contain and express E1 functions. The cell line most commonly used for this purpose is the 293 cell line (Graham, F. L., Smiley, J., Russell, W. C., and Nairn, R. Characteristics of a human cell line transformed by DNA from human adenovirus type 5. J. Gen. Virol. 36, 59–72, 1977.) which contains adenovirus type 5 ("Ad5") sequences extending from nucleotide ("nt") 1 to nt 4344 integrated into chromosome 19 (19q13.2) (Louis, N., Evelegh, C. and Graham, F. L. Cloning and sequencing of the cellular/viral junctions from the human adenovirus type 5 transformed 293 cell line. Virology, 233:423–429, 1997.) The deletion of E1 sequences from FG vectors usually does not encompass the ITR from nt 1 to about nt 103 nor the viral DNA packaging signal from about nt 190 to about 380 nor the coding sequences for protein IX because the ITR and packaging signal are required in cis for viral DNA replication and packaging of the vector DNA into virion capsids, respectively, and the pIX protein is a required capsid component of the virion.

The requirement for pIX coding sequences is interesting for a number of reasons. Firstly the protein was originally thought to be dispensable for virus production because viruses with deletions of E1 that included the pIX gene were viable (though the virions produced were more heat labile than wt virions) (Colby, W. W., and Shenk, T. (1981). Adenovirus type 5 virions can be assembled in vivo in the absence of detectable polypeptide IX. *J. Virol.* 39, 977–980.). However it was subsequently shown that pIX is essential for efficient packaging of full length viral genomes into functional virions (Ghosh-Choudhury, G., Haj-Ahmad, Y., and Graham, F. L. (1987), Protein IX, a minor component of the human adenovirus capsid, is essential for the packaging of full length genomes. *EMBO J.* 6, 1733–1739, Sargent, K. L., Ng., P., Graham, F. L. and Parks, R. J. Development of a size-restricted pIX-deleted helper virus for amplification of helper-dependent adenovirus vectors. Gene Ther. 11: 504–511, 2004.) Although 293 cells contain the pIX coding sequences the gene is not expressed in 293 cells, hence the need to include the pIX gene in the Ad vector genome for virion stability and for efficient packaging of full length virion DNA.

A major problem in the production of FG recombinant adenoviral vectors in 293 cells and many other E1 complementing host cells is the appearance of replication competent adenoviruses (RCA) as contaminants of the vector stock (Lochmuller, H., Jani, A., Huard, J., Prescott, S., Simoneau, M., Massie, B., Karpati, G., and Acsadi, G. (1994): Emergence of early region 1-containing replication-competent adenovirus in stocks of replication-defective adenovirus recombinants (ΔE1-ΔE3) during multiple passages in 293 cells. Hum. Gene Ther. 5, 1485–1492.) RCA appear as a result of recombination between vector DNA sequences and homologous sequences in the host cells as discussed below. For many applications the presence of RCA in vector stocks is a significant problem (discussed by Fallaux, F. J., van der Eb, A. J. and Hoeben, R. C. Who's afraid of replication-competent adenoviruses? Gene Ther. 6: 709–712, 1999) and numerous attempts have been made to solve this problem by modifying the vectors, the complementing host cells, or both.

The structure of Ad5 sequences integrated in the 293 cellular genome is illustrated in FIG. 1. As mentioned above, the viral sequences comprise an uninterrupted segment of Ad5 extending from the first nt of the Ad5 genome to nt 4344 and contain therefore, an intact left ITR, the complete packaging signal and a complete E1 region composed of E1A and E1B. Also contained in the cell are the coding sequences for pIX and part of the leftward-transcribed IVa2 gene. Indicated immediately above the Ad5 sequences is a typical E1 deletion used in FG vectors to eliminate E1 and to allow for substitution of foreign DNA. Numerous similar FG vectors have been constructed and described in which the end points of the deletions may vary but generally the deletions cannot extend significantly further left or right of those end points shown in FIG. 1 without compromising the ability of the vector to replicate. It can be seen that there is significant overlap of homologous sequences between the resulting FG vector DNA and the Ad5 DNA of 293 cells on either side of the deletion. Without being bound to a particular theory, recombination event(s) along these regions of homologous sequences is/are believed to be the reason for occurrence of RCA. Because 293 cells contain an intact left ITR as well as the packaging signal it is theoretically possible to generate an E1+virus by a single recombination event involving the sequences to the right of the E1 deletion, thus joining the vector DNA to the E1 sequences of 293 cells. However, Hehir et al. have demonstrated that RCA can occur, and indeed more frequently (perhaps always) do occur as a result of two recombination events, one on each side of the E1 region (Hehir, K. M., Armentano, D., Cardoza, L. M., Choquette, T. L., Berthelette, P. B., White, G. A., Couture, L. A., Everton, M. B., Keegan, J., Martin, J. M., Pratt, D. A., Smith, M. P., Smith, A. E. and Wadsworth, S. C. (1996). Molecular characterization of replication-competent variants of adenovirus vectors and genomic modifications to prevent their occurrence. J. Virol. 70,8459–8467.). This implies that the presence of an intact ITR in the complementing cells is not necessary for generation of RCA provided sufficient overlap is present on each side of the E1 deletion.

Hehir et al. attempted to reduce the frequency of RCA generation during growth of Ad vectors in 293 cells by modifying the design of their vectors. In one strategy they deleted or rearranged the coding sequences for the pIX protein that are at the 3' end of E1 and effectively extended the E1 deletion to nt 4020. This strategy was followed to reduce the degree of overlap between Ad sequences in 293 cells and the sequences to the right of E1 in the vector and thereby, per their theory, reduce the efficiency of recombination and the consequent formation of RCA. In fact, as was subsequently shown in the inventor's laboratory, the Ad5 sequences integrated in the genome of 293 cells extend considerably beyond the pIX gene to nt 4344 implying overlap to the extent of about 320 bp. Consequently removal of the pIX gene would not be expected to prevent absolutely the occurrence of RCA. Hehir et al. claimed that although RCA contamination was reduced, it was not absolutely eliminated.

Other approaches to reduce the frequency of RCA contamination have involved modifications not to the vectors but to the viral DNA sequences used to establish E1+complementing host cells. Thus, for example, Imler et al. (Imler, J. L., Chartier, C., Dieterle, A., Sainte-Marie, M., Faure, T., Pavirani, A. and Metali, M. Novel complementation cell lines derived from human lung carcinoma A549 cells support the growth of E1-deleted adenovirus vectors. Gene Ther. 3: 75–84, 1996) developed complementing cell lines that lacked the left ITR and packaging signal of the Ad5 genome and in which E1A expression was regulated by heterologous promoters. They included the pIX gene in the plasmids used to transform A549 cells but observed that pIX was not efficiently expressed in any of the transformed clones as is also the case in 293 cells. Their vectors retained the left ITR and the packaging signal and had an insertion of foreign DNA substituting for E1 coding sequences. The vectors had a deletion of E1 sequences extending from nt 459 to at least Ad5 nt 3510 whereas the complementing cells had Ad sequences extending from nt 505 to nt 3510. Consequently the vectors and cell lines had no homology at the extreme left end or right end of E1, i.e., to the left or right of the foreign DNA insert. This was predicted to prevent or reduce the efficiency of RCA generation though they did not present any experimental data bearing on this. Unfortunately the host cells only complemented E1 deleted vectors about ¹⁄₁₀ as well as did 293 cells. A somewhat similar strategy was described by Brough and Kovesdi (U.S. patent application 2003/0040100) who established A549 cells transformed with an expression cassette comprising adenovirus type 2 ("Ad2") sequences from nts 362 to 5708 with the E1A promoter enhancer replaced by the HCMV IE gene promoter. Again, the cells were expected to support replication of an Ad vector (with an E1 deletion of nts 356 to 3328) without generation of RCA by virtue of the fact that there is no overlap left of E1 and consequently no possibility of homologous recombination events capable of generating RCA. Another approach was adopted by Fallaux et al (Fallaux, F. J., Bout, A., van der Velde, I., van der Wollenberg, D. J., Hehir, K. M., Keegan, J., Auger, C., Cramer, S. J., van Ormondt, H., van der Eb, A. J., Valerio, D., and Hoeben, R. C. New helper cells and matched early region 1-deleted adenovirus vectors prevent generation of replication-competent adenoviruses. Hum. Gene Ther. 9: 1909–1917, 1998, and see also U.S. Pat. Nos. 6,670,188; 6,692,966; 6,602,706; 6,306,652; 6,265,212). Fallaux et al. developed cell lines transformed by plasmids comprising Ad5 nts 459–3510 expressed under the control of the human phosphoglycerate kinase (PGK) promoter and used the resulting complementing E1+cells, typified by the PER.C6 line, for growth of "matched" E1 deleted Ad vectors that had no homology whatsoever with the viral sequences in PER.C6 cells, either to left or to right of the E1 deletion. They reported that matching the host cells and the vectors in this way solved the RCA problem. Unfortunately, unlike 293 cells, PER.C6 cells are not readily available and are expensive to obtain. Consequently it would be most valuable if alternate approaches could be developed, especially systems that permit the use of 293 cells. See for example Davidson et al (U.S. patent application 2002/0098571, page 3, paragraph 0023) who pointed out "This (ability to use standard 293 cells) is important since most investigators do not have access to alternative cell lines, or cannot justify the cost of their use."

The investigators whose work is outlined above did not consider modifying the packaging signal of the vector as a possible approach to solving the RCA problem but instead focused on modifying the left end viral DNA sequences in the complementing host cells, essentially eliminating the ITR and packaging signal (which overlaps with the E1A enhancer promoter) and substituting these viral control elements with a heterologous promoter such as the PGK promoter or the HCMV IE promoter. One group, however, has made certain recombinant virus constructs comprising an inverted packaging signal (Palmer, D and Ng, P. Improved system for helper-dependent adenoviral vector production. Molec. Ther. 8: 846–852, 2003). They constructed a helper virus for amplification of helper dependent vectors in the system described in U.S. Pat. No. 5,919,676 wherein the packaging signal of the helper was inverted with respect to the packaging signal of the helper dependent vector. The purpose of this modification was to avoid recombination between the left end sequences of the helper dependent vector and helper that would effectively remove a loxP site from the helper virus DNA and render it resistant to the effects of Cre recombinase whose action is otherwise needed to excise the packaging signal of the helper virus to prevent packaging of helper virus DNA into virions. Palmer and Ng also made another modification in the helper, inserting a non-coding DNA stuffer into the E3 region. The stated purpose of adding the stuffer sequence was to render any recombinants comprising this part of the helper DNA too large to package into RCA. (See Parks, R. J., Chen, L., Anton, M., Sankar, U., Rudnicki, M. A. and Graham, F. L. A new helper-dependent adenovirus vector system: removal of helper virus by Cre-mediated excision of the viral packaging signal. Proc. Natl. Acad. Sci. U.S. 93: 13565–13570, 1996.)

Despite varied and dedicated research efforts by a number of research groups to effectively and efficiently reduce RCA generation in the propagation of first generation recombinant adenoviral vectors, there exists a need to identify and utilize systems, methods and compositions that provide for the reduction or elimination of RCA during such propagation. The present invention addresses this need.

BRIEF DESCRIPTION OF DRAWINGS

In FIG. 3A is shown construction of a plasmid, pZW17, that contains Ad5 sequences from nt 101 to nt 4064. Plasmid pXC1 (Microbix Biosystems) was digested with BsaBI which cuts twice as shown and the digestion product was ligated to create pZW16. In the next step a PCR product made off pXC1 (using oligonucleotides a (SEQ ID NO: 1) and b (SEQ ID NO: 2) shown below) was digested with EcoRI and XbaI and inserted into the EcoRI-XbaI sites of pZW16 to generate pZW17. This plasmid was used to transform primary human cells (primary human embryo retinal cells or primary human embryo kidney cells) to produce transformed Ad E1 expressing cell lines, such as HER224 cells, capable of complementing growth of FG vectors.

In FIG. 3B is illustrated the fact that the problem of RCA formation has not been eliminated by reducing the amount of overlap. Also shown is the likely mechanism by which RCA is still generated, and, bottom, a second possible means to solve the RCA problem by moving the packaging signal to the right end of the vector genome, thereby eliminating overlap on the left of the foreign DNA insert, when the vector is propagated in HER224 cells. Note that in this strategy the packaging signal has the wt orientation with respect to the adjacent (right) ITR. Because there is no homology at the extreme left end of the virus between the vector backbone and the HER224 viral sequences it was expected that this strategy would eliminate the second recombination event between sequences leftward of E1.

The first step (FIG. 4A) involved removal of terminal sequences from the viral DNA by digestion with Exonuclease III and S1 nuclease (Graham, F. L., van der Eb, A. J., and Heijneker, J. L. Size and location of the transforming region in human adenovirus type 5 DNA. Nature 251, 687–691, 1974.) After treatment with ExoIII-S1 the right terminal XbaI fragment of the viral DNA was cloned into the XbaI-StuI site of pDC512 (Microbix Biosystems). Controlled digestion and subsequent screening by sequencing resulted in isolation of one plasmid containing the desired structure, namely the right end of the Ad5 DNA minus the terminal 131 bp including the right ITR. This plasmid, designated pDC512AdXbaC, was then digested with AatII and XbaI and religated after treatment to make blunt ends resulting in pDC512AdXbaCDel.

Figure 4A:
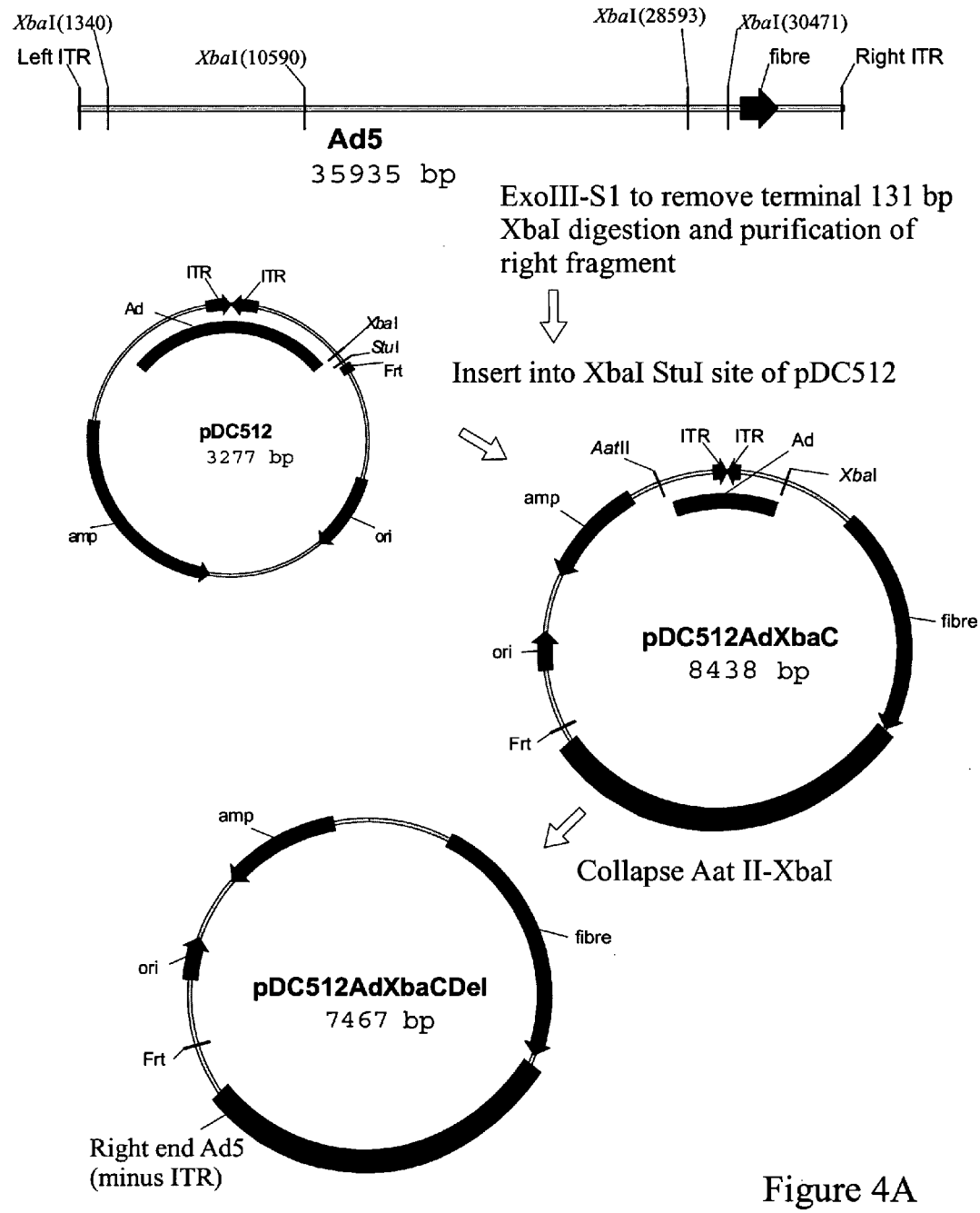
FIGS. 4A–H illustrate the strategy used to generate a series of vectors containing a foreign DNA (LacZ) expression cassette at the left end of the genome and having a packaging signal at the right end of the genome. The resulting vector (e.g. AdFG190LacZ) has no overlap at the extreme left end with viral sequences in HER224 cells.
Figure 4B:
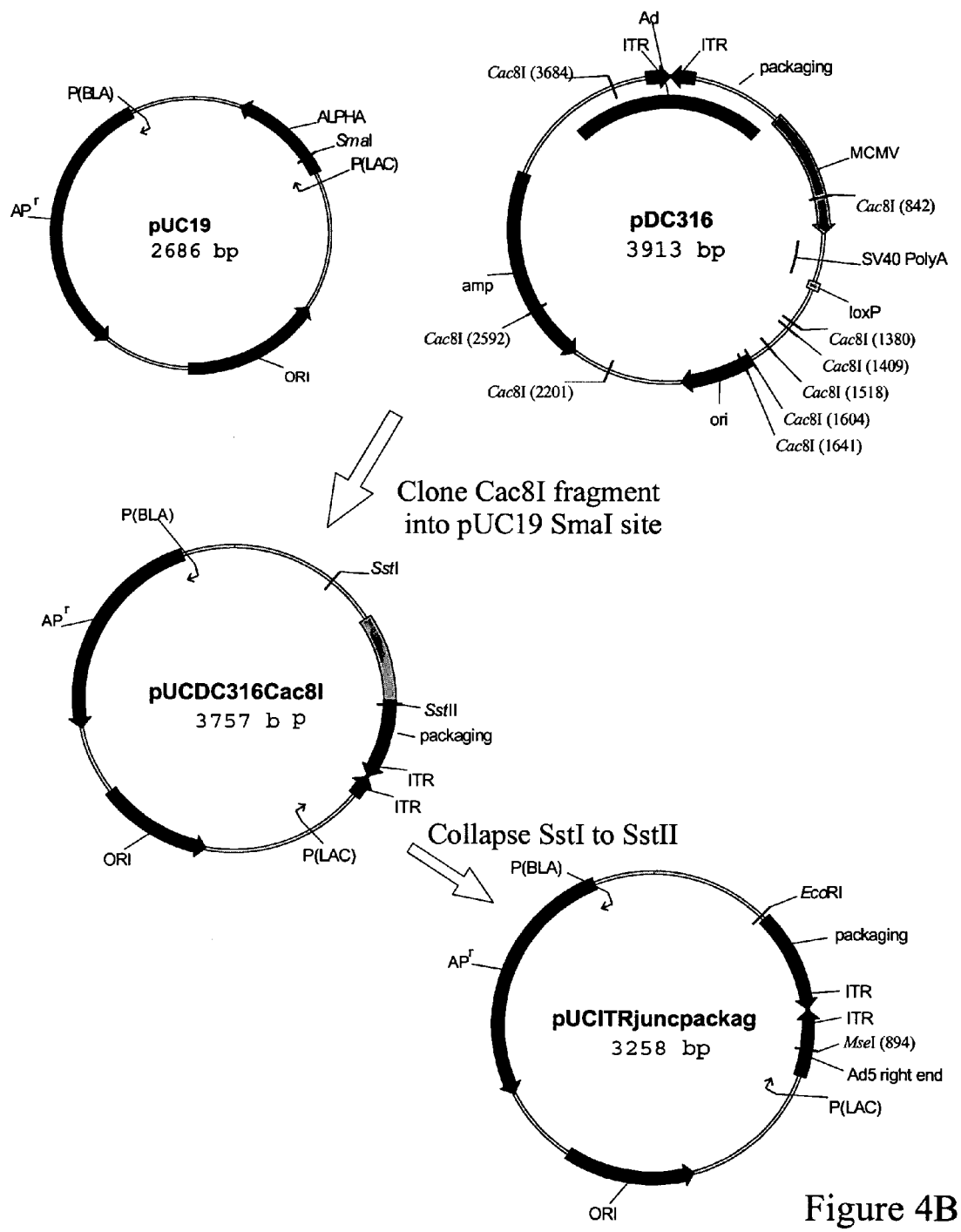

FIG. 4B illustrates construction of another intermediate plasmid, pUCITRjuncpackag. This was constructed by cloning a Cac8I fragment containing the ITR junction from pDC316 (Microbix Biosystems) into the Sma I site of pUC19. The resulting plasmid, pUCDC316Cac8I was then collapsed using SstI and SstII digestion and ligation to generate pUCITRjuncpackag.

Figure 4C:
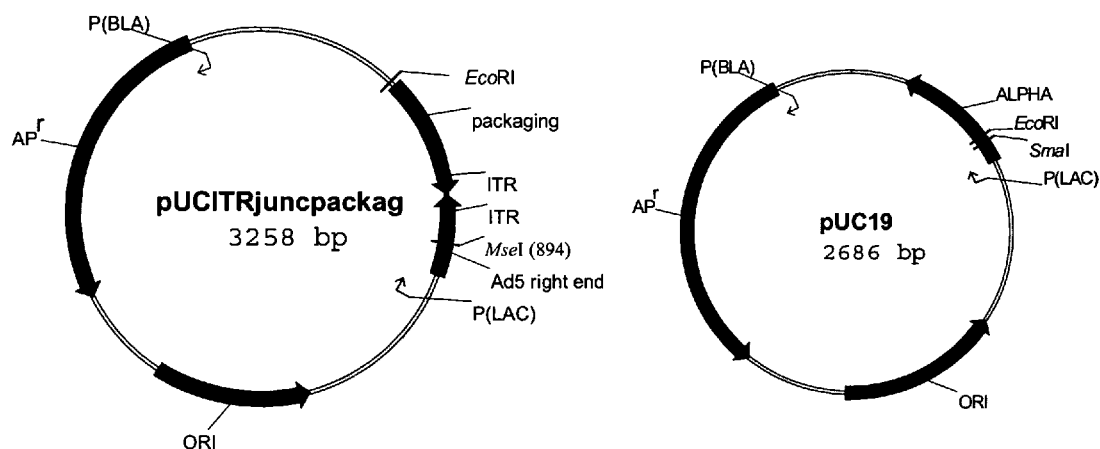
Figure 4C:
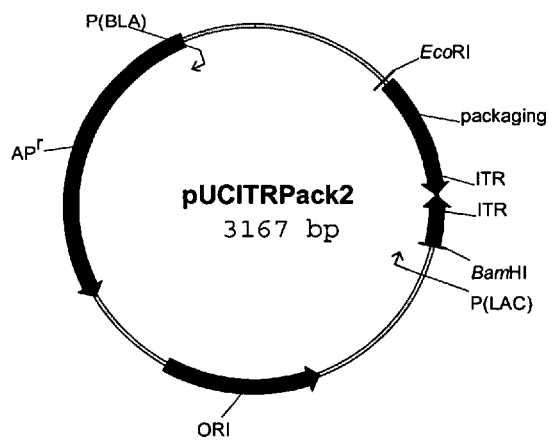

FIG. 4C illustrates how pUCITRPack2 was made by transferring a 480 bp EcoRI to MseI fragment from pUCITRjuncpackag into the SmaI site of pUC19. PUCITRPack2 contains the packaging signal of Ad5 and an ITR junction flanked by EcoRI and BamHI sites.

Figure 4D:
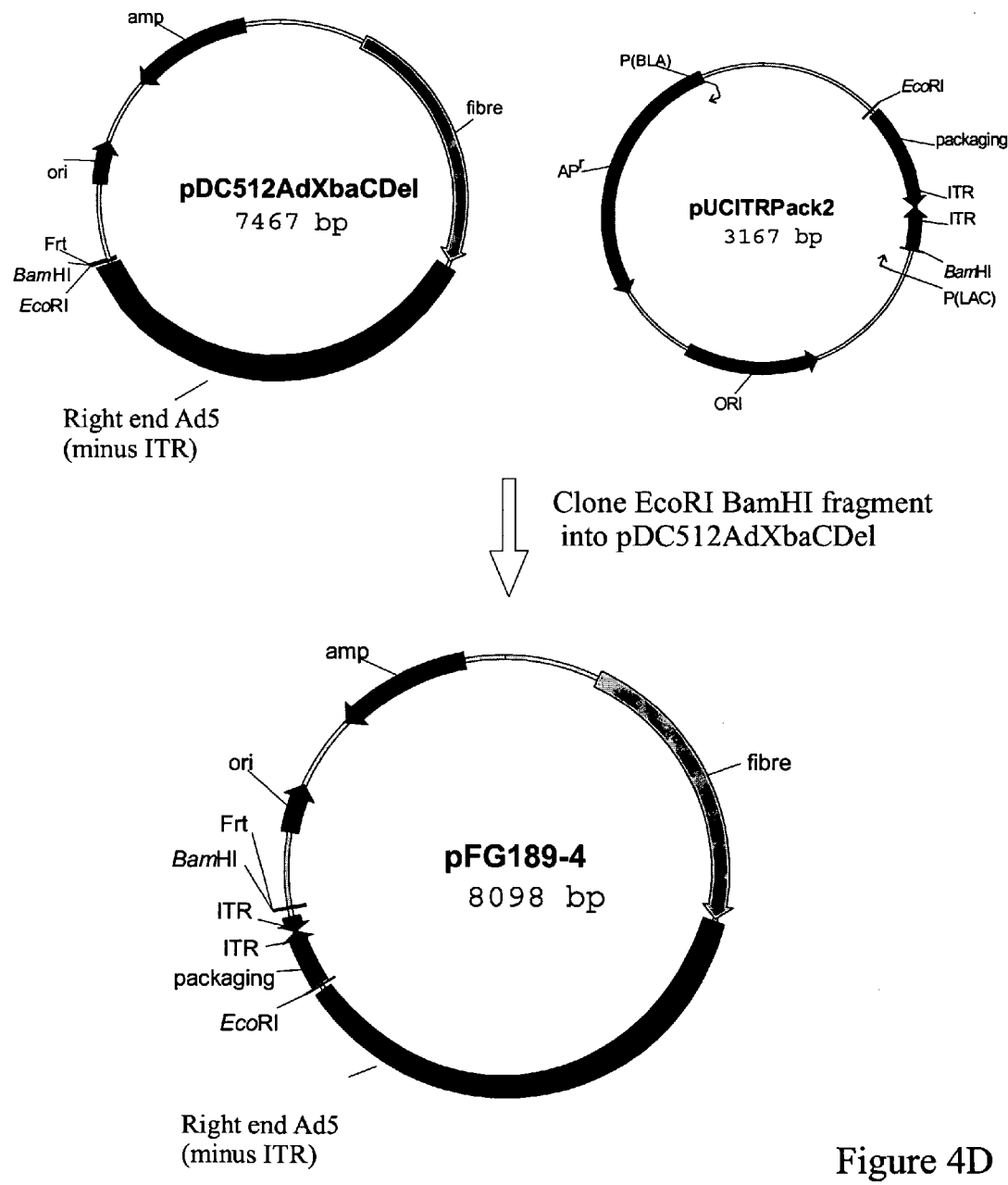

FIG. 4D shows the insertion of the DNA fragment containing the packaging signal of Ad5 and ITR junction from pUCITRPack2 into the EcoRI-BamHI site of pDC512AdXbaCDel to create pFG189-4. The properties of this plasmid are as follows: it contains the right end of Ad5 DNA minus 131 nt of right terminal DNA, then the packaging signal and an ITR junction and finally a frt site (the target for the site specific recombinase, FLP).

Figure 4E:
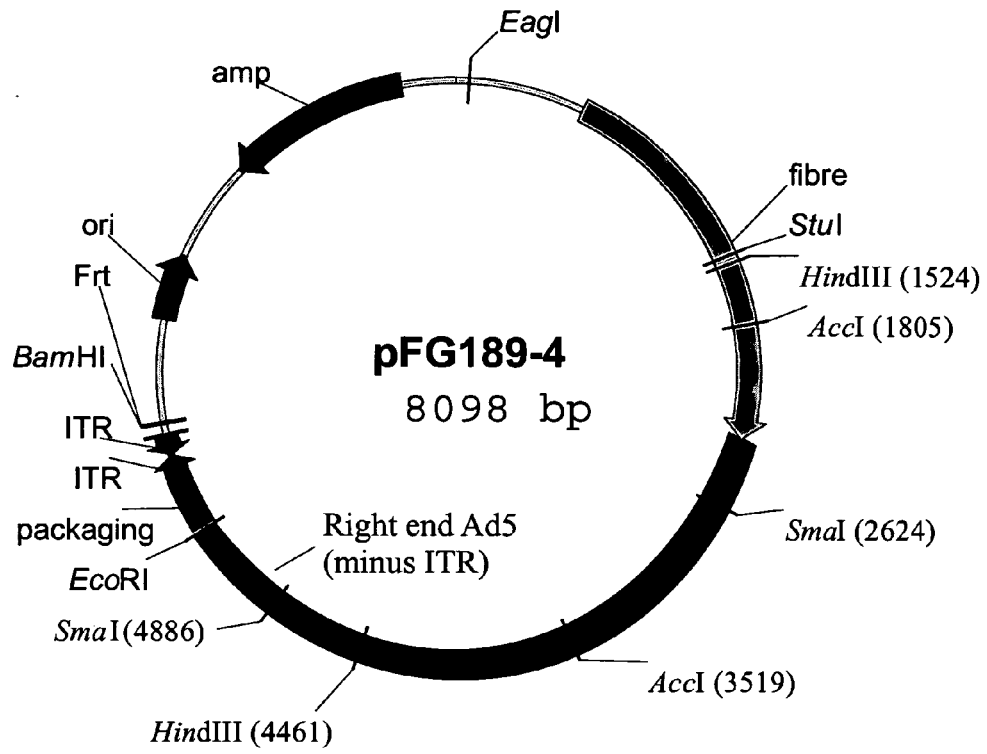
Figure 4E:
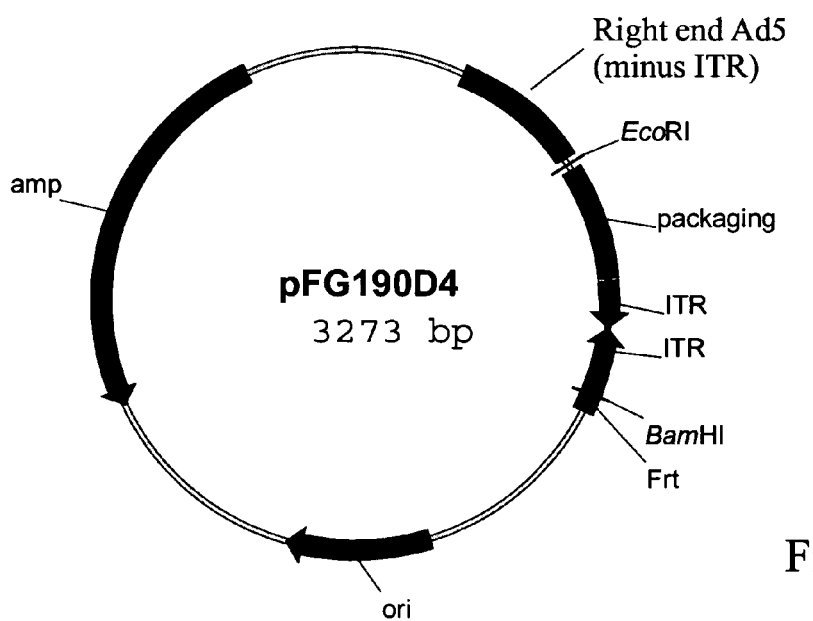

FIG. 4E shows how pFG189-4 was reduced in size by digestion with EagI and StuI, AccI, HindIII or SmaI followed by appropriate treatment of the DNA ends and ligation to produce a series of smaller plasmids designated as pFG190D1, D2, D3 or D4, the smallest of which, pFG190D4, is shown for illustrative purposes.

Figure 4F:
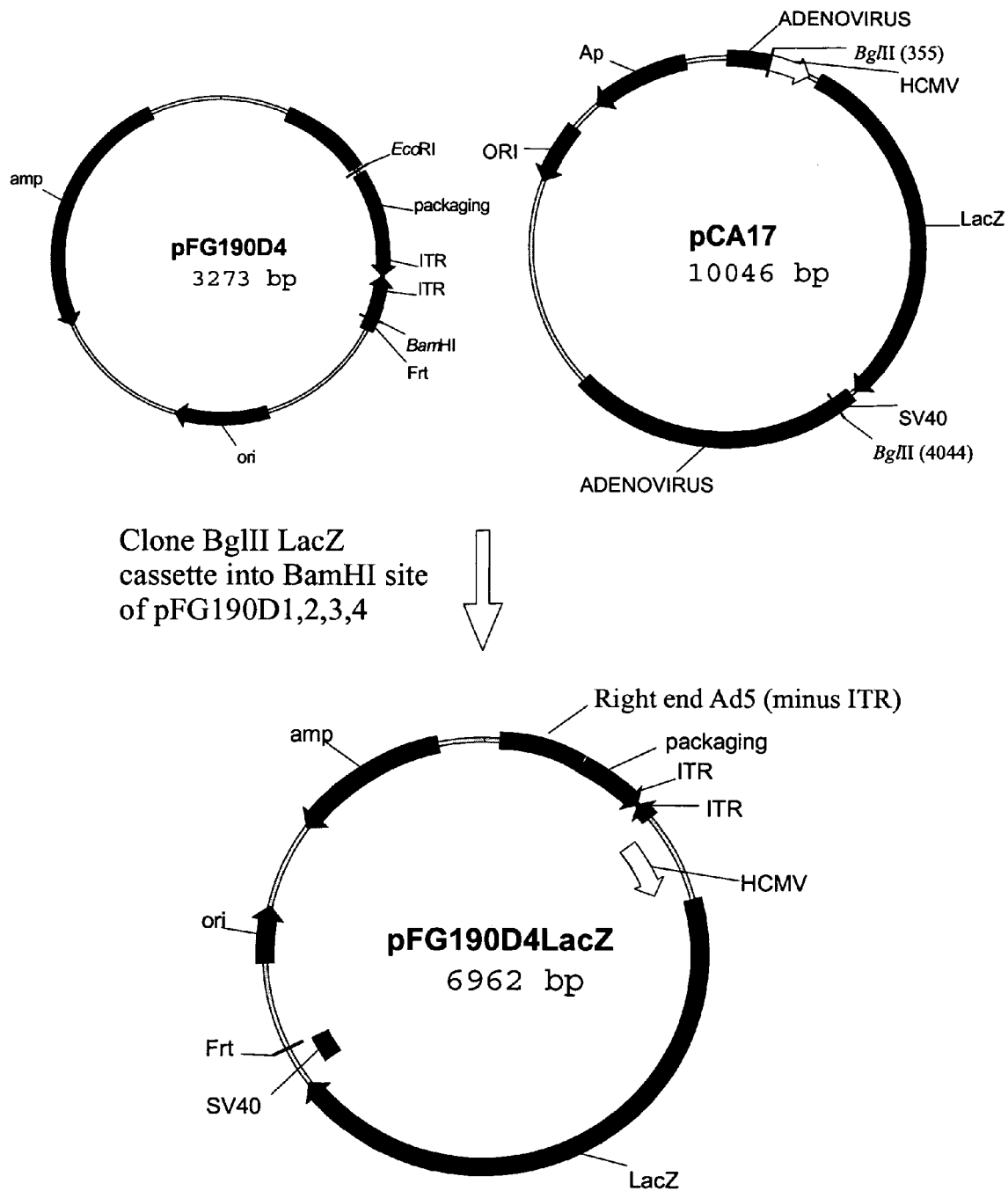

FIG. 4F shows the insertion of a BglII fragment containing a LacZ expression cassette into the BamHI site of pFG190D4 to create pFG190D4LacZ. Similar cloning was done with the larger pFG190D1, D2 and D3 plasmids.

Figure 4G:
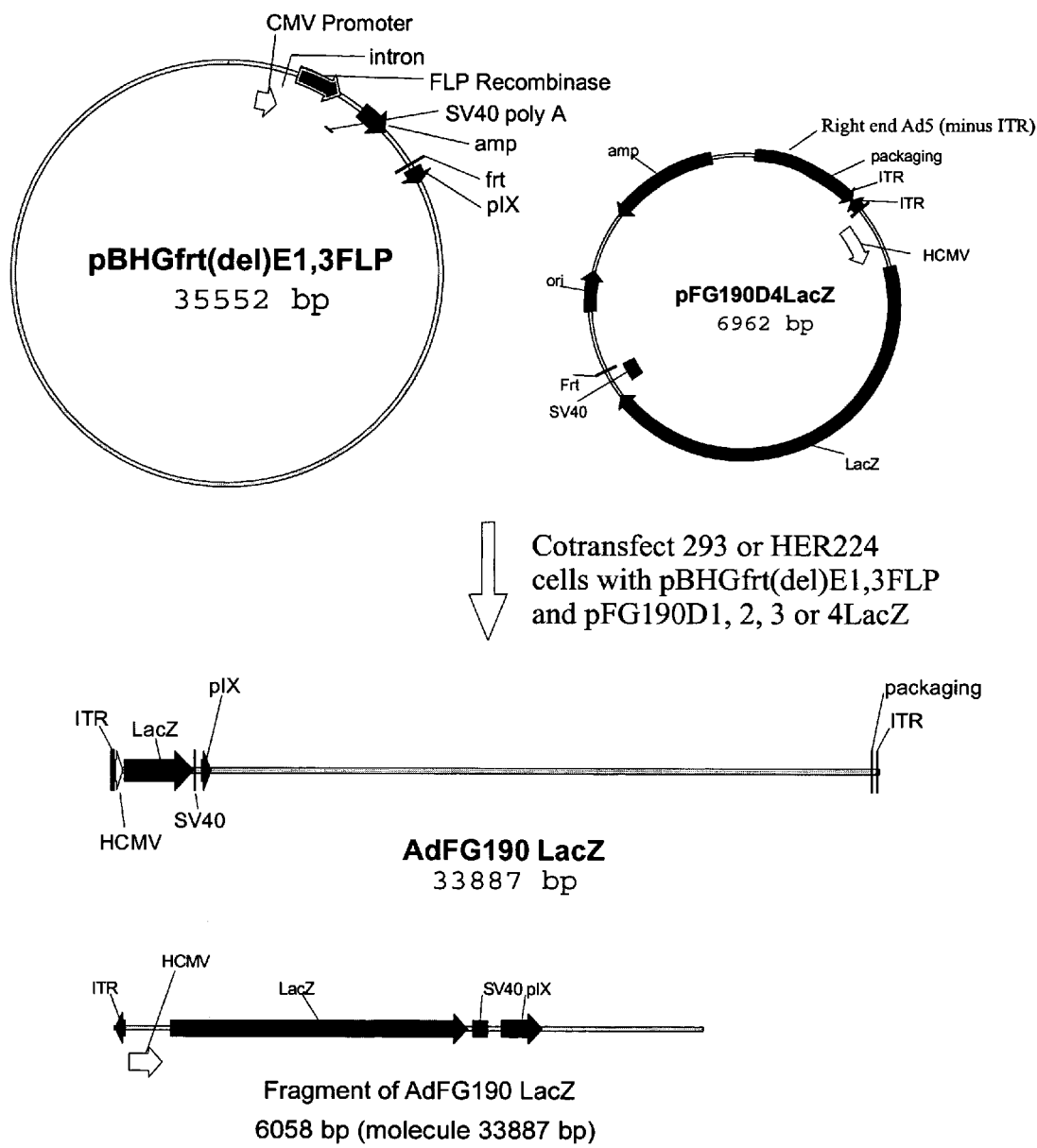

FIG. 4G illustrates the method used for rescue of sequences from pFG190D4LacZ into an infectious viral vector. pFG190D4LacZ (as well as the related larger LacZ shuttle plasmids) was cotransfected into 293 cells or HER224 cells with pBHGfrt(del)E1,3FLP (Microbix Biosystems) to produce AdFG190LacZ. The properties of this vector are as follows: It contains an ITR at the left end followed by the HCMV promoter driving LacZ expression and at the right end contains a packaging signal and ITR.

Figure 4H:
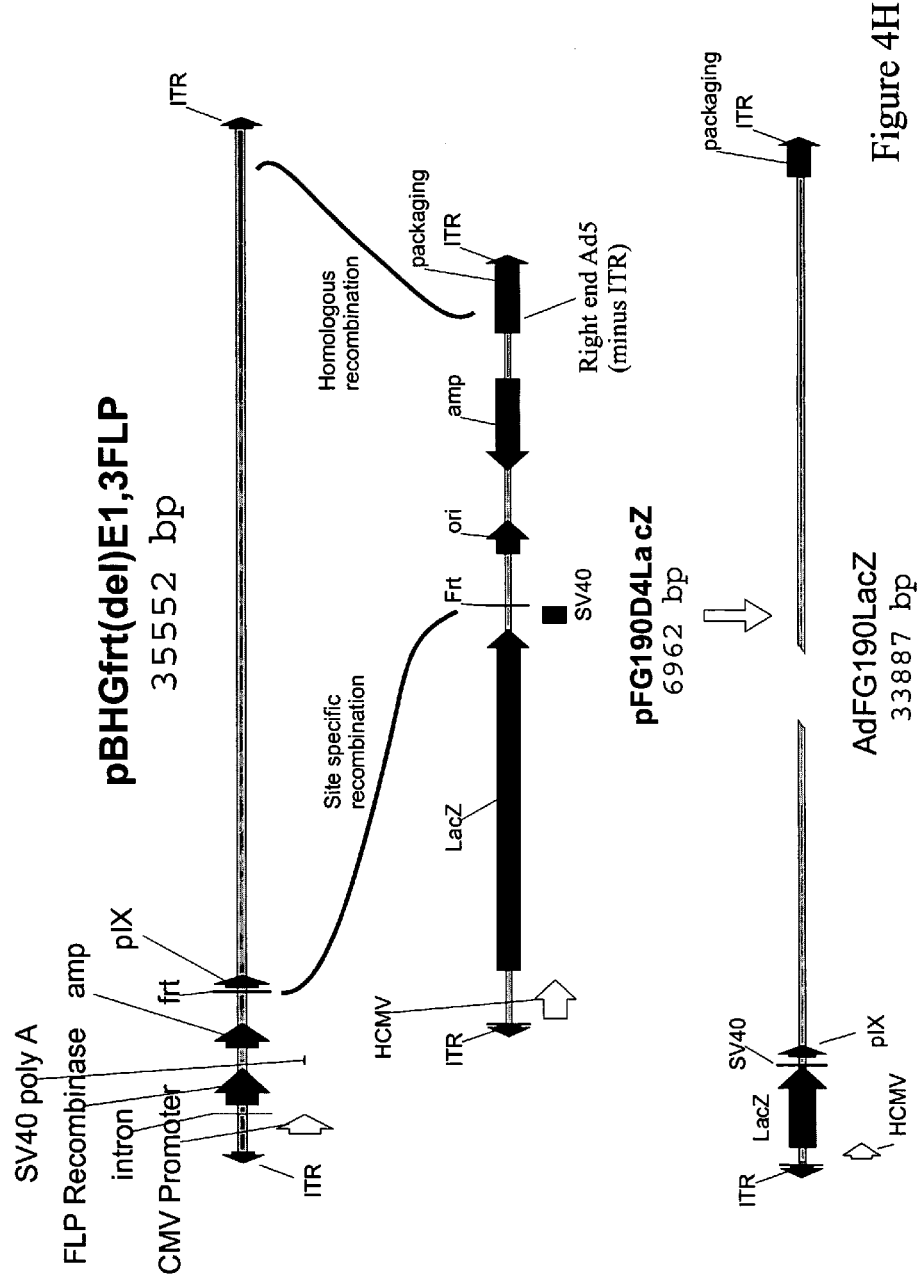

FIG. 4H presents a model for the recombination events that result in rescue of the LacZ expression cassette and rightward translocated packaging signal into virus. Two recombinations occur: a homologous recombination event between right end viral sequences common to pFG190D4LacZ and pBHGfrt(del)E1,3FLP and a site specific recombination catalyzed by FLP recombinase between the two frt sites. The structure of the resulting vector was confirmed by restriction enzyme digestion and gel electrophoresis and the vector was shown to express LacZ.

Figure 5:
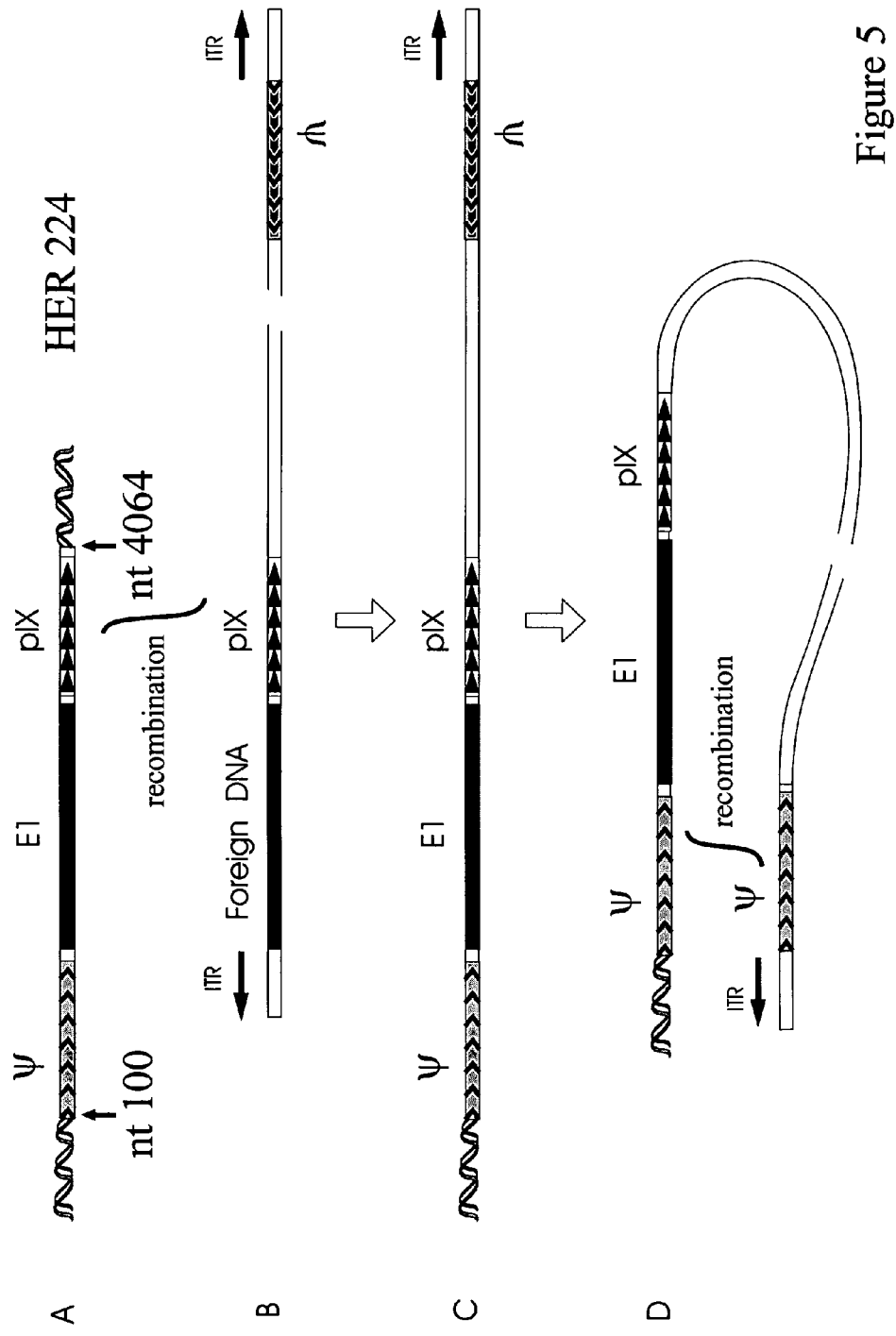

FIG. 5 illustrates a probable mechanism by which RCA are generated during propagation of AdFG190LacZ in HER224 cells. Two recombination events are all that are needed to generate and E1+ virus that would be predicted to have a packaging signal at each end of the genome. One recombination can occur between overlapping sequences to the right of E1, e.g. involving the pIX coding sequences and a second recombination can occur between the packaging signal derived from HER224 cell DNA and that at the right end of the vector DNA.

Figure 6:
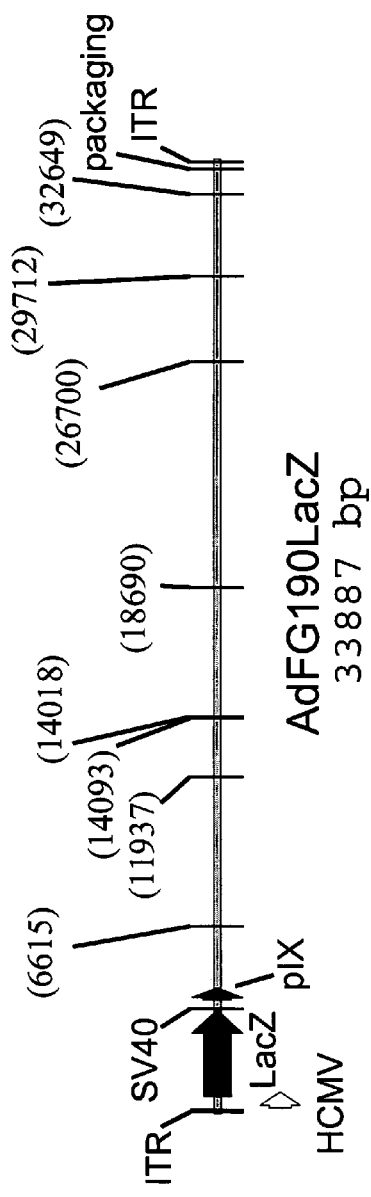
Figure 6:
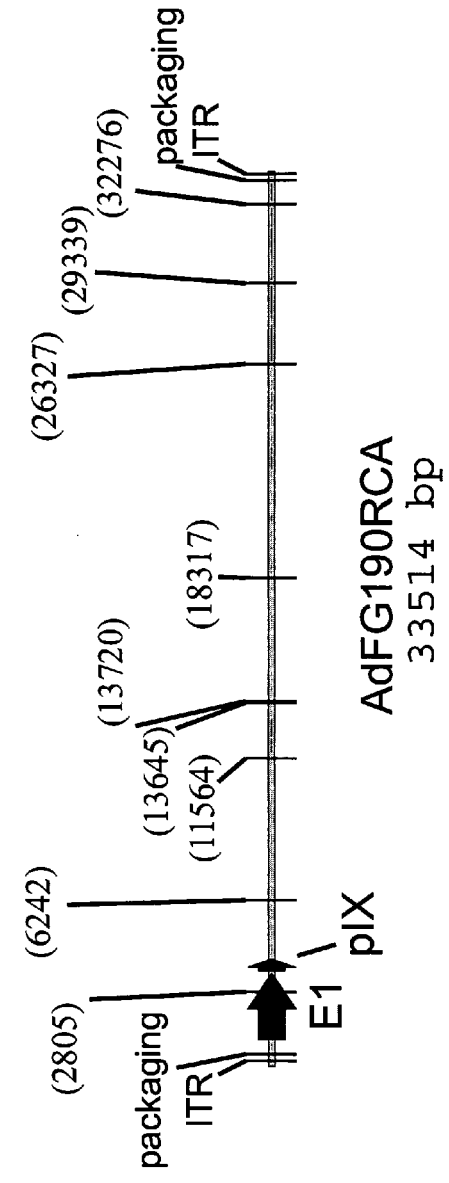

FIG. 6 illustrates the structure of AdFG190LacZ and the predicted structure of RCA generated by the two step homologous recombination process illustrated in FIG. 5. Restriction enzyme digestion and gel electrophoresis confirmed that the RCA generated from AdFG190LacZ had a packaging signal at both ends of the genome as expected from the model shown in FIG. 5.

Figure 7A:
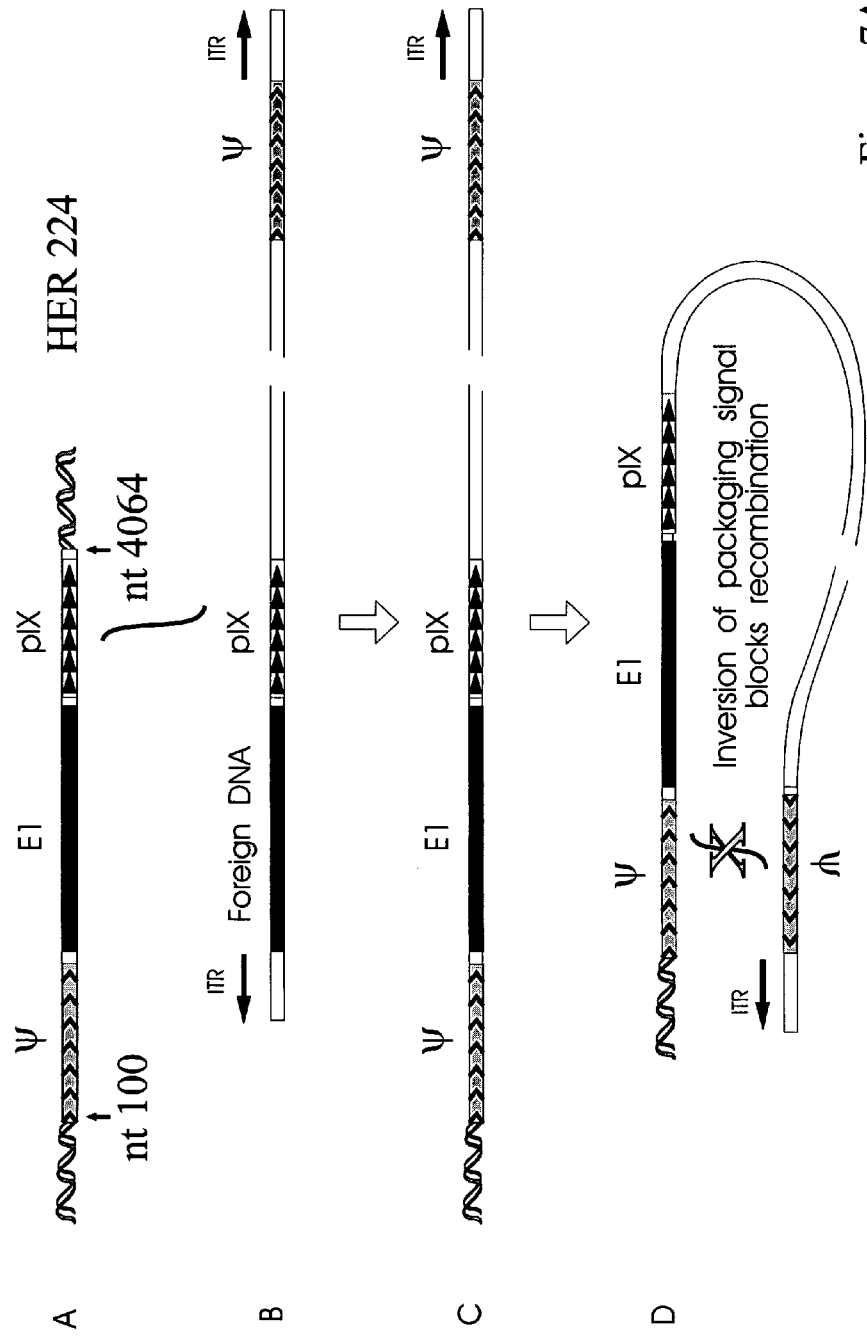

FIG. 7A illustrates a possible approach to avoid the second recombination event of FIG. 5 by inverting the packaging signal at the right end of the vector genome. It can be seen from panel D that if the packaging signal at the right end of the vector genome were inverted with respect to its normal orientation relative to the adjacent ITR then the recombination event illustrated in FIG. 5D could not occur because the sequences of the two packaging signals would not be aligned.

Figure 7B:
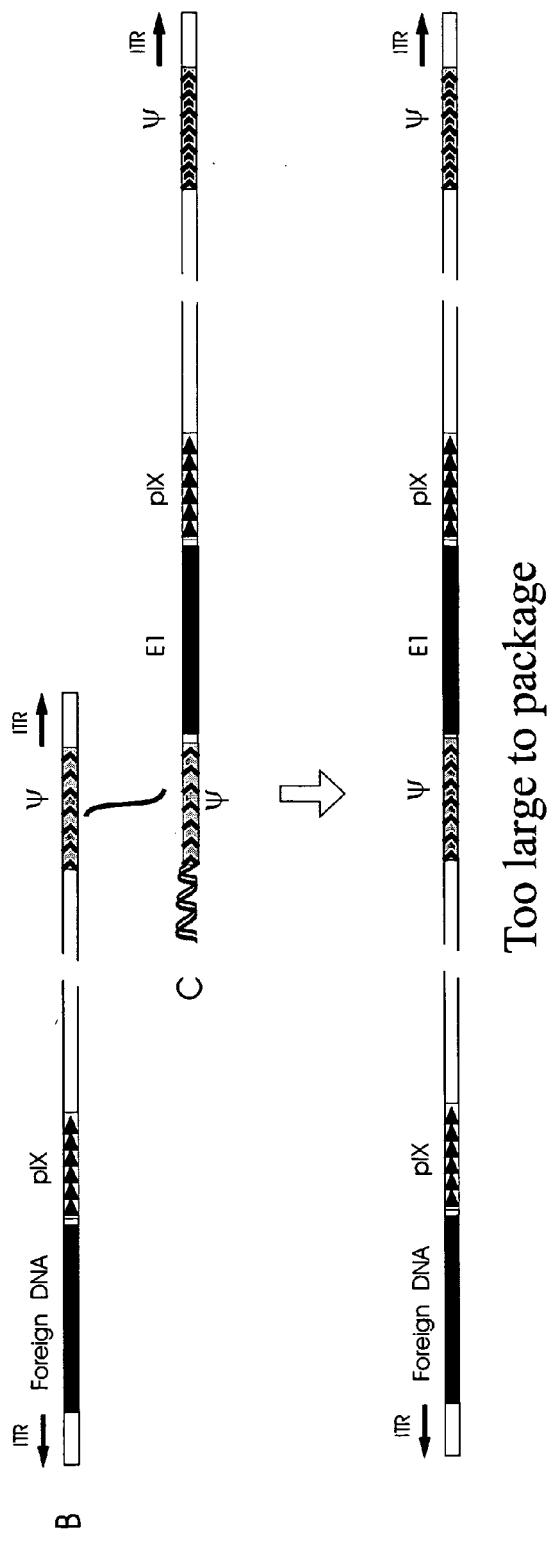

FIG. 7B illustrates possible homologous recombination events between DNA species B and C of FIG. 7A showing how a non-packageable E1+virus could be generated. Thus inversion of the packaging signal at the right end of the vector DNA would not prevent recombination but the result would be a nonviable virus.

Figure 8A:
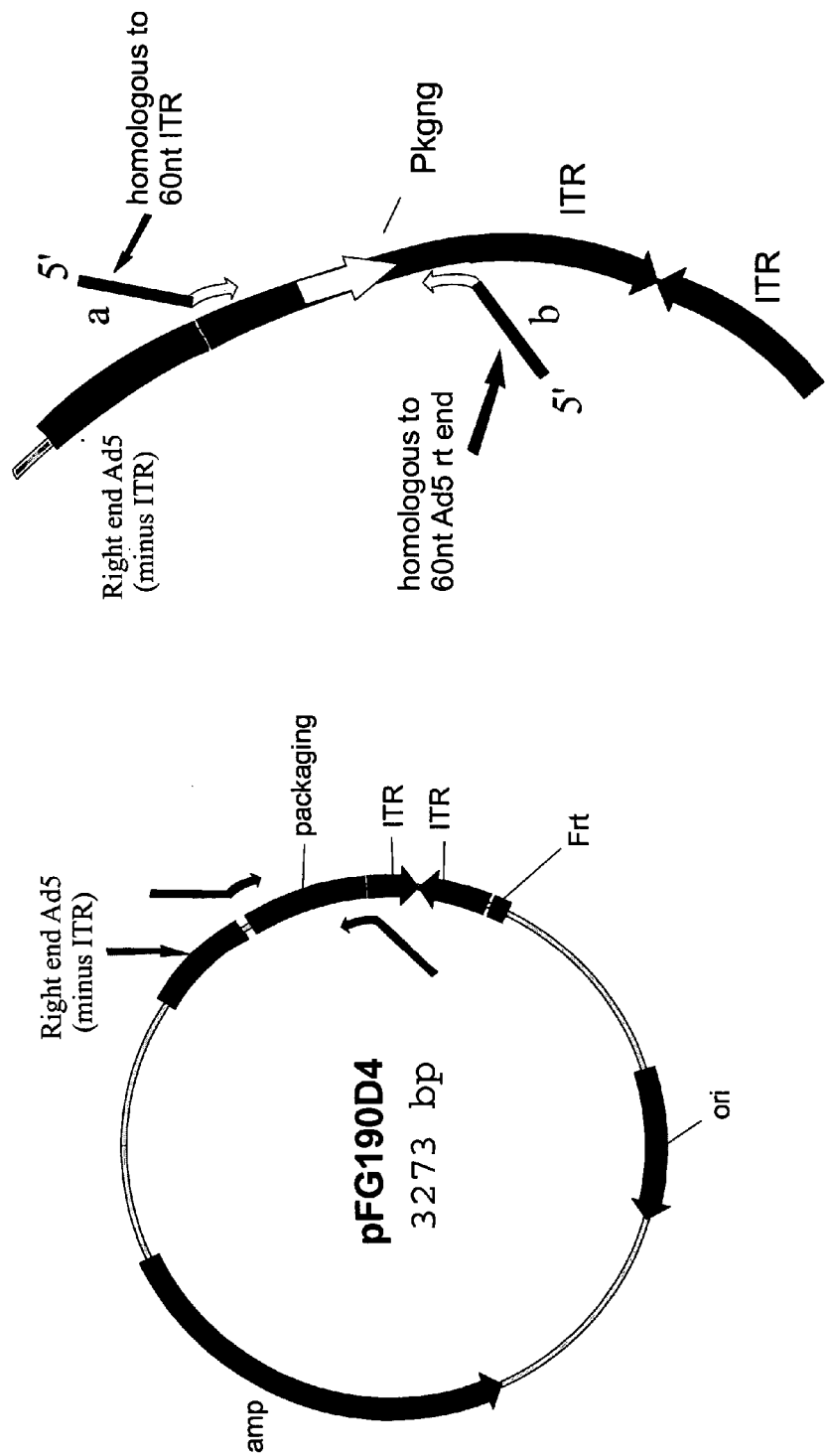
Figure 8B:
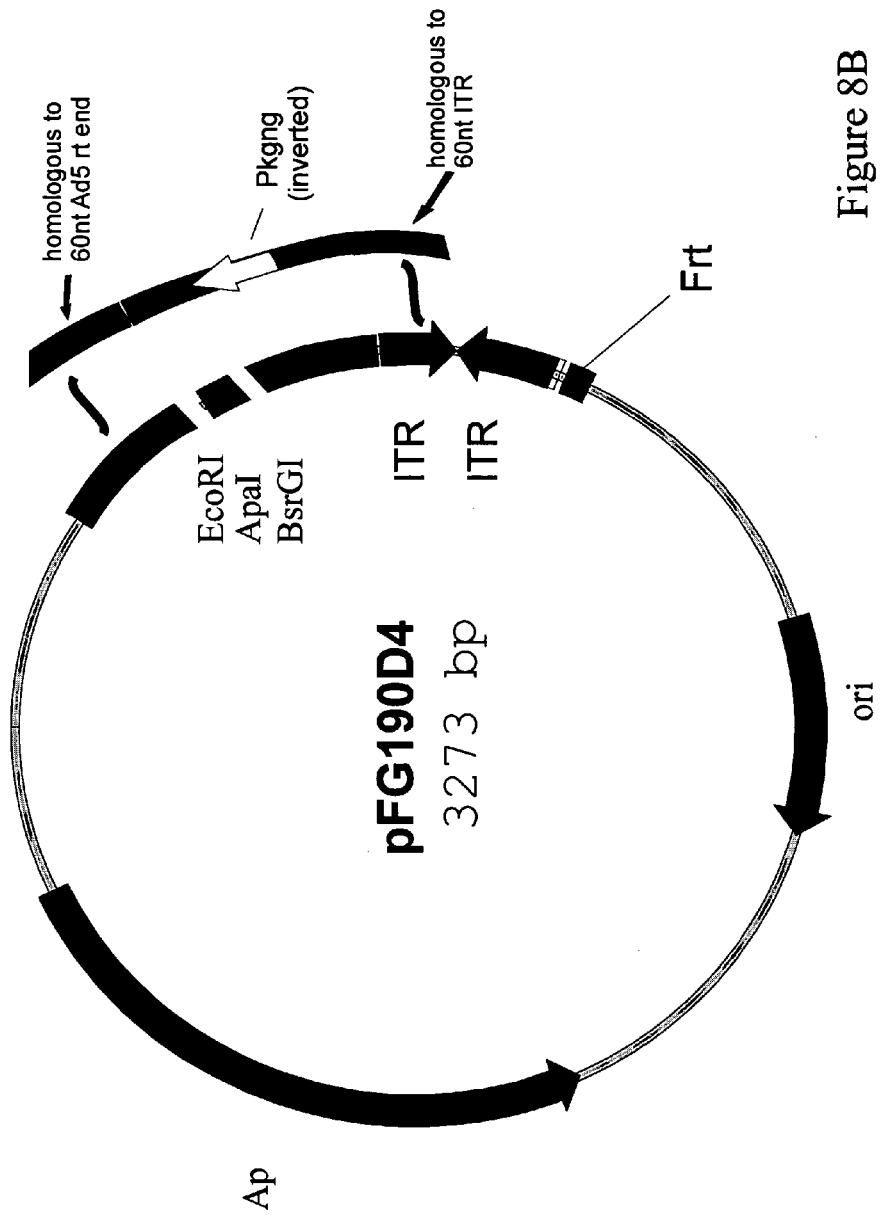

FIG. 8 illustrates a strategy to invert the packaging signal at the right end of the genome in Recombinant adenoviral vectors. The first step (FIG. 8A) utilizes a PCR reaction to amplify a DNA segment comprising the packaging signal and flanked by sufficient DNA (60 or more nt) on either side to permit homologous recombination (FIG. 8B) with pFG190D4 DNA that has been cleaved in the vicinity of the packaging signal by one or more of EcoRI, ApaI and BsrGI. The oligonucleotide primers are designed in such a way that the packaging signal is inverted in orientation after reintroduction into pFG190D4. A viral vector with an inverted packaging signal at the right end of the genome is then generated by cotransfection and recombination with pBHGfrt(del)E1,3FLP as in FIG. 4G.

Figure 9:
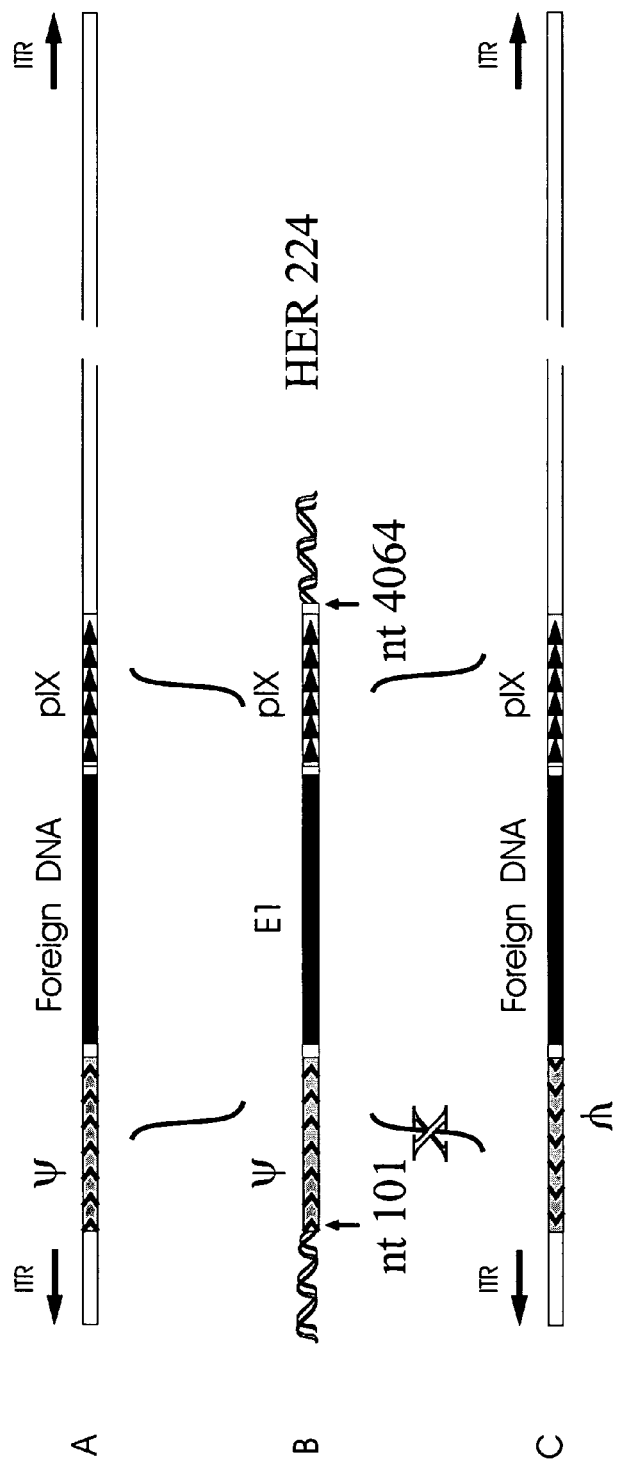

FIG. 9 illustrates a simpler possible approach to solving the problem of RCA formation by inverting the packaging signal at the left end of a typical FG vector and propagating the vector in HER224 cells. As in the case of inversion of the packaging signal at the right end of the vector genome, homologous recombination events between sequences to left and to right of the foreign DNA insert are not prevented, but the recombinations do not result in viable E1+viruses.

Figure 10A:
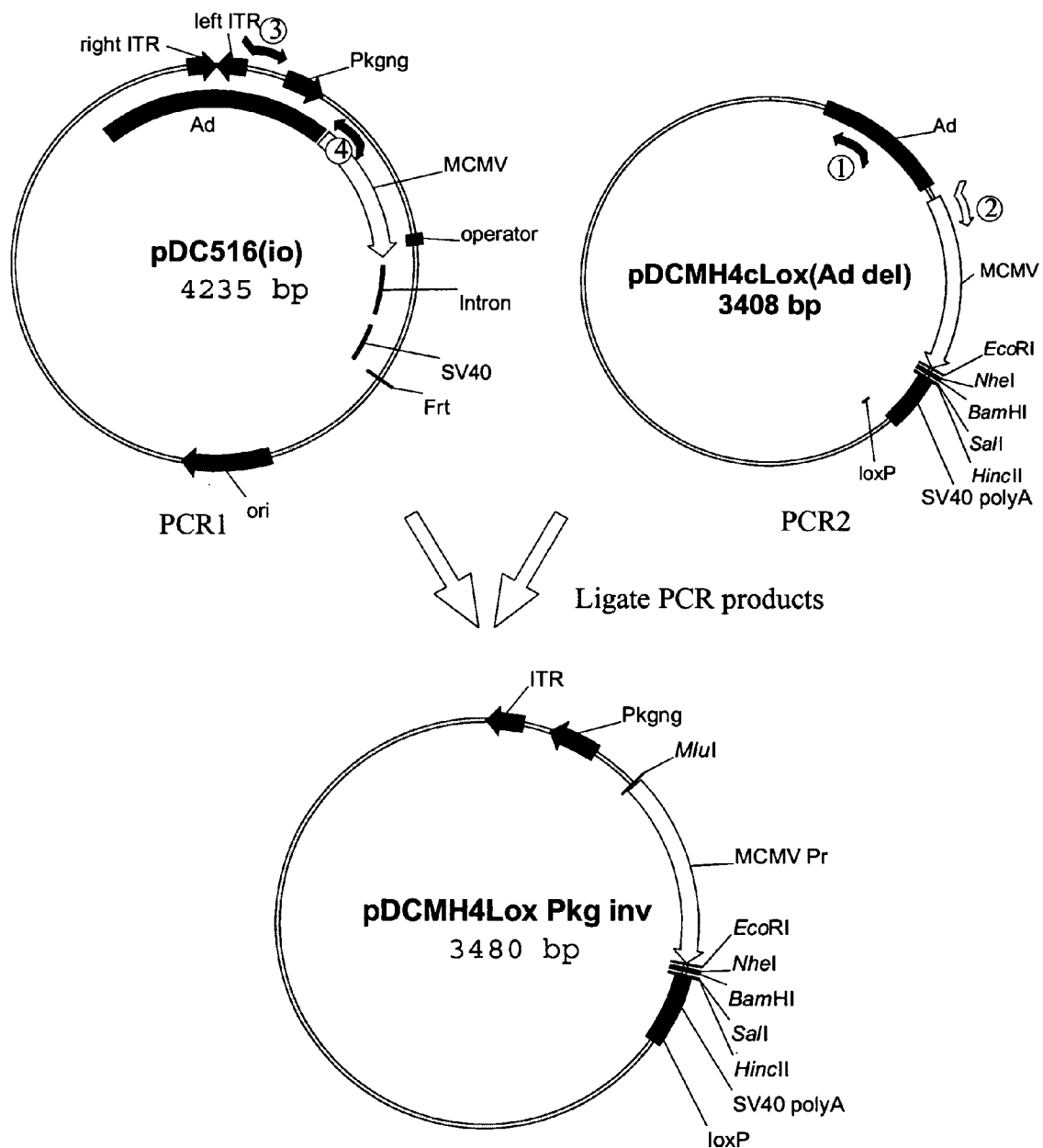
Figure 10C:
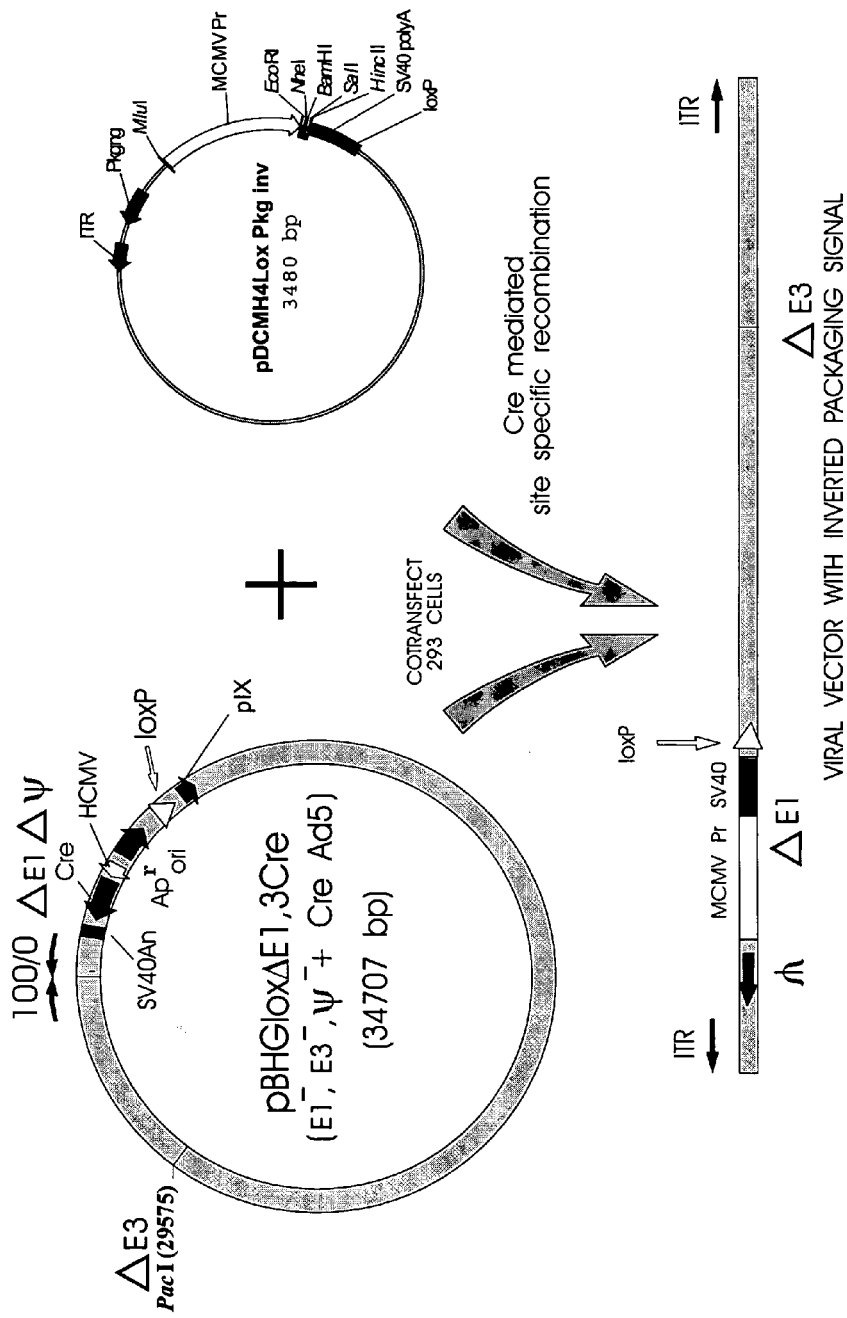

FIGS. 10A–C illustrate a strategy used to generate a FG vector having a promoter and poly A sequence at the left end of the vector genome and having an inverted packaging signal. Two PCR reactions were carried out (FIG. 10A) using two pairs of oligonucleotides (FIG. 10B) designed to permit cleavage with Spe I and Mlu I and ligation of the products of PCR 1 and PCR 2 such that the resulting ligation product consists of a new plasmid having an inverted packaging signal. Cotransfection of E1 complementing host cells such as HER224 cells results in efficient rescue of the sequences of the shuttle plasmid into a viral vector as shown in FIG. 10C. The system for vector isolation illustrated in FIG. 10C depends on site specific recombination between pBHGlox(del)E1,3Cre (Microbix Biosystems) and the shuttle plasmid pDCMH4LoxPkgn inv (in this case mediated by Cre recombinase) as described in U.S. Pat. No. 6,379,943.

Figure 11A:
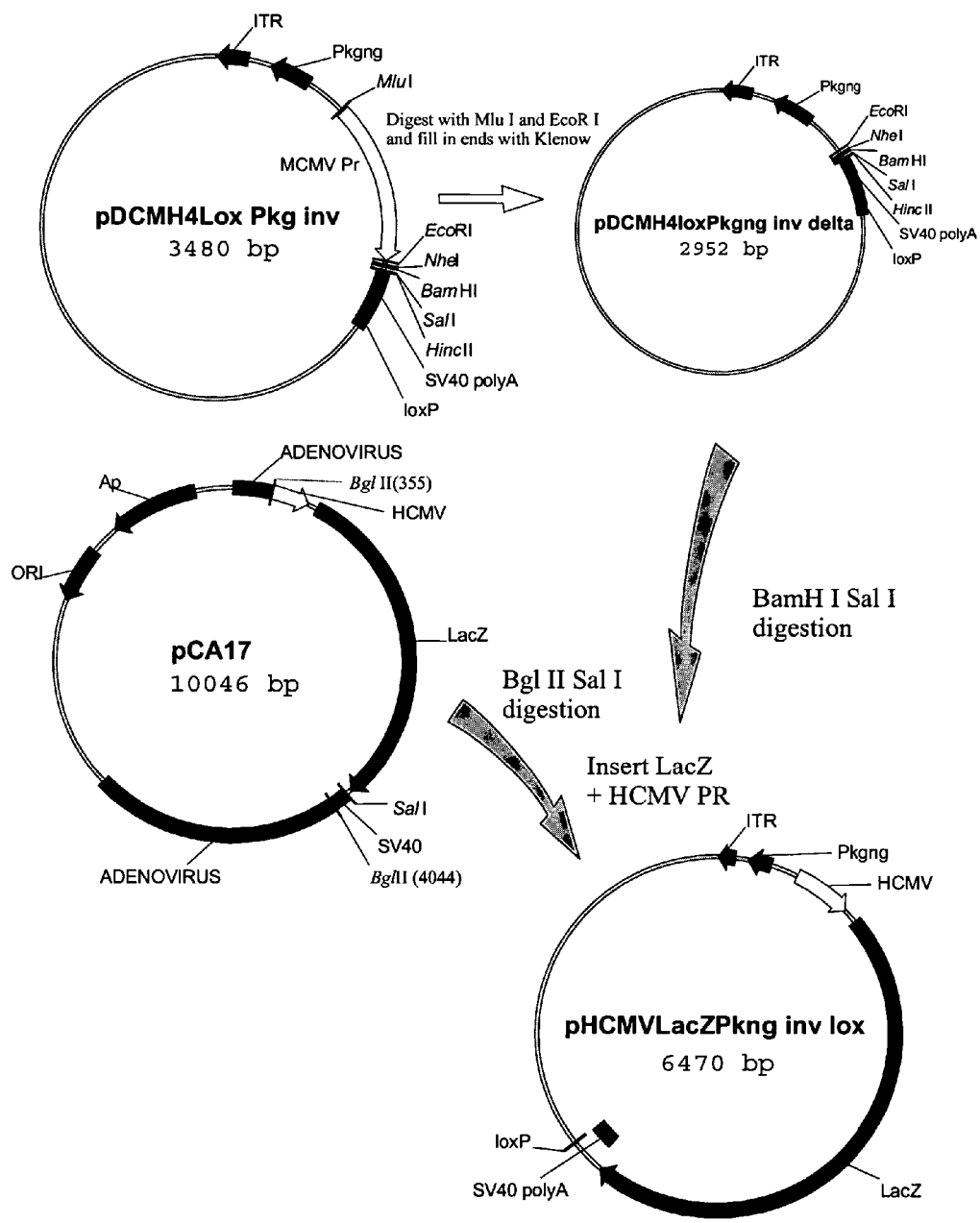

FIG. 11A illustrates construction of a shuttle plasmid containing a LacZ expression cassette for rescue into a vector by the method illustrated in FIG. 10C. A BglII to Sal I fragment containing a LacZ cassette was excised from pCA17 (Microbix Biosystems) and inserted into the shuttle plasmid containing an inverted packaging signal (after removing the MCMV promoter from the shuttle by excising the DNA segment between MluI and EcoRI). The resulting plasmid containing LacZ expressed from the HCMV promoter was then rescued into virus by cotransfection with the genomic plasmid shown in FIG. 10C and site specific recombination.

Figure 11B:
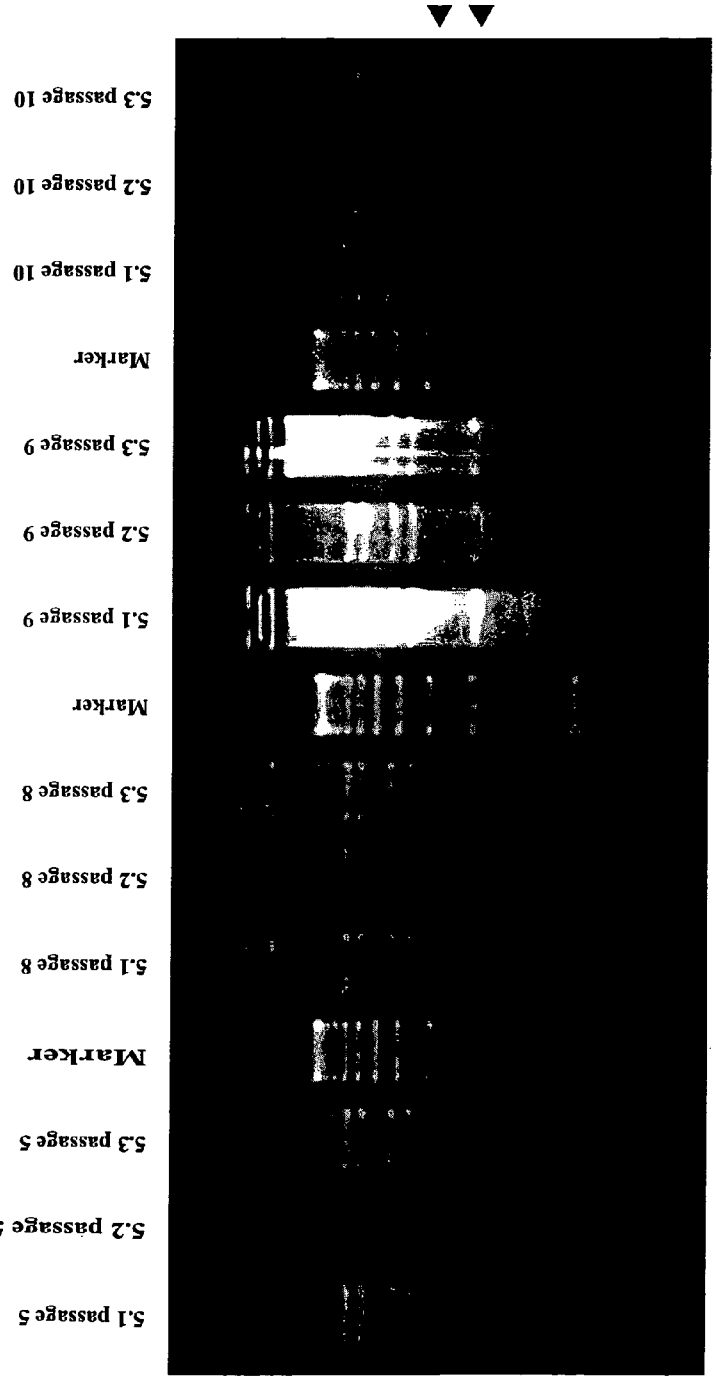

FIG. 11B shows the results of restriction enzyme digestion and gel electrophoretic analysis of the structure of AdHCMVLacZPkgngInv virus DNA after up to 10 passages of the vector in 293 cells. The DNA pattern is that predicted by the HindIII restriction map of the vector shown below. In particular there is no evidence of bands attributable to RCA that would migrate in the positions indicated by the two black arrows.

FIG. 12 illustrates a strategy for generation of a FG vector having a GFP (Green Fluorescent Protein) expression cassette in a vector with an inverted packaging signal.

Figure 12A:
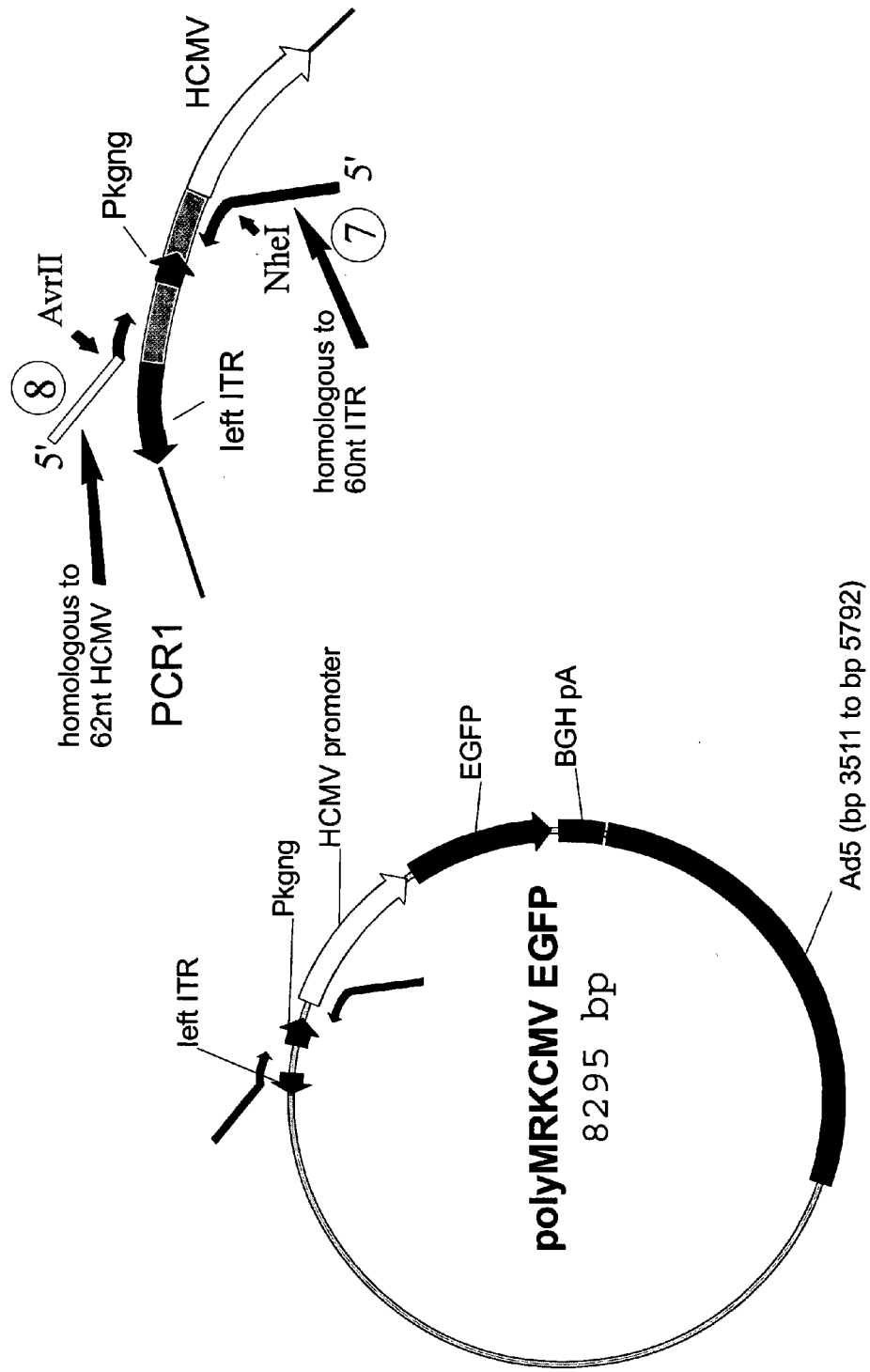

FIG. 12A illustrates the first step, involving a PCR reaction with oligonucleotides that amplify the packaging signal and that are terminated at their 5' ends by about 60 or 62 nt of DNA homologous to HCMV or ITR sequences.

Figure 12B:
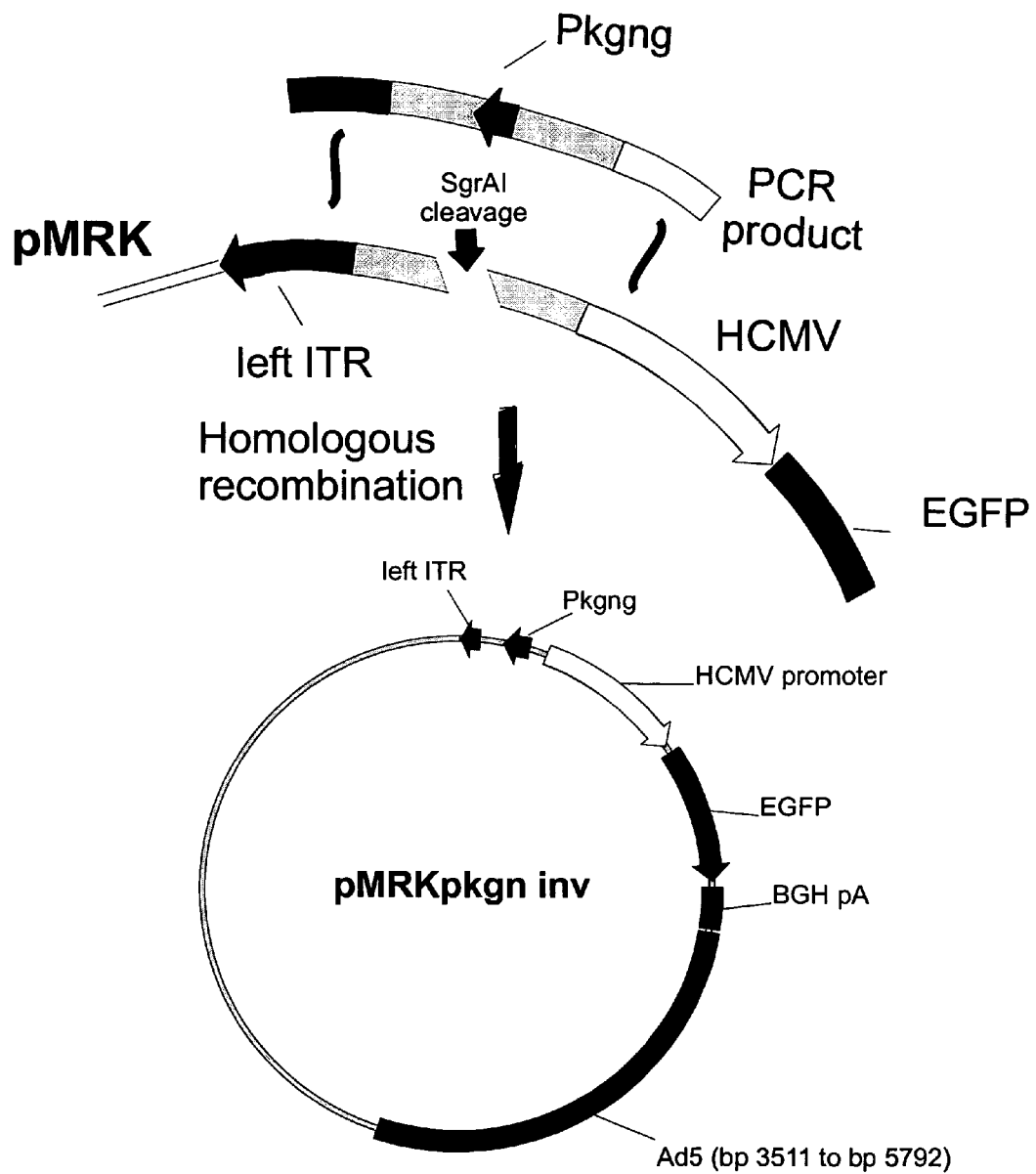

FIG. 12B illustrates the use of homologous recombination between the PCR product of FIG. 12A and polyMRKCMV EGFP (pMRK) linearized by SgrAI digestion to reinsert the packaging signal into pMRK in orientation opposite to the wt orientation.

FIG. 12C illustrates the design of oligonucleotides used for the PCR reaction illustrated in FIG. 12A.

FIGS. 13A–F illustrate another strategy for generation of a FG vector having a GFP expression cassette in a vector with an inverted packaging signal.

Figure 13A:
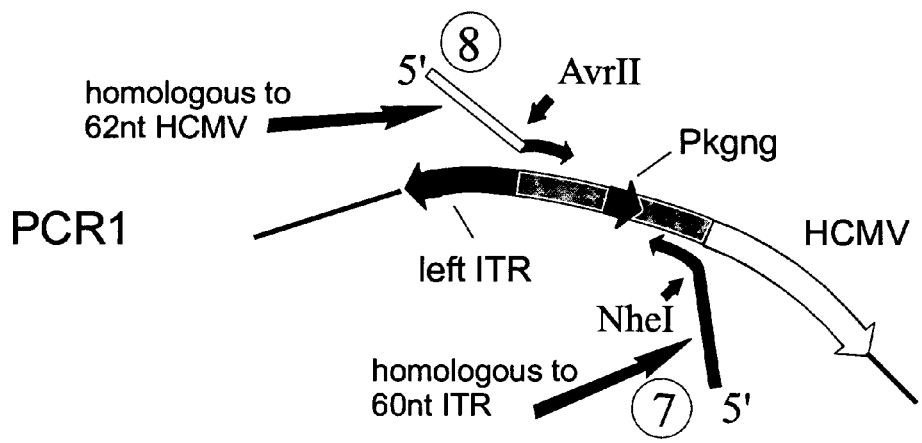
Figure 13A:
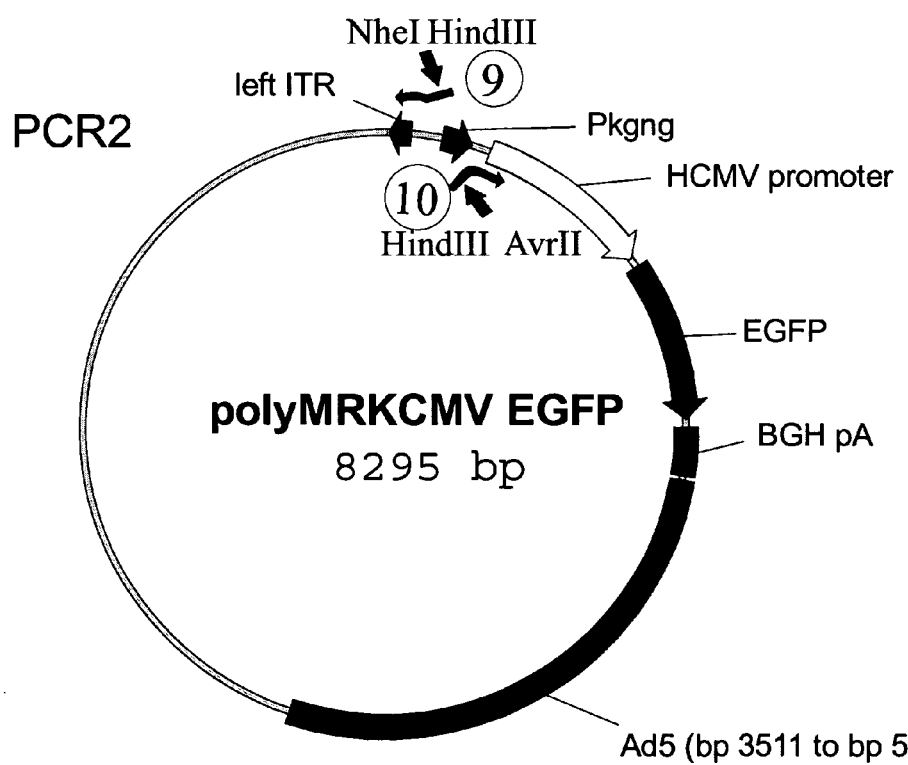

FIG. 13A illustrates the first step, involving a PCR reaction with the same oligonucleotides, 7 (SEQ ID NO:7) and 8 (SEQ ID NO:8), illustrated in FIG. 12C, to amplify the packaging signal from pMRK. A second PCR was carried out using oligonucleotides 9 (SEQ ID NO:9) and 10 (SEQ ID NO:10) (FIG. 13F) to amplify the entire pMRK plasmid except for the DNA segment comprising the packaging signal.

Figure 13B:
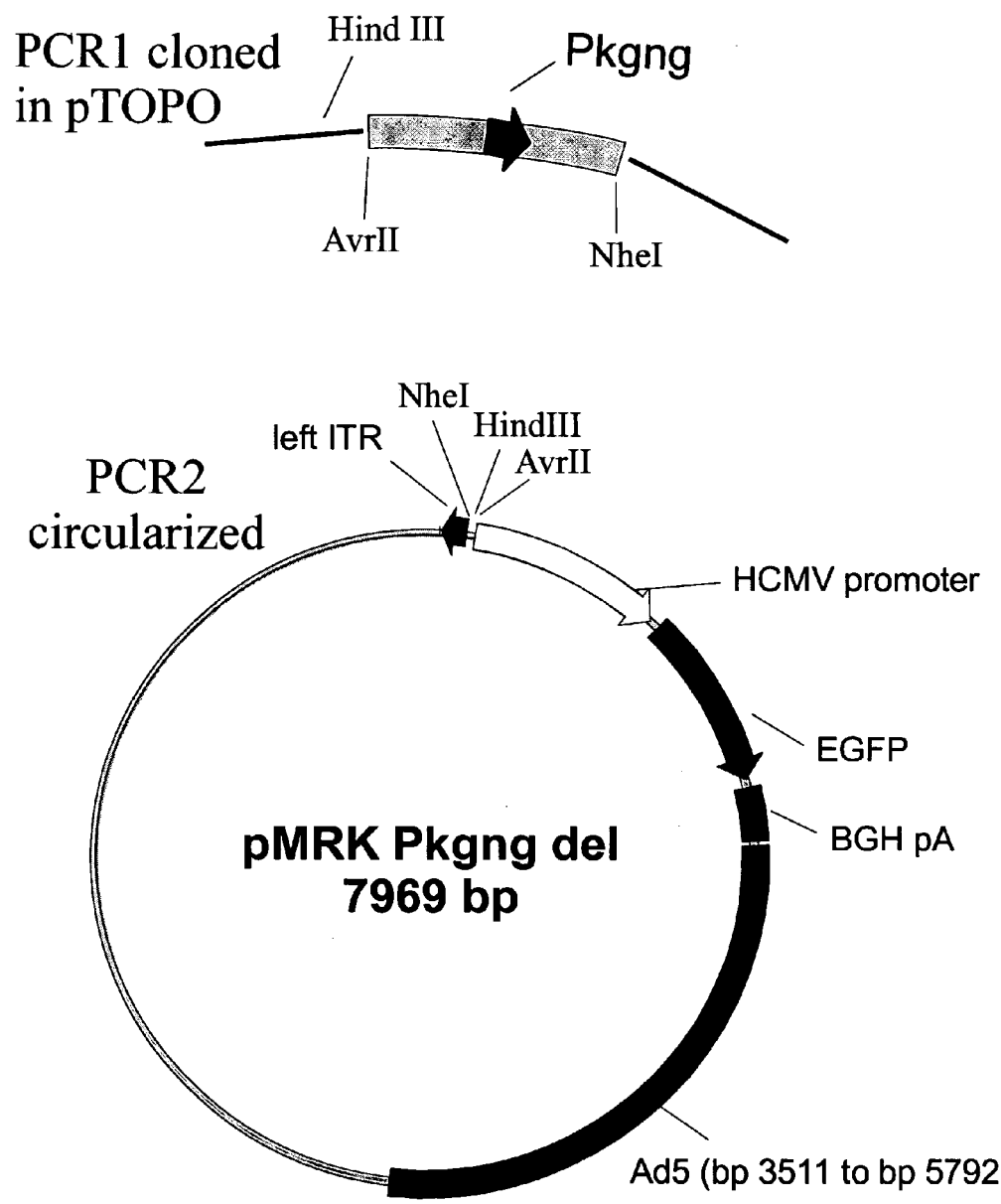

FIG. 13B illustrates the next step, involving cloning of the product of PCR reaction 1 into pCR2.1-TOPO (Invitrogen Inc.) and circularization of PCR product 2 by HindIII digestion and ligation to generate pMRKPkgngdel.

Figure 13C:
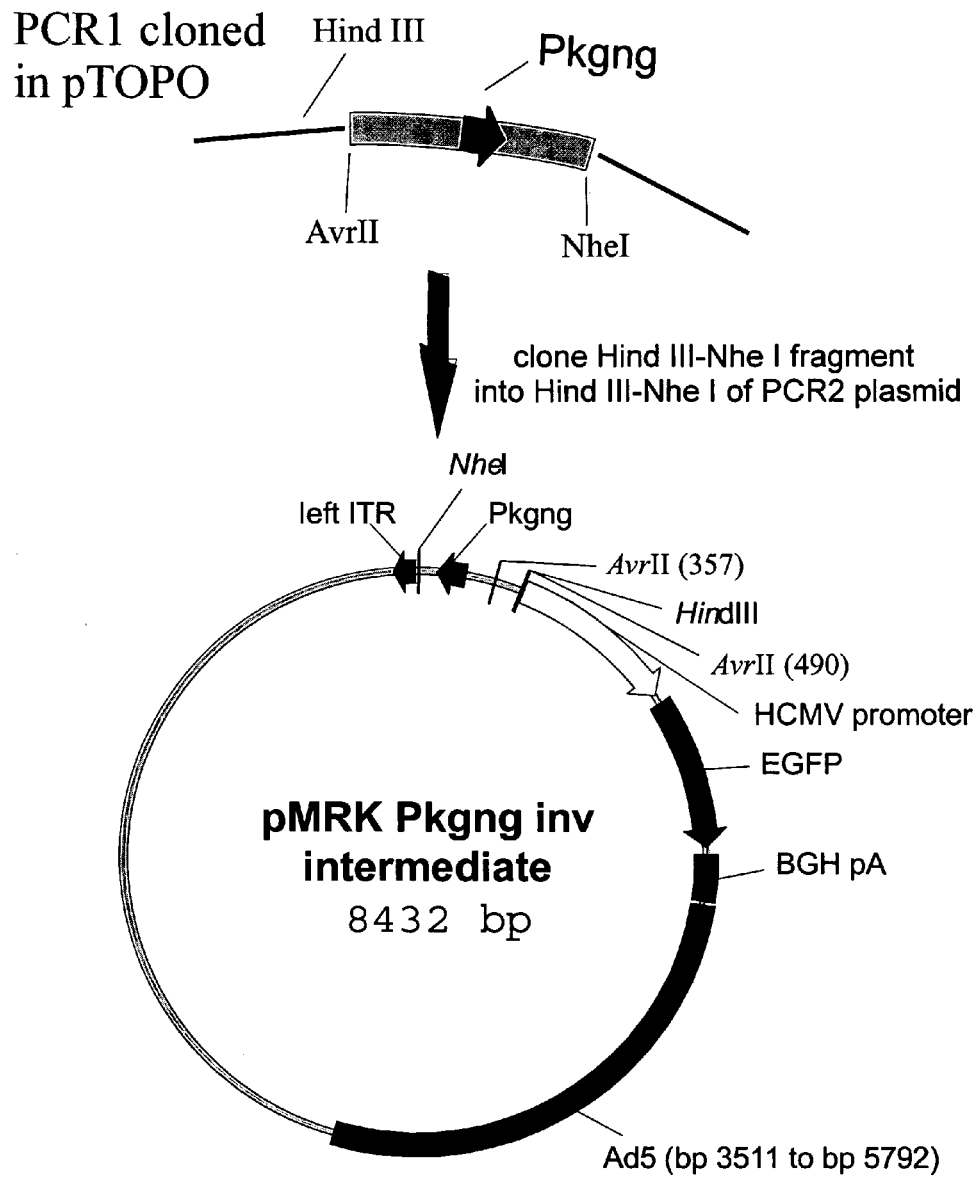

FIG. 13C illustrates the cloning of the product of PCR reaction 1 out of pTOPO by digestion with HindIII and NheI, purification of the DNA fragment containing the packaging signal and insertion of the fragment into the HindIII-NheI site of pMRKPkgngdel.

Figure 13D:
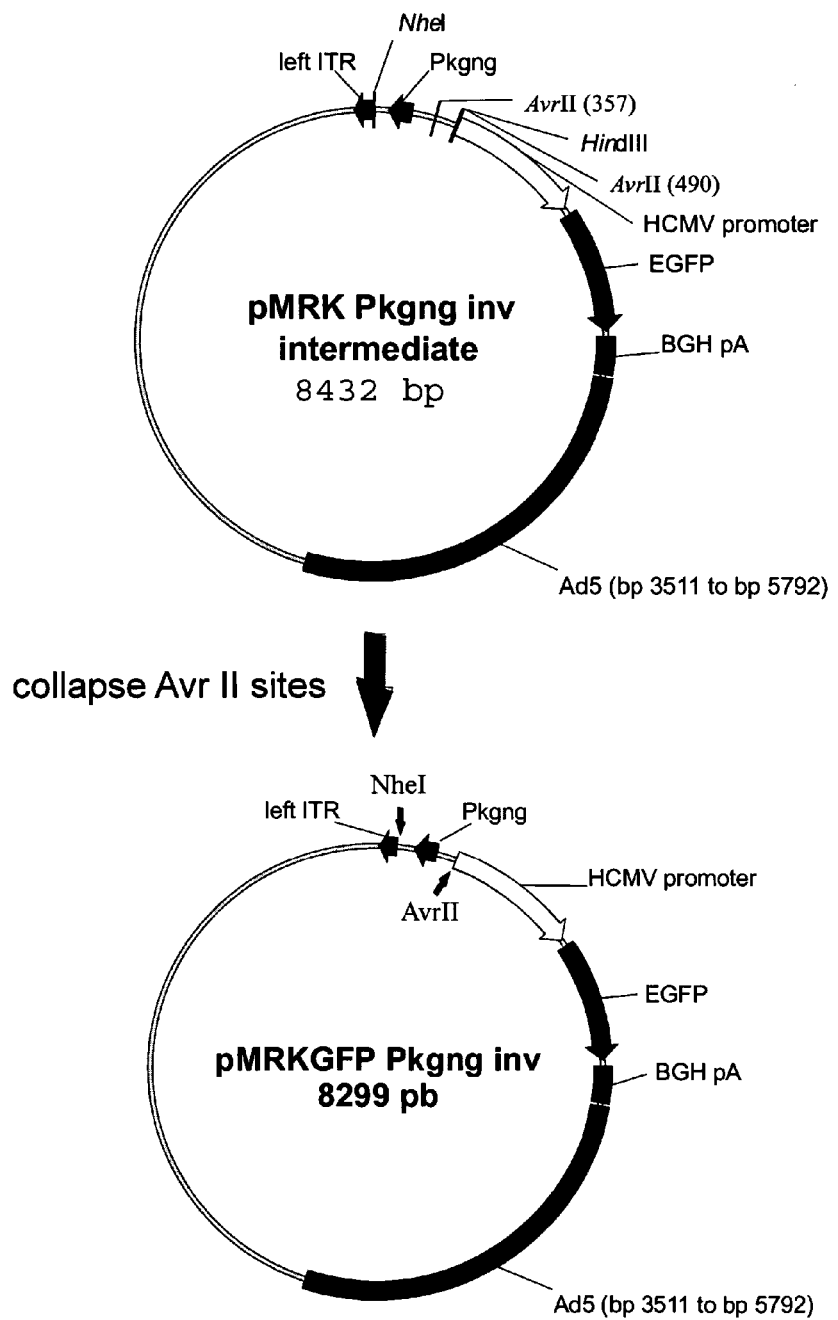

FIG. 13D illustrates the last step in generation of a shuttle plasmid containing an inverted packaging signal and a GFP expression cassette. Extraneous sequences derived from pTOPO were removed from pMRKPkgnginv intermediate by AvrII digestion and religation to create pMRKGFP Pkgnginv. This plasmid contains an inverted packaging signal and an EGFP expression cassette for synthesis of Green Fluorescent Protein. The EGFP cassette can easily be removed and substituted with polycloning sites or with other expression cassettes.

Figure 13E:
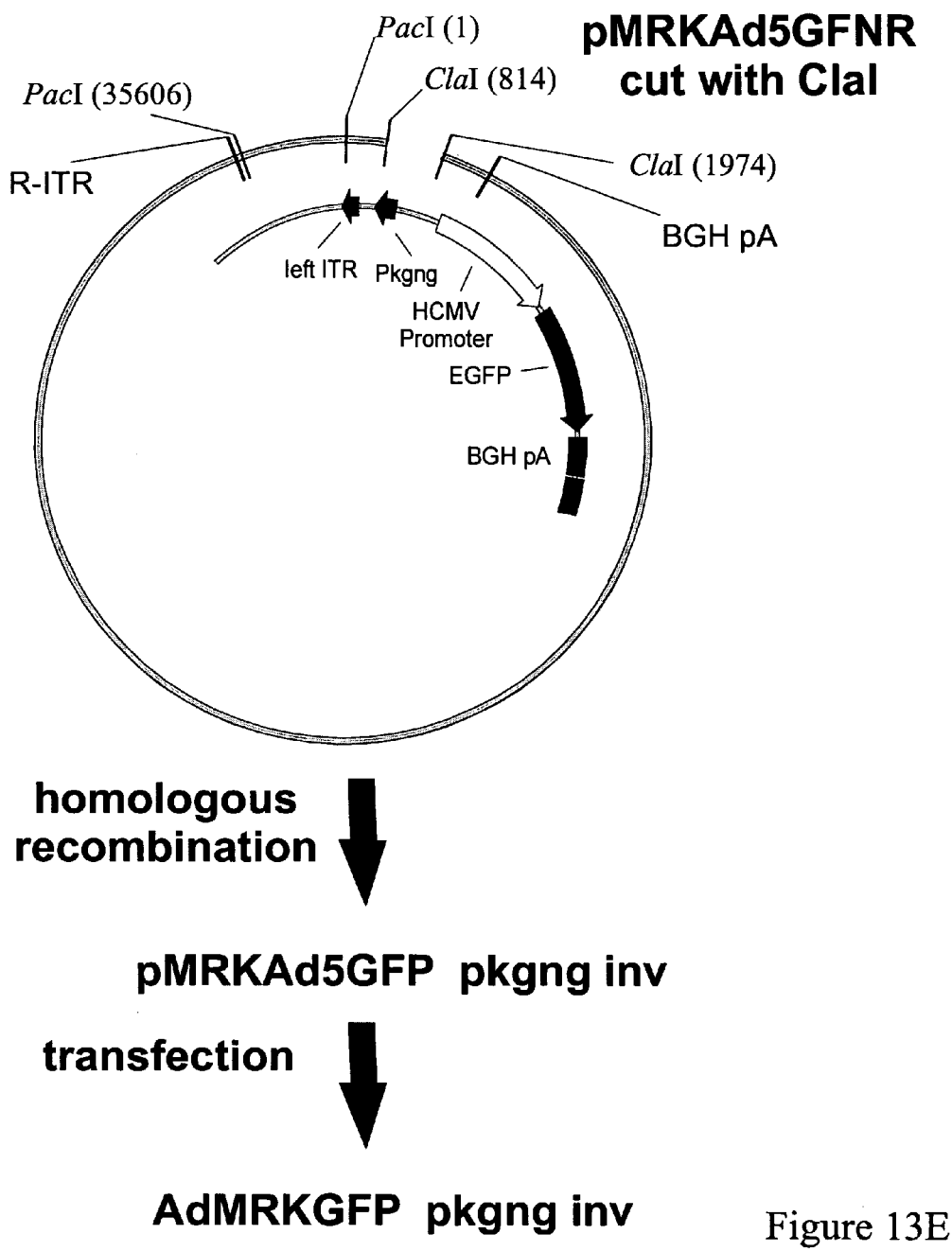

FIG. 13E illustrates the generation of a genomic plasmid containing an inverted packaging signal and a GFP expression cassette by homologous recombination in bacteria (Youil, R., Toner, T. J., Su, Q. and Kaslow, D. C. Rapid method for the isolation of full length adenoviral genomes by bacterial intermolecular homologous recombination. J. Virol. Methods 92: 91–97, 2001). Recombination between the shuttle plasmid of FIG. 13D and a genomic plasmid, pMRKAd5GFNR, that contains the entire Ad5 genome cloned into a bacterial plasmid as a linear insert flanked by PacI sites adjacent to the left and right ITRs results in insertion of the inverted packaging signal and EGFP expression cassette into the genomic plasmid to create pMRKAd5GFP pkgng inv. Excision of the vector DNA backbone by PacI digestion and transfection of 293 cells, PERC6 cells or HER224 cells resulted in production of the infectious Recombinant adenoviral vector AdMRKGFP pkgng inv comprising an inverted packaging signal and GFP cassette.

FIG. 13F illustrates the design of oligonucleotides 9 (SEQ ID NO:9) and 10 (SEQ ID NO:10) used for the PCR reaction 1 illustrated in FIG. 13A. The oligonucleotides contain HindIII sites near their 5' termini which were used to circularize the resulting PCR product (FIG. 13B).

Figure 14A:
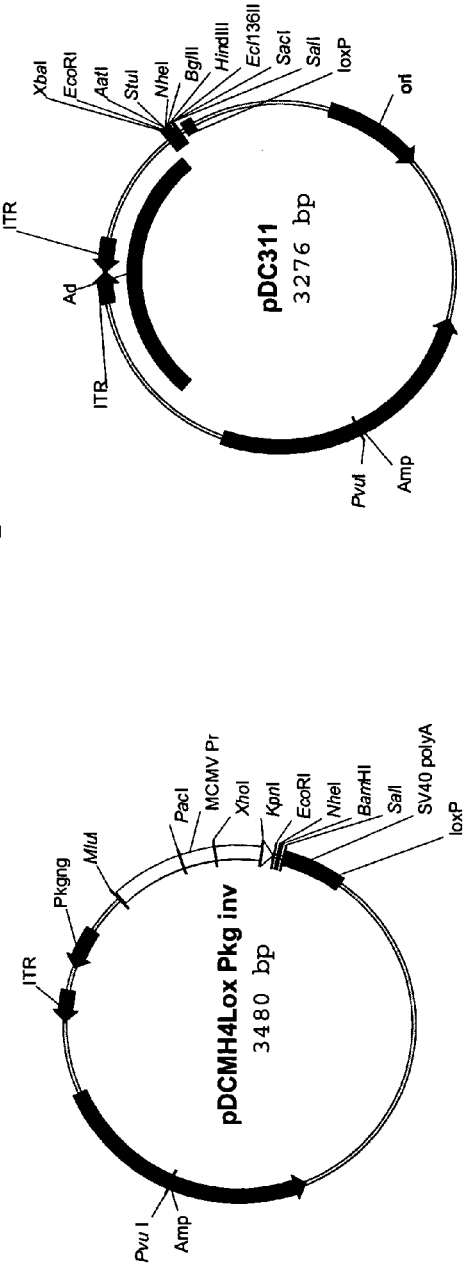
Figure 14A:
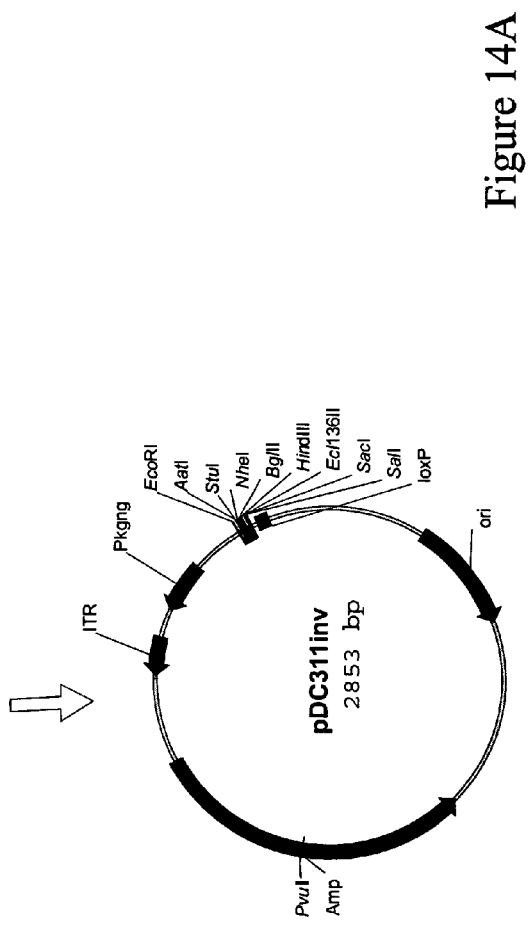
Figure 14B:
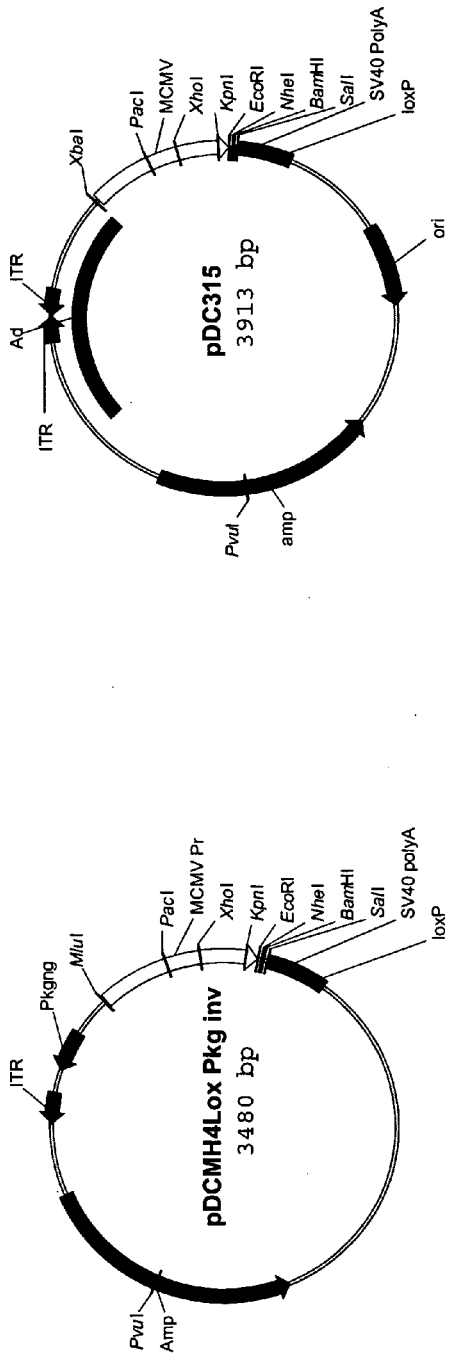
Figure 14B:
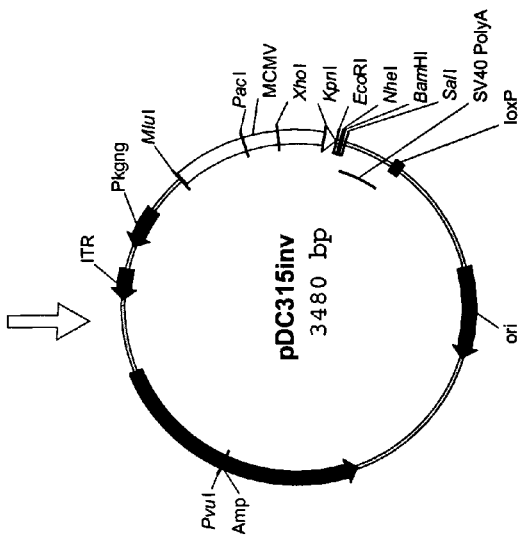

FIGS. 14A–B diagrammatically illustrate methods for modification of commercially available shuttle plasmids (of Kits D, E, F, I and J from Microbix Biosystems) so that these commercially available plasmids can be used for construction of recombinant Adenovirus vectors having an inverted packaging signal. In FIG. 14A a fragment of pDCMH4LoxPkginv from PvuI to MluI is transferred into the PvuI to XbaI region of pDC311 resulting in substitution of the wild type packaging signal of pDC311 with an inverted packaging signal in pDC311inv. In FIG. 14B, a fragment of pDCMH4LoxPkginv from PvuI to PacI is transferred into the PvuI to PacI region of pDC315 resulting in substitution of the wild type packaging signal in pDC311 with an inverted packaging signal in pDC315inv.

Figure 15:
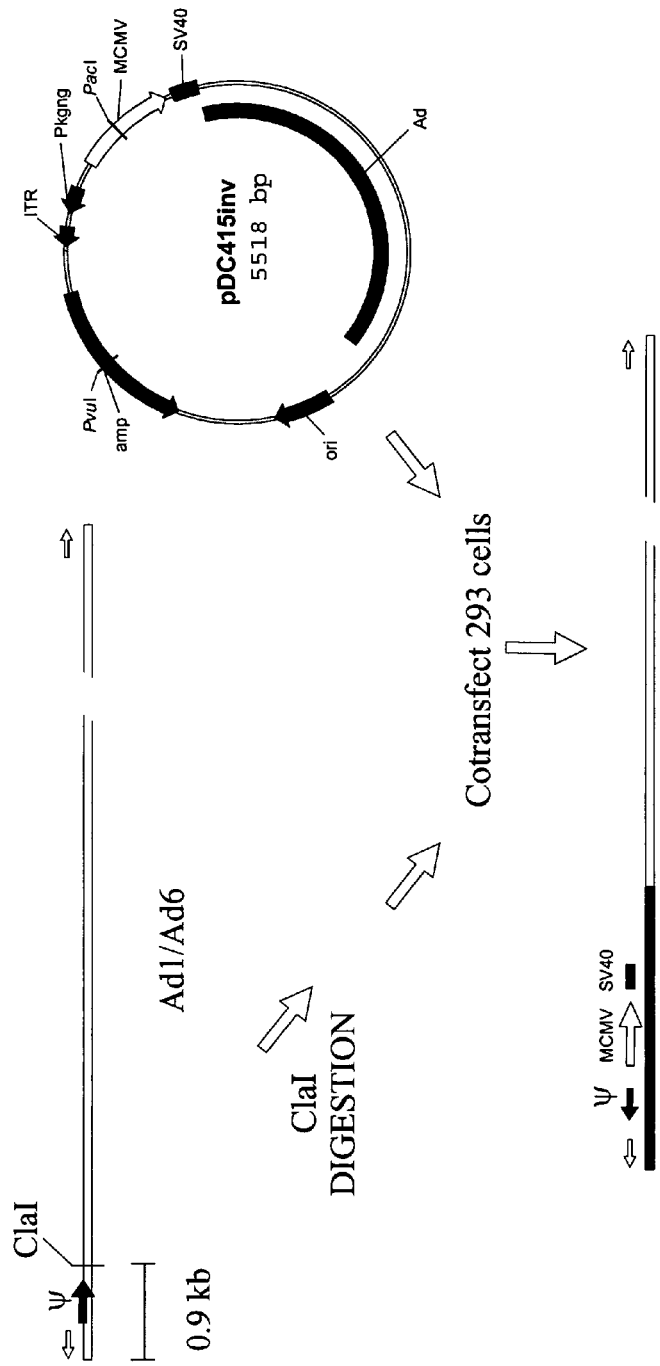

FIG. 15 illustrates a method for construction of Ad1 or Ad6 recombinant vectors with inverted packaging signals. In the example shown, pDC415inv having an inverted packaging signal is cotransfected into 293 cells with ClaI digested Ad1 or Ad6 DNA. Homologous recombination between overlapping homologous viral sequences in pDC415inv and the left end of the large fragment of ClaI digested Ad1 or Ad6 DNA results in the desired vectors.

DETAILED DESCRIPTION OF EMBODIMENTS OF THE INVENTION

In contrast to methods, systems and vectors known in the art, including those directed to reduction of RCA in virus culture, the present invention provides methods, systems, vectors, shuttle plasmids, and kits in which RCA production during recombinant adenovirus vector propagation is reduced or eliminated through use of nucleic acid sequences and recombinant adenovirus vectors that comprise a segment of DNA that effectively inverts a packaging signal in relation to an adjacent or nearby inverted terminal repeat (ITR). The nucleic acid sequences and recombinant adenovirus vectors of the present invention generally are first generation-type constructs that comprise an insert of foreign DNA in place of the early region 1 region that is deleted from first generation adenoviral vectors. An insert of foreign DNA in the early region 3 (E3), to replace an E3 deletion, is present in some embodiments to increase the extent of expressible foreign DNA, and in some embodiments as the only locus of insertion of an expression cassette (i.e., with a deletion but no insertion in E1). Other features of the various embodiments of the invention are described herein.

For example, in some embodiments of the present invention a system for production of recombinant adenoviral vectors comprises an E1 complementing cell that lacks the left ITR, and a first generation recombinant adenoviral vector comprising a deletion of E1 genes, a packaging signal inverted in relation to an adjacent or nearby ITR, and pIX as well as other non-E1 adenoviral coding sequences. In this system the vector has homology with viral sequences in the complementing cells that are to the left and right of E1 but along at least one of the homologous DNA segments the orientation is such that a homologous recombination does not give rise to viable E1+recombinant virus (i.e., RCA).

In some of the embodiments of the above-described system the sequence of DNA comprising the inverted packaging signal is oriented at the left end of the recombinant adenoviral vector nucleic acid sequence, adjacent to or near the left ITR. In other embodiments of the above-described system the sequence of DNA comprising the inverted packaging signal is oriented at the right end of the recombinant adenoviral vector nucleic acid sequence, adjacent to or near the right ITR.

As to the complementing cells, in some embodiments a complementing cell does not comprise a left ITR, and in other embodiments a complementing cell does comprise a left ITR. As to the latter embodiments, it has been learned through repeated propagation experiments that although a recombinant adenoviral vector comprising a left ITR was propagated in 293 cells (which also comprise a left ITR in the introduced adenoviral sequence), RCA were not observed during multiple successive passages of the vector in 293 cells. This surprising result provides an exception to, or disproves, a hypothesis advanced herein that RCA might be expected to appear because the vector and the viral DNA would have approximately 100 nt of homologous DNA to the left of E1 (that is, the left ITR) and ample homology to the right of E1 that would permit recombination that would rescue E1 sequences into the vector. Without being bound to a particular theory, it may be that a small homologous sequence capable of recombination, such as the approximately 100 nt in this example, is so small that recombination is inefficient.

As to recombinant adenoviral vectors of and utilized in the present invention, one recombinant adenovirus vector comprises a deletion in the E1 region from about nt 450 to about nt 3524, and in which the DNA segment from about nt 100 to about nt 450 including the packaging signal is inverted with respect to the wild type orientation.

In other embodiments of a recombinant adenoviral vector the packaging signal is translocated to the right end of the genome and inverted in orientation.

Plasmids and methods to facilitate production of adenovirus vectors that have a packaging signal in inverted orientation also are described. Embodiments of shuttle plasmids of the present invention comprise a packaging signal inverted in relation to an adjacent ITR, both of which are transferred in that orientation during a recombination with a second DNA sequence (i.e., a genomic adenoviral vector). In some of such embodiments the shuttle plasmids additionally comprise insertions of foreign DNA and in some of these latter embodiments the foreign DNA is comprised of expression cassettes for expression of nucleic acids or proteins.

Thus, the present invention provides a significant advance in the art of gene therapy, vaccine delivery and other applications of vectors in that it provides a method for production of first generation adenovirus vectors in readily available cell lines such as 293 cells without the problem of contamination with viable RCA. In part this is accomplished by inverting the DNA segment comprising the packaging signal of the recombinant adenoviral vector. While recombinant adenoviral vectors having an inverted packaging signal can be constructed in many ways the invention is exemplified with reference to two of the most popular methods of isolating Recombinant adenoviral vectors. One is homologous recombination in bacteria between a shuttle plasmid and a genomic plasmid (C. Chartier, Degryse, E; Gantzer, M; Dieterle, A; Pavirani, A; Mehtali, M Efficient generation of recombinant adenovirus vectors by homologous recombination in *Escherichia coli*. J. Virol. 70 (1996), pp. 4805–4810; Youil, R., Toner, T. J., Su, Q. and Kaslow, D. C. Rapid method for the isolation of full length adenoviral genomes by bacterial intermolecular homologous recombination. J. Virol. Methods 92: 91–97, 2001). The other is site specific recombination between a shuttle plasmid and a genomic plasmid in cotransfected mammalian host cells (Ng, P., Cummings, D. T., Evelegh, C. M. and Graham, F. L. The yeast recombinase FLP functions effectively in human cells for construction of adenovirus vectors. BioTechniques 29: 524–528, 2000; Ng, P., Parks, R. J., Cummings, D. T., Evelegh, C. M., Sankar, U. and Graham, F. L. An enhanced system for construction of adenoviral vectors by the two-plasmid rescue method. Human Gene Therapy 11: 693–699, 2000; Ng, P., Parks, R. J., Cummings, D. T., Evelegh, C. M., Sankar, U. and Graham, F. L. A high efficiency Cre/loxP based system for construction of adenoviral vectors. Human Gene Therapy 10: 2667–2672, 1999, U.S. Pat. No. 6,379,943; U.S. patent application Ser. No. 09/414,899; and U.S. patent application Ser. No. 09/978,464).

It is appreciated that isolation of adenoviral vectors by the two plasmid method can also be accomplished by homologous recombination in co-transfected host cells as described by Bett et al. (Bett, A. J., Prevec, L., and Graham, F. L. Packaging capacity and stability of human adenovirus type 5 vectors. J. Virol. 67: 5911–5921, 1993.), and in U.S. Pat. No. 6,140,087, which are specifically incorporated by reference for such method for use in conjunction with the inversion of the packaging signal as taught herein (for example see infra, Example 7 and FIGS. 14A, B exemplifying production of plasmids with inverted packaging signals). It is also appreciated that isolation of adenoviral vectors can be accomplished by homologous recombination between a plasmid and genomic viral DNA isolated from virions (as exemplified by FIG. 15 and accompanying text).

It is appreciated that the embodiments utilizing a "bacterial plasmid" or a "plasmid" are not meant to be limiting, since one skilled in the art would recognize that other types of DNA could be recombined with equal efficiency, such as by in vitro ligation or by homologous or site-specific recombination, such as through use of the Cre recombinase. For example, the Cre recombinase could be expressed in yeast cells to allow for high-efficiency recombination between yeast artificial chromosomes (YAC's) harboring an Ad genome, or, similarly, in bacteria, to allow for Cre-mediated recombination between cosmids or bacteriophage genomes harboring Ad sequences. Similarly, expression of Cre and other integrase family recombinases in mammalian cells could be used to allow for efficient recombination between two or more infectious Ad vectors, between an Ad vector and a bacterial plasmid, between an adenoviral genome and a linear DNA fragment and the like. (Ketner G, Spencer F, Tugendreich S, Connelly C, Hieter P. Efficient manipulation of the human adenovirus genome as an infectious yeast artificial chromosome clone. Proc. Natl. Acad. Sci. U.S.A. Jun. 21, 1994;91(13):6186–90, Mizuguchi H, Kay M A, Hayakawa T. In vitro ligation-based cloning of foreign DNAs into the E3 and E1 deletion regions for generation of recombinant adenovirus vectors. Biotechniques. May 2001; 30(5):1112–4, 1116.)

Accordingly, in some embodiments of the invention a mammalian cell line, such as a human cell line, that provides the Cre recombinase enzyme may be utilized. Alternatively, Cre may be provided by an Ad5 derived vector that expresses the Cre protein in suitable cells or Cre may be provided by a third plasmid encoding Cre or optionally Cre could be expressed from an expression cassette inserted into one of the two plasmids including a shuttle plasmid for use in the two plasmid rescue system. Alternatively, Cre could be expressed in other species, for example bacteria or yeast, to allow for recombination and generation of recombinant Ad genomes in said species. Alternatively, Cre could be provided as a pure or crude protein extract from expression in a variety of species for recombination of said bacterial plasmids in vitro. One skilled in the art would recognize that other recombinase systems are available which could catalyze similar recombination events in place of Cre. For example, and not meant to be limiting, the yeast FLP recombinase (also an integrase family recombinase) recognizes and recombines FRT target sites and had been shown to provide functions similar to those described herein with reference to Cre and its loxP target sites. (see Ng, P., Cummings, D. T., Evelegh, C. M. and Graham, F. L. The yeast recombinase FLP functions effectively in human cells for construction of adenovirus vectors. BioTechniques 29: 524–528, 2000). Thus, Cre/lox (using any known lox target site), FLP/FRT, and other integrase family recombinases are selected for use for recombination purposes in various embodiments of the present invention, and for making constructs used in the present invention.

For various embodiments of the present invention, a system is described for the construction of novel recombinant adenoviral vectors, or alteration of existing recombinant adenoviral vectors, by the use of recombinant DNA techniques comprising in vitro ligations, homologous recombination or site-specific recombination or combinations of these methods wherein recombinant adenoviral vectors are produced that can be propagated without the generation of RCA and the attendant inconvenience and reduced safety associated with the presence of RCA.

It will be appreciated by those skilled in the art that the present invention disclosure provides significant advances over techniques known in the art for generation, propagation and use of adenoviral vectors. First, the invention may be operated with use of readily available materials and cell lines and the methods taught herein can be easily adopted by those skilled in the art to produce recombinant adenoviral vectors that can be propagated in readily available cell lines such as 293 cells without production of contaminating RCA. Thus the methods taught herein will provide significant labor and time savings to those skilled in the art. Alternatively, the methods and systems of the present invention may be readily adapted to new cell lines, and other advances, without departing from the spirit and scope of the present invention.

In reviewing the detailed disclosure which follows, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

DEFINITIONS

First generation ("FG") adenoviral vectors (Gilardi et al., FEBS Letters 267, 60–62, 1990; Stratford-Perricaudet et al., Hum. Gene Ther. 1, 241–256, 1990; Hitt, M. M. and F. L. Graham. Adenovirus vectors for human gene therapy. In Advances in Virus Research, Vol. 55, 479_505. J. Glorioso (ed.), Academic Press, 2000; Hitt, M. M., R. J. Parks, and F. L. Graham. Structure and genetic organization of adenovirus vectors. In The Development of Human Gene Therapy, T. Friedman (ed.), Cold Spring Harbor Press, Cold Spring Harbor pp 61–86, 1998; Hitt, M., Addison, C. and Graham, F. L Human adenovirus vectors for gene transfer into mammalian cells. In: "Advances in Pharmacology—Gene Therapy" Ed. J. Thomas August, Academic Press. San Diego, Calif. 40: 137–206, 1997) are characterized by deletions of all or part of the E1A and E1B genes. E1A and E1B have transforming and transactivating properties. In addition, E1A is necessary for activating viral genes and E1B is necessary for the accumulation of viral transcripts. In some first generation adenoviral vectors, E3 also is deleted in order to increase the capacity for insertion of foreign DNA. E3 is dispensable for producing adenoviruses in cell culture. First-generation adenovirus vectors frequently are produced in 293 cells which complement the E1A and E1B deficit of the vectors. First generation adenoviral vectors that comprise expression cassettes are "recombinant adenoviral vectors."

A "helper adenovirus" or "helper virus" refers to an adenovirus which is replication-competent in a particular host cell (the host may provide Ad gene products such as E1 proteins), this replication-competent virus is used to supply in trans functions (e.g., proteins) which are lacking in a second replication-incompetent virus, identified as a helper-dependent vector; the first replication-competent virus is said to "help" the second replication-incompetent virus thereby permitting the propagation of the second viral genome in the cell containing the helper and second viruses.

Generally, a "vector" denotes a genetically engineered nucleic acid construct capable of being modified by genetic recombinant techniques to incorporate any desired foreign nucleic acid sequence, which may be used as a means to introduce said sequence in a host cell, replicate it, clone it, and/or express said nucleic acid sequence, wherein said vector comprises all the necessary sequence information to enable the vector to be replicated in host cells, and/or to enable the nucleic acid sequence to be expressed, and/or to enable recombination to take place, and/or to enable the vector to be packaged in viral particles. This recitation of the properties of a vector is not meant to be exhaustive.

The term "recombinant adenoviral vector" as used herein refers to DNA sequences comprising adenoviral DNA sequences sufficient to form a packaged vector in a suitable complementing cell, and an expression cassette comprising a desired foreign DNA sequence and appropriate DNA sequences necessary for the expression of the operably linked foreign DNA sequence in a desired host cell or organism. DNA sequences necessary for expression in prokaryotes include a promoter, optionally an operator sequence, a ribosome binding site and possibly other sequences. Eukaryotic cells are known to utilize promoters, polyadenlyation signals and enhancers. The expression may be in an isolated desired host cell or in an organism comprising suitable cells.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid sequence" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid sequence, and in particular a DNA molecule (such as indicated by the term "DNA sequence") or an RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, DNA sequences may be described herein according to the normal convention of giving only the sequence in the 5' to 3' direction along one strand of DNA. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., infra). The conditions of temperature and ionic strength determine the "stringency" of the hybridization. "Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The terms "foreign DNA" and "foreign DNA sequence" mean a DNA sequence not found in the native vector genome, and also refer to a DNA sequence from the same organism that has been translocated from its normal situs in the genome, such as by a molecular biological manipulation. A foreign DNA is introduced to a native vector genome by methods now known or later developed. Without being limiting, a foreign DNA may be comprised of an expression cassette, a cloning site sequence, or a coding sequence of a gene.

A "cloning site sequence" is a sequence comprising at least one site acted upon by enzymes known as endonucleases or recombinases, and provides for the engineering of a DNA sequence by insertion of additional DNA sequence(s) in or between such site(s) by the actions of such enzymes. A polycloning site, comprising a number of sites in excess of one, is a common type of cloning site sequence.

A DNA "coding sequence" or an "open reading frame (ORF)" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a DNA segment encoding a foreign DNA of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

A gene is generally defined as the physical and functional unit of heredity that carries information from one generation to a subsequent generation. At a molecular level for higher life forms, a gene may be defined as an entire DNA sequence, including exons, introns, and noncoding transcription control regions, that are involved in the production of a functional protein or RNA. An inserted gene is a nucleic acid sequence that provides a gene product.

The term "gene essential for replication" refers to a genetic sequence whose transcription is required for the vector to replicate in the target cell.

The term "gene product" is intended to mean DNA, RNA, protein, peptides, or viral particles.

As used herein, the term "gene of interest" refers to an inserted gene in a vector or plasmid whose expression is desired in a host cell. Genes of interest include genes having therapeutic value as well as reporter genes. A variety of such genes are contemplated, including but not limited to genes of interest encoding a protein which provides a therapeutic function.

The term "genetic cassette" as used herein refers to a fragment or segment of DNA containing a particular grouping of genetic elements. The cassette can be removed and inserted into a vector or plasmid as a single unit. The term "expression cassette" as used herein refers to a fragment or segment of DNA wherein the particular group of elements comprises a sequence encoding for a polypeptide, an RNA sequence, or other desired molecular products, together with other operably linked elements, such as a promoter and a stop sequence (i.e., a polyadenylation signal), that provides for translation of the coding sequence upon integration into an appropriate larger DNA sequence, for instance an adenoviral vector (i.e., to help form a recombinant adenoviral vector). An expression cassette may be engineered to provide for two or more coding sequences under the control of one or more promoters to provide bicistronic or polycistronic constructs.

The terms "in operable combination", "in operable order" and "operably linked" as used herein refer to the linkage of nucleic acid sequences in such a manner that a nucleic acid molecule capable of directing the transcription of a given gene, RNA sequence (such as an siRNA), and/or the synthesis of a desired protein molecule is produced. The term also refers to the linkage of amino acid sequences in such a manner so that a functional protein is produced.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "enhancer" is used according to its art-recognized meaning. It is intended to mean a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

The term "oligonucleotide" as used herein is defined as a molecule comprised of two or more deoxyribonucleotides or ribonucleotides, usually more than three (3), and typically more than ten (10) and up to one hundred (100) or more (although often between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art.

The term "probe" as used herein refers to a labeled oligonucleotide which forms a duplex structure with a sequence in another nucleic acid, due to complementarity of at least one sequence in the probe with a sequence in the other nucleic acid.

As used herein the terms "nucleic acid segment" and "segment of DNA" are intended to indicate any nucleic acid molecule of cDNA, genomic DNA, synthetic DNA or RNA origin. The term "segment" is intended to indicate a nucleic acid segment which may be single- or double-stranded, and which may be based on a complete or partial naturally occurring nucleotide sequence encoding a polypeptide of interest. A "segment" may be comprised of a combination of nucleic acid segments of diverse origin.

The vectors of the present invention commonly contain one or more selectable markers which permit easy selection of transformed cells. A selectable marker is a gene the product of which provides for biocide or viral resistance, resistance to heavy metals, prototrophy to auxotrophs, and the like.

Antibiotic selectable markers confer antibiotic resistance to such antibiotics as ampicillin, kanamycin, chloramphenicol, tetracycline, neomycin, hygromycin or methotrexate. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygb (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. For use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The term "host cell" encompasses any progeny of a parent cell which is not identical to the parent cell due to mutations that occur during replication.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives are also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers to proteins and polypeptides encoded by other nucleic acids (e.g., non-coding and regulatory RNAs such as tRNA, sRNPs), as well as to RNA sequences, such as siRNAs. The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, Genomics 4: 560–569 (1989); Landren et al., Proc. Natl. Acad. Sci. 87: 8923–8927 (1990); Barany, F., Proc. Natl. Acad. Sci. 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperature permits the ligation reaction to be conducted with high stringency (Barany, F., PCR Methods and Applications 1:5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984). See, also, Ausubel et al., Current Protocols in Molecular Biology, John Wiley and Sons, Baltimore, Md. (1989); Hitt et al, "Construction and propagation of human adenovirus vectors," in Cell Biology: A Laboratory Handbook, Ed. J. E. Celis., Academic Press, 2nd Edition, Volume 1, pp: 500–512, 1998; Hitt et al, "Techniques for human adenovirus vector construction and characterization," in Methods in Molecular Genetics, Ed. K. W. Adolph, Academic Press, Orlando, Fla., Volume 7B, pp:12–30, 1995; Hitt, et al., "Construction and propagation of human adenovirus vectors," in Cell Biology: A Laboratory Handbook," Ed. J. E. Celis. Academic Press. pp: 479–490, 1994. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The foreign DNA sequences are expressed in hosts after the sequences have been operably linked to an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

*E. Coli* is one prokaryotic host useful particularly for cloning DNA sequences of the present invention. Other microbial hosts suitable for use include *bacilli*, such as *Bacillus subtilus*, and other enterobacteriaceae, such as *Salmonella, Serratia*, and various *Pseudomonas* species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. *Saccharomyces* is a suitable host, with suitable vectors having expression control sequences, such a promoters, including 3-phosphoglycerate kinase or other glycolytic enzymes, and an origin of replication, termination sequences, etc. as desired.

In addition to microorganisms, mammalian tissue cell culture is used to express and produce the polypeptides in accordance with the present invention. Eukaryotic cells are readily utilizable, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Commonly used expression control sequences are promoters derived from immunoglobin genes, SV40, Adenovirus, Bovine Papilloma Virus, Herpes Virus, Cytomegalovirus and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation or lipofection are useful for other cellular hosts.

As discussed above, for viral DNA replication and packaging of viral DNA into virion particles, only three regions of the viral DNA are known to be required in cis. These are the left inverted terminal repeat, or ITR, (bp 1 to approximately 103 for Ad5) the packaging signals (approximately 194 to 358 bp for Ad5) (Hearing and Shenk, 1983, Cell 33:

695–703; Grable and Hearing 1992, J. Virol. 64: 2047–2056) and the right ITR. Among the regions of the viral genome that encode proteins that function in trans, two have been most important in the design and development of adenovirus vectors. These are early region 3 (E3) located between approximately 76 and 86 mu (mu=% distance from the left end of the conventionally oriented genome) and early region 1 (E1) located between approximately 1 and 11 mu. E3 sequences have long been known to be nonessential for virus replication in cultured cells and many viral vectors have deletions of E3 sequences so that the capacity of the resulting vector backbone for insertion of foreign DNA is thereby increased significantly over that allowable by the wild-type virus (Bett, A. J., Prevec, L., and Graham, F. L. Packaging capacity and stability of human adenovirus type 5 vectors. J. Virol. 67: 5911–5921, 1993.). E1 encodes essential functions. However, E1 can also be deleted, providing that the resulting virus is propagated in host cells, such as the 293 cell line, PER-C6 cells, 911 cells, and the like, which contain and express E1 genes and can complement the deficiency of E1(–) viruses.

In addition, as disclosed herein, we have unexpectedly found that inversion of the packaging signal in FG vectors markedly reduces the frequency of generation of RCA even when said vectors are propagated in 293 cells which contain the left end of the Ad genome from nt 1 to nt 4344. Thus inversion of the packaging signal provides a novel, useful and very simple means to avoid the problem of RCA contamination in vector preparations to be used for research or in clinical applications. As used herein, inversion of a packaging signal is taken to mean arranging, such as by molecular biological manipulations, a sequence comprising the packaging signal (or a portion of it sufficient to achieve a desired level of packaging of the vector so produced) so that the orientation of the packaging signal (or the portion of it) is opposite of its normal orientation along the adenoviral DNA sequence in relation to the nearest of the left ITR and the right ITR. Such an arrangement has been found to still provide for packaging functions by the inverted packaging signal, but, advantageously, as noted, has been found to alter the occurrence of RCA during propagation of recombinant adenoviral vectors comprising such inverted packaging signal. Also, as recognized in the prior art, for a packaging signal sequence to be functional as a packaging signal, to provide for packaging, it should be positioned within about 600 nt of either the left ITR or the right ITR.

The methods provided herein for design and production of recombinant adenoviral vectors are a significant improvement over and are significantly different from previously described methods that rely on use of vectors that can recombine with viral DNA sequences present in the complementing E1 positive host cells resulting in contamination of vector preparations with RCA. The methods described are also a great improvement over systems that rely on matched cell-vector combinations with no overlap because of the great expense of such systems, their lack of general availability, and the inconvenience of using cell lines that are not readily available.

A component of some embodiments of the invention is the use of isolated human cells, such as 293 cells or other cells that may be deemed suitable in that they support the replication of the viral components of the invention, that express Cre recombinase and that can be transfected with the plasmids described herein and in the examples which follow, to generate a virus containing the desired modifications such as an insertion of foreign DNA or a modified fiber gene. It will be appreciated by those skilled in the art that the requisite cell lines can be generated by transfecting 293 cells or other cells, with a plasmid comprising the coding sequences for Cre under the control of suitable regulatory sequences, including a promoter and polyadenylation signal and containing, in addition, a selectable gene encoding, for example, resistance to G418 or histidinol. A person skilled in the art can readily obtain drug resistant cells that express the Cre recombinase in addition to the drug resistance gene used for selection. It will also be appreciated by one skilled in the art, based on the present disclosure, that host cells can also be induced to transiently express a recombinase by transfection with a plasmid comprising an expression cassette containing said recombinase gene or by infection with a viral vector that expresses the recombinase. Thus the example of 293Cre cells or other permanently transformed recombinase expressing cell lines is not meant to be limiting.

As indicated above, the use of Cre recombinase in the disclosure and examples is not meant to be limiting as a person skilled in the art will readily appreciate that other enzymes capable of catalyzing site-specific recombination between DNA sequences recognized by said enzymes could equally be employed in place of the Cre recombinase. An example, not meant to be limiting, of such an enzyme that could be substituted for Cre is the "FLP" recombinase of yeast in combination with its target site FRT (O'Gorman et al. Science 251, 1351, 1991). More generally, any integrase family recombinase may be used in place of Cre recombinase (See Kornberg & Baker (DNA Replication, Chapter 21–6, pp 806–817, W. H. Freeman, NY $2^{nd}$ Edition, 1992; and Kilby, N. J., M. R. Snaith, and J. A. H. Murray. 1993. Site-specific recombinases: tools for genome engineering. Trends Genet. 9: 413–421).

The following examples are provided to further disclose the genesis, operation, scope and uses of embodiments of the present invention. These examples are meant to be instructive, and illustrative, and not to be limiting as to the scope of invention as claimed herein. These examples are to be considered with the referred to drawings.

EXAMPLE 1

In order to better appreciate and understand the reasoning that led to the identification of the problem and to the conception and reduction to practice of the present invention, it is useful to describe earlier laboratory efforts to reduce the levels of contaminating RCA in FG Recombinant adenoviral vector preparations. First, it is noted that it is theoretically possible to rescue a functional E1+virus following a single recombination event between vector and 293 cell DNA sequences rightward of E1 followed by a repair process involving annealing of left viral ITR integrated in the 293 cell genome and the right ITR of the vector by a process elucidated by Lippe and Graham (Lippe, R. and Graham, F. L. Adenoviruses with non-identical terminal sequences are viable. J. Virol. 63: 5133–5141, 1989). However, Hehir et al. showed that RCA formation appears to result from two recombination events on either side of the E1 region (Hehir, K. M., Armentano, D., Cardoza, L. M., Choquette, T. L., Berthelette, P. B., White, G. A., Couture, L. A., Everton, M. B., Keegan, J., Martin, J. M., Pratt, D. A., Smith, M. P., Smith, A. E. and Wadsworth, S. C. (1996). This process is diagrammed in FIG. 2 where the bold, vertically oriented curved lines represent possible recombination events which presumably could occur anywhere in the two regions of overlap.

Figure 1:
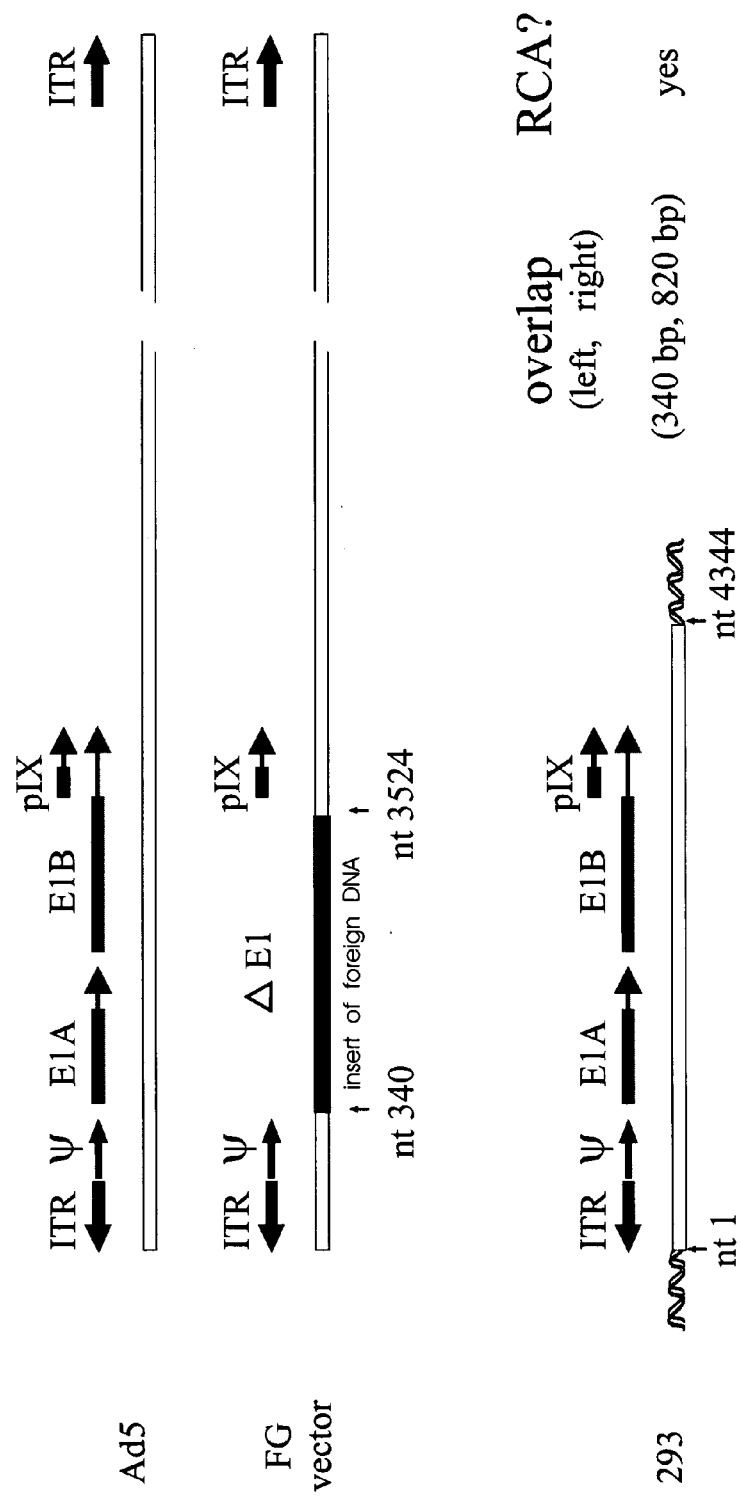
FIG. 1 is a diagrammatic representation summarizing the sequence similarities that are believed to lead to generation of replication competent adenoviruses (RCA) that are generated during propagation of first generation (FG) adenovirus vectors. Vectors propagated in typical complementing cells such as 293 cells usually become contaminated with RCA after multiple passages. The E1 deletion shown for the illustrated FG vector is one of the largest deletions commonly employed in Recombinant adenoviral vectors and was developed in the inventor's laboratory (Bett, A. J., Haddara, W., Prevec, L. and Graham, F. L. An efficient and flexible system for construction of adenovirus vectors with insertions or deletions in early regions 1 and 3. Proc. Natl. Acad. Sci. US 91: 8802–8806, 1994). Many FG vectors have been developed that have somewhat smaller E1 deletions often extending from about nt 450 to about nt 3300 and these consequently have even greater overlap with the Ad5 sequences of 293 cells than that shown at the bottom of FIG. 1.
Figure 2:
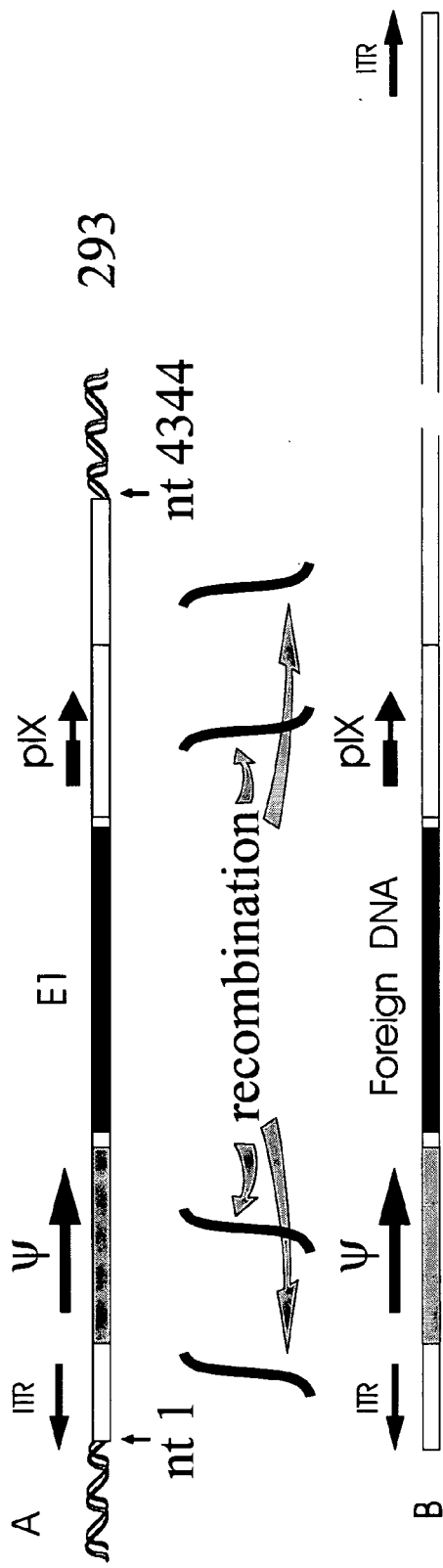
FIG. 2 illustrates a mechanism of formation of RCA by homologous recombination. All FG vectors contain sequences flanking the foreign DNA insert in the E1 region that are homologous to the viral DNA sequences in 293 cells flanking the complementing E1 genes. This is because the left ITR and packaging signal (both cis acting sequences that are needed for Ad DNA replication and DNA packaging into virions) must be retained in the Ad DNA for virus viability. On the right side of the E1 deletion, the pIX gene minimally is almost always present in the vector backbone because pIX is required for virion stability and for packaging of full length viral DNA into infections virions (Ghosh Choudhury, G., Haj-Ahmad, Y., and Graham, F. L. Protein IX, a minor component of the human adenovirus capsid, is essential for the packaging of full-length genomes. The EMBO J. 6: 1733–1739, 1987.) Consequently recombination can occur on each side of the foreign DNA resulting in a vector that now contains a functional E1 region (RCA).
Figure 3A:
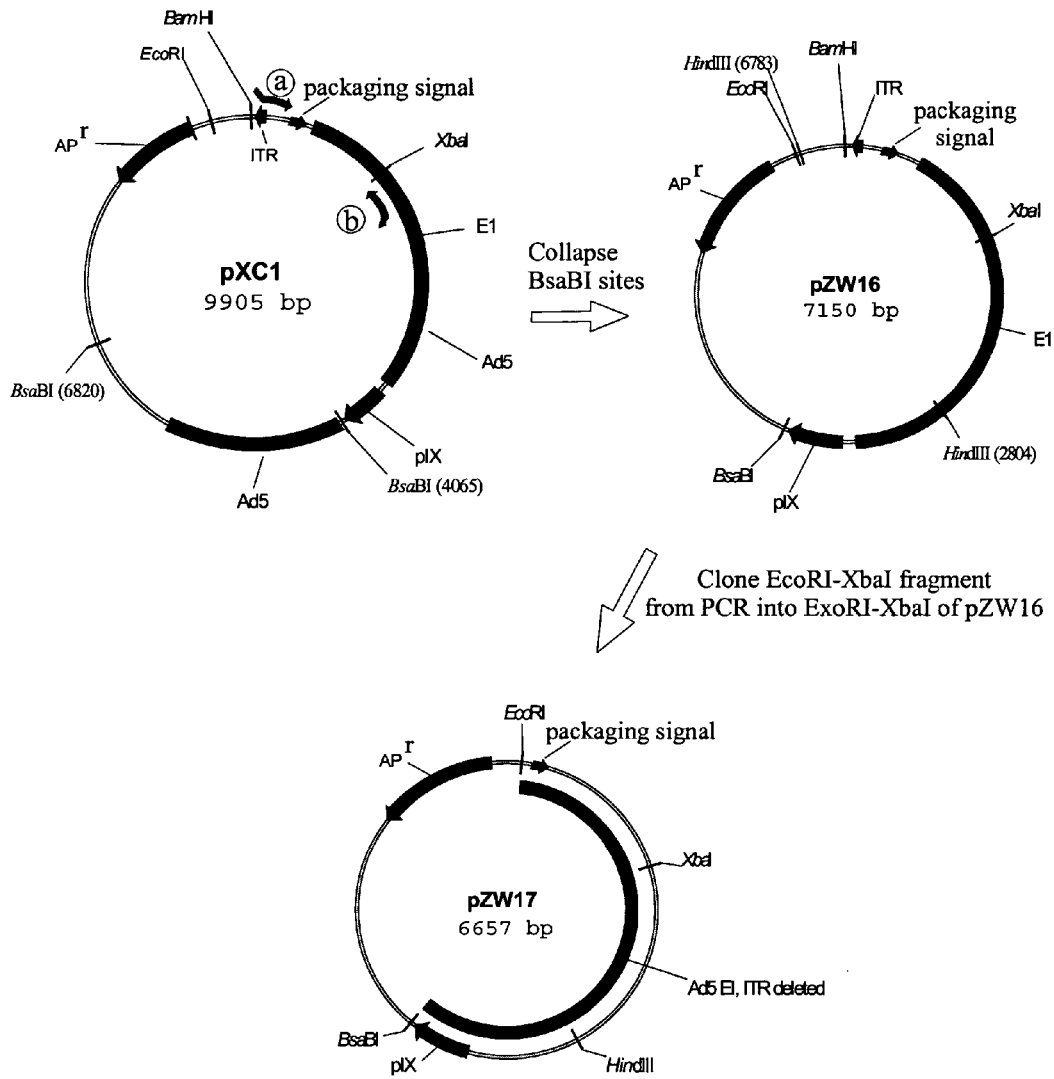
FIGS. 3A–B diagrammatically illustrate plasmids, oligonucleotides, and DNA sequences that were involved in an early attempt to reduce the frequency of RCA generation by reducing the amount of overlap on either side of the foreign DNA.
Figure 3B:
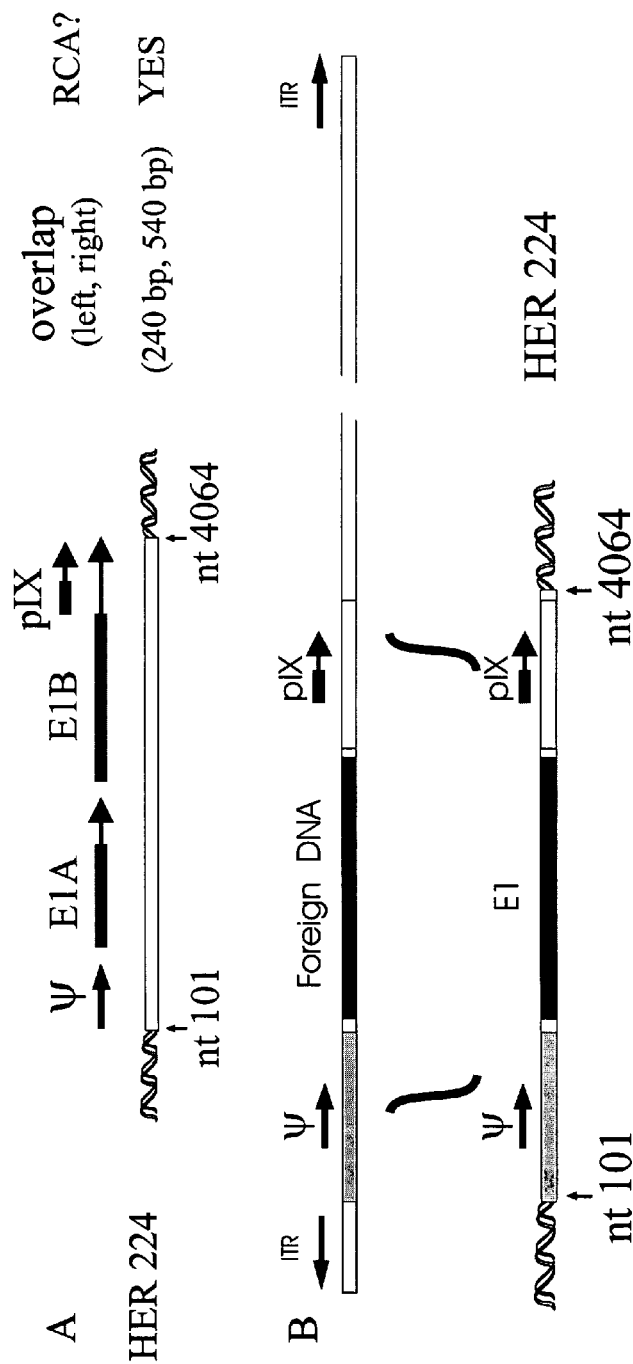

Since RCA production seems to depend on the presence of viral DNA sequences to left and to right of the foreign DNA inserted in FG vectors that recombine with homologous sequences in the complementing host cell (FIGS. 1 and 2) it was hypothesized that by reducing the extent of overlap one would reduce the recombination frequency and thereby decrease the formation of RCA. Therefore, toward the goal of reducing overlap, new cell lines were isolated that express Ad E1 but have less overlap to left and right of E1 than the sequences that are present in 293 cells. Thus a plasmid was constructed, pZW17, that has left end Ad sequences starting at nt 101 and extending to nt 4064 (FIG. 3). The first step was to reduce the overlap at the right of E1. This was done by digestion of pXC1 (Microbix Biosystems Inc.) with BsaB1 and religation to delete Ad5 sequences downstream of the pIX gene to generate pZW16. Next a PCR reaction was carried out using oligonucleotides a (SEQ ID NO:1) and b (SEQ ID NO:2) shown at the bottom of FIG. 3A and the PCR product was digested with EcoR1 and XbaI and cloned between the EcoR1-XbaI sites of pZW16. This created pZW17 which comprises Ad5 nucleotides 101 to 4064 and therefore lacks the left ITR and lacks Ad sequences rightward of pIX. PZW17 was then used to transform primary human embryo retinal cells or primary human embryo kidney cells generally following the procedure described in Graham, F. L., and van der Eb, A. J. Transformation of rat cells by DNA of human adenovirus 5. Virology 54, 536–539, 1973, and Graham, F. L., Smiley, J., Russell, W. C., and Nairn, R. Characteristics of a human cell line transformed by DNA from human adenovirus type 5. J. Gen. Virol. 36, 59–72, 1977, to produce cell lines that contain and express Ad E1 functions. The viral DNA structure, in an example of one such cell line, HER224, is shown in FIG. 3B. As can be seen from comparison with FIG. 1, the overlap to the left of E1 is reduced from 340 bp to 240 bp and the overlap to the right from 820 bp to 540 bp. Unfortunately, experiments to detect RCA in vector preparations grown in HER224 cells indicated that RCA were still readily produced. It was concluded that this reduction of the overlap was insufficient to affect the efficiency of homologous recombination as illustrated in FIG. 3B, panel B, wherein recombination is assumed to occur within homologous sequences comprising the packaging signal of the virus. Nonetheless, the production of the HER224 cell line comprising the adenoviral DNA from pZW17, which lacked the left ITR, proved valuable in later efforts. Other cell lines were similarly derived by transforming primary human cells with pZW17. For example primary human embryo kidney cells were transformed to produce E1+ cell lines, among them HEK218C10 and HEK218C20 (mentioned in Shaw, G., Morse, S., Ararat, M. and Graham, F. L. Preferential transformation of human neuronal cells by human adenoviruses and the origins of HEK 293 cells. FASEB J., 16: 869_871, 2002.).

EXAMPLE 2

Considering the data from Example 1, and considering the two-recombination-events hypothesis of RCA formation, further consideration of panel B of FIG. 3B lead to conception of a possible solution to the problem of RCA formation in virus preparations grown in HER224 cells. If the packaging signal (and adjacent adenoviral nucleotides up to the inserted foreign DNA in E1) in the Recombinant adenoviral vector genome were moved to the right end of the genome, where it is known that it can function as a packaging signal in such position, then there would be no left end homologous sequence recombinable with the DNA of adenoviral sequences introduced into the HER224 cells to provide E1 functions, and recombination as illustrated in panel B should be impossible. Therefore, a series of plasmids were constructed as shown in FIGS. 4A to 4F, which culminated in shuttle plasmids that could be combined with an Ad genomic plasmid, pBHGfit(del)E1,3FLP, via the action of the site specific recombinase FLP, to produce an infectious recombinant adenoviral vector expressing LacZ and having a packaging signal at the right end of the viral genome. In FIG. 4A are illustrated the first steps in this cloning procedure. First ExoIII-S1 digestion as described in Heyneker et al. (1974) was used to remove the terminal 131 nt from the ends of Ad5 DNA. The right Xba1 C fragment comprising nts 30471 to 35804 was then cloned into the Xba1-StuI site of pDC512 (Microbix Biosystems Inc.) to create pDC512AdXbaC containing the right approximately 5.4 Kb of Ad 5 DNA except the terminal 131 nt. This plasmid was then digested with AatII and XbaI and the intervening region removed by ligation after creating blunt ends to produce pDC512XbaCDel which contains the right end of Ad5 minus the terminal 131 nt. FIG. 4B illustrates the construction of a plasmid containing an ITR junction and packaging signal. A Cac8I fragment comprising the ITR junction and packaging signal of pDC316 (Microbix Biosystems Inc.) was cloned into the SmaI site of pUC19. Subsequently extraneous sequences were removed by collapsing from SstI to SstII to create pUCITRjuncpackag. As illustrated in FIG. 4C the DNA segment comprising the ITR junction and packaging signal was further reduced in size by digestion with MseI, treatment with the Klenow fragment of DNA polymerase I, digestion with EcoRI and insertion of the resulting fragment into the EcoRI-SmaI site of pUC19 to create pUCITRPack2. The EcoRI-BamHI segment of pUCITRPack2 comprising the packaging signal and ITR junction was then transferred into the EcoRI-BamHI site of pDC512XbaCDel to generate pFG189-4 (FIG. 4D) which contains in the following order clockwise from twelve o'clock: the right end of Ad5 except for the terminal 131 nt, the packaging signal, an ITR junction and an frt site. As illustrated in FIG. 4E, pFG189-4 was reduced in size by collapsing (after appropriate treatment of DNA ends for ligation) from EagI to either StuI, to AccI, to HindIII or to SmaI to produce plasmids pFG190D1, pFG190D2, pFG190D3 or pFG190D4 respectively. These latter plasmids were then used as recipients of an expression cassette derived from pCA17 (Microbix Biosystems Inc.) comprising the HCMV IE gene promoter, the LacZ coding sequences, and SV40 poly adenylation signal as illustrated in FIG. 4F for pFG190D4 and its daughter plasmid pFG190D4LacZ. Finally the plasmids pFG190D1,2,3, 4LacZ were used in cotransfections of 293 cells or HER224 cells along with pBHGfrt(del)E1,3FLP (Microbix Biosystems Inc.) to generate, by recombination, the vector AdFG190LacZ containing a LacZ expression cassette at the left end, and a packaging signal at the right end (FIG. 4G). It should be mentioned that all 4 plasmids of the pFG190DLacZ series were equally proficient at generating virus and identical viruses are produced from all 4 shuttle plasmids (the left end of the vector, designated AdFG190LacZ, is shown at the bottom of FIG. 4G).

The likely mechanism by which the vector is generated is illustrated in FIG. 4H and involves both site specific recombination between frt sites catalyzed by FLP and homologous recombination between viral DNA sequences at the right end of the viral genome. The resulting vector, AdFG190LacZ was grown in HER224 cells, and tested after numerous passages for the presence of RCA. Surprisingly, and disappointingly, it was discovered that RCA were still readily produced when the vector was propagated in HER224 cells.

To understand how this could occur numerous models were considered until the scheme illustrated in FIG. 5 was formulated. It is proposed that a first homologous recombination event occurs between overlapping viral sequences present to the right of E1 in HER224 cells and to the right of the foreign DNA cassette in the vector (homologous sequences essentially comprising the pIX gene) to generate the intermediate illustrated in FIG. 5, panel C. This intermediate can then undergo a second, intramolecular recombination (or intermolecular recombination with a second molecule of the form shown in panel C) as illustrated in FIG. 5, panel D to generate a vector with a packaging signal at both ends of the viral genome and containing an intact E1 region, hence replication competent in cells that do not express E1. A prediction of the model mechanism shown in FIG. 5 is that the RCA contaminating the vector preparations would have a packaging signal at both ends of the genome (FIG. 6) and this was confirmed by restriction enzyme digestion and gel electrophoretic analysis of isolated RCA genomes. Thus without being bound to a particular theory, the mechanism illustrated in FIG. 5 is a highly likely explanation for how RCA arise. With hindsight, it might have been predictable that such a sequence of recombination events could occur and that the process could be quite efficient since, like the mechanism for RCA generation illustrated in FIG. 2, the process illustrated in FIG. 5 requires only 2 recombination events, both of which are highly similar to the recombinations presumed to occur during growth of a standard FG vector in 293 cells or HER224 cells.

EXAMPLE 3

During study of various models of recombination to explain the production of RCA in AdFG190LacZ vector preparations grown in HER224 cells, the inventor arrived at a primary conception of the present invention. For close examination of panel D of FIG. 5 reveals that if the packaging signal at the right end of the vector genome had been inverted with respect to its normal orientation (relative to the adjacent, right ITR), the recombination event illustrated in FIG. 5D could not occur and the intermediate shown in FIG. 5C would not be packageable.

FIG. 7A thus illustrates a possible solution to the problem of RCA formation based on the above conception and reasoning. Inversion of the packaging signal relative to its normal orientation with respect to the viral DNA terminus (ITR) in the vectors constructed in the experiments described in FIG. 4 would block the second recombination event needed to produce viable RCA in vector preparations grown in HER224 cells as shown in FIG. 7A, panel D. Indeed it is well known that the packaging signal of Ads functions perfectly well in inverted orientation, and that it can function at the left or right end of the genome equally well (Hearing, P., Samulski, T. J., Wishart, W. L. and Shenk, T. Identification of a repeated sequence element required for efficient encapsidation of the adenovirus type 5 chromosome. J. Virol. 61, 2555–2558, 1987). Therefore a vector with the structure shown in FIG. 7A, panel B could be readily constructed and would be viable and would be predicted not to produce RCA following growth in HER224 cells. (It is important to point out that the use of HER224 cells here and in the following sections is not meant to be limiting as 911 cells, that also lack the left ITR or other human cells transformed by pZW17 such as HEK218C10 and C20 or cells transformed by similar plasmids, could as easily be used in the present invention.)

It should be noted that inversion of the packaging signal in this example prevents the homologous recombination illustrated in FIG. 5D but does not prevent homologous recombination per se. For example a recombination event of the type illustrated in FIG. 7B should be possible, but importantly, the DNA product of recombination would not be packageable into viable virus. Thus the strategy for prevention of RCA taught in the above and in following examples does not depend on elimination of all overlap between cellular and vector DNA sequences on both sides of the E1 region. Rather, the strategy depends on the orientation of the sequences, and in particular the orientation of the packaging signal, or the packaging signal and nucleotides adjacent to it to the left (5') of the E1 deletion or inserted foreign DNA at the E1 region.

FIG. 8 illustrates a strategy for constructing a vector with an inverted packaging signal at the right end of the genome. In FIG. 8A the first step is outlined. A PCR reaction is performed on pFG190D4 using oligonucleotides that anneal just inside the DNA segment containing the packaging segment and that contain about 60 nt of sequences that are homologous to the flanking ITR sequences or homologous to the flanking Ad5 right end sequences. In the next step (FIG. 8B) the PCR product is recombined with pFG190D4 DNA that first is digested with one or more of EcoRI, ApaI or BsrGI that cut near or within the packaging segment. Homologous recombination in BJ5183 cells (C. Chartier, Degryse, E; Gantzer, M; Dieterle, A; Pavirani, A; Mehtali, M Efficient generation of recombinant adenovirus vectors by homologous recombination in *Escherichia coli*. J. Virol. 70 (1996), pp. 4805–4810.) between the 60 or so nt from the 5' portions of the oligonucleotides and the homologous sequences flanking the packaging signal in pFG190D4 results in reinsertion of the packaging signal into pFG190D4 but in inverted orientation. The resulting shuttle then is used for insertion of a foreign DNA such as the LacZ expression cassette illustrated in FIG. 4F as described above, or other foreign nucleic acids, and finally rescued into virus as described in FIGS. 4G and 4H. This strategy is straightforward and is predicted to result in a vector that could be propagated in HER224 cells or similar host cells without generation of RCA. Other approaches could easily be designed for inversion of the packaging signal in pFG190D4 or similar plasmids and their rescue into virus since the skill in the art of manipulation of DNA by recombinant methods is very high.

However, an even simpler approach presents itself once one is lead to the idea of inverting the packaging signal in Recombinant adenoviral vectors to prevent the formation of RCA when the vector is propagated in HER224 cells. For inversion of the packaging signal when it is located at the left end of a standard FG vector is also predicted to prevent the second of the two recombination events that appear to be needed to generate RCA from such vectors. Thus this simpler approach is illustrated in FIG. 9 which shows that while a single recombination event between the homologous sequences common to cells and virus on the right side of E1 and the foreign gene insert can still take place, the second recombination event involving homologous sequences on the left side is blocked if the homologous sequences represented by the packaging signal are in opposite orientations relative to each other_(FIG. 9, panel C). It is noteworthy that this block to recombination is only expected to be completely effective in HER224 cells (or similar cells) since in 293 cells there would still be approximately 100 bp of overlap at the left end of the vector genome comprising the left ITR which might be adequate for homologous recombination.

EXAMPLE 4

To test the hypothesis put forward above that inversion of the packaging signal at the left end in FG recombinant adenoviral vectors should allow production of RCA free vectors when these are grown in HER224 cells, a number of shuttle plasmids and viral vectors were constructed in which the packaging signal was inverted relative to its normal orientation. FIG. 10 illustrates the first strategy used to construct FG recombinant adenoviral vectors with an inverted packaging signal. One PCR reaction was carried out with pDC516(io) (Microbix Biosystems) using oligonucleotides 3 (SEQ ID NO:5)and 4 (SEQ ID NO:6)shown in FIG. 10B to amplify a DNA segment comprising the packaging signal flanked by MluI and SpeI restriction sites and a second PCR reaction was carried out using oligonucleotides 1 (SEQ ID NO:3) and 2 (SEQ ID NO:4) with pDCMH4cLox(Ad del) to amplify a DNA segment comprising the entire shuttle plasmid but lacking the packaging signal and having at the ends MluI and SpeI sites (FIG. 10A). Ligation of the two PCR products after digestion with MluI and SpeI resulted in the plasmid pDCMH4LoxPkginv which comprises a left ITR, a packaging signal in inverted orientation with respect to the left end, an MCMV IE gene promoter, polycloning sites, an SV40 polyadenylation signal, and a loxP site. This shuttle plasmid can be used in cotransfections (FIG. 10C) of 293 cells or HER224 cells or other host cells expressing E1 along with pBHGloxDelE1, 3Cre (Microbix Biosystems) to generate a defective (E1 deleted) viral vector containing an inverted packaging signal and a cassette comprising the MCMV promoter and SV40 poly A. Numerous viruses were obtained and characterized by restriction enzyme digestion and gel electrophoresis to confirm that they had the expected structure, and one, designated AdMCMVPkginv, was chosen for further work.

It was expected that it should be possible to grow AdMCMVPkginv for multiple passages in HER224 cells without production of RCA since, as diagramed in FIG. 9, HER224 cells lack DNA sequences at the left of E1 that could recombine with the extreme left end sequences of AdMCMVPkginv in such a way as to form a viable E1+virus. In contrast 293 cells and AdMCMVPkginv both contain the left ITR comprising approximately 100 bp in common that might be sufficient for the second recombination event that is thought to generate RCA as illustrated in FIG. 2. Therefore AdMCMVPkginv was serially passaged on both cell lines, the 293 passages intended to serve as a positive control for RCA production. A totally unexpected result was obtained from this experiment: not only did AdMCMVPkginv fail to produce RCA after being serially passaged in HER224 cells but extensive passaging in 293 cells (over 35 passages) also failed to result in the appearance of RCA. Since it was unusual for RCA not to appear following such extensive passaging of a FG Recombinant adenoviral vector in 293 cells this observation required confirmation and further study.

EXAMPLE 5

Since the vector illustrated in the bottom of FIG. 10C contains a promoter and poly A signal but not a cDNA it was possible that the virus had some special property, unrelated to the orientation of the packaging signal, that resulted in its being capable of propagation in 293 cells without production of RCA. For example it was possible that the MCMV-polyA sequences conferred some growth advantage on the vector relative to E1 positive derivatives lacking these sequences. Extensive experience with Recombinant adenoviral vectors in the inventor's laboratory had shown that essentially in every case in which a FG vector was constructed comprising an expression cassette that drove high level expression of a protein, RCA was detectable after a few passages in 293 cells. Therefore, a second vector with inverted packaging signal was made comprising an expression cassette containing the HCMV E gene promoter driving LacZ expression. The construction of this vector is illustrated in FIG. 1A. The MCMV promoter in pDCMH4LoxPkginv was removed by MluI and EcoRI digestion, treatment with Klenow, and ligation to produce pDCMH4LoxPkginvdelta. The LacZ coding sequences along with an upstream HCMV promoter were then excised from pCA17 (Microbix Biosystems Inc.) by BglII and SalI digestion and inserted into the BamHI-SalI site of pDCMH4LoxPkginvdelta to produce pHCMVLacZ-PkginvLox. By cotransfection with pBHGloxDelE1,3Cre (Microbix Biosystems Inc.) as illustrated in FIG. 10C, the LacZ expression cassette and inverted packaging signal were rescued into a vector which was designated AdHCM-VLacZPkginv. Once again the structure of the rescued vector was confirmed by restriction enzyme digestion and gel electrophoresis and LacZ expression was confirmed by addition of X-Gal to the infected cells.

Three different plaque isolates of AdHCMVLacZPkginv, identified as 5.1, 5.2 and 5.3, were serially passaged in 293 cells and in HER224 cells. Once again, surprisingly, no RCA were detectable after several passages even in 293 cells. An example analysis of viral DNA structure from up to 10 passages in 293 is shown in FIG. 11B. The HindIII digestion pattern was that predicted for AdHCMVLacZPkginv and no DNA bands were detectable in the regions predicted for fragments derived from E1+ RCA, indicated by black arrows.

EXAMPLE 6

To test the generality of the observations described above obtained with two FG vectors, one containing a promoter and polyA signal but no coding sequence, the other containing a LacZ expression cassette, another vector was independently constructed that also had an inverted packaging signal but had an expression cassette for production of EGFP (green fluorescent protein). Two strategies were designed for construction and rescue of the vector. In the scheme outlined in FIG. 12, homologous recombination in *E. coli* strain BJ5183 (C. Chartier, Degryse, E; Gantzer, M; Dieterle, A; Pavirani, A; Mehtali, M Efficient generation of recombinant adenovirus vectors by homologous recombination in *Escherichia coli*. J. Virol. 70 (1996), pp. 4805–4810.) was used to invert the packaging signal. As illustrated in FIG. 12A the packaging signal was amplified by PCR using oligonucleotides 7 (SEQ ID NO:7) and 8 (SEQ ID NO:8) shown in FIG. 12C using DNA from polyMRKCMVEGFP, a plasmid that contains the left end of Ad5 with an EGFP expression cassette in place of E1. PolyMRKCMVEGFP (S. Colloca, IRBM, unpublished) was constructed by insertion of an EGFP expression cassette (Clontech) into a shuttle plasmid designated as MRKAd5 described by (Youil R, Toner T J, Su Q, Casimiro D, Shiver J W, Chen L, Bett A J, Rogers B M, Burden E C, Tang A, Chen M, Emini E A, Kaslow D C, Aunins J G, Altaras N E Hum Gene Ther. July 1, 2003; 14(10):1017–34. Comparative analysis of the effects of packaging signal, transgene orientation, promoters, polyadenylation signals, and E3 region on growth properties of first-generation adenoviruses). The oligonucleotides were designed to contain 5' nucleotides that were homologous to 62 nt of HCMV DNA and 60 nt of Ad ITR sequences and were designed such that by homologous recombination with SgrAI cleaved polyMRKCMVEGFP DNA (FIG. 12B) the packaging signal would be reinserted into polyMRKCMVEGFP in inverted orientation. As is detailed later, the resulting plasmid, pMRKpkgn inv can be recombined with a genomic Ad5 plasmid that can then be transfected into E1 complementing host cells to generate the desired vector.

In yet another strategy, illustrated in FIG. 13, two PCR amplifications were carried out, one using oligonucleotides 7 (SEQ ID NO:7) and 8 (SEQ ID NO:8) as before, the other using two new oligonucleotides, 9 (SEQ ID NO:9) and 10 (SEQ ID NO:10), whose sequences are shown in FIG. 13F. As seen in FIG. 13A the product of PCR reaction 1 is a DNA segment containing the packaging signal flanked by AvrII and NheI sites and the product of PCR reaction 2 is a large DNA segment containing all of polyMRKCMVEGFP except the packaging signal in which the HCMV promoter has HindIII and AvrII sites 5' of the promoter and HindIII and NheI sites 3' of the ITR. At the next step, shown in FIG. 13B, the PCR1 product was cloned in pCR2.1-TOPO (Invitrogen Inc.) and the PCR2 product was digested with HindIII and ligated to generate pMRK Pkgng del with restriction sites as illustrated. As shown in FIG. 13C a HindIII-NheI fragment was cut out of pTOPO PCR1 and cloned into the HindIII-NheI site of pMRK Pkgng del. As can be seen from the diagrams in FIGS. 13B and 13C this ensured that the packaging signal was in the desired inverted orientation relative to its original configuration. Finally, extraneous sequences were removed by digestion with AvrII and religation (FIG. 13D) to create pMRKGFP Pkgng inv. The penultimate steps in this strategy then involved use of homologous recombination between a DNA fragment containing the left Ad ITR, inverted packaging signal and EGFP expression cassette with homologous sequences in an Ad5 genomic plasmid, pMRKAd5GFNR (S. Colloca, IRBM, unpublished) that had been linearized by cleavage with ClaI as shown in FIG. 13E, to generate pMRKGFPpkgng inv. This plasmid contains PacI sites adjacent to the left and right ITRs for liberation of the viral sequences from bacterial DNA sequences prior to transfection of E1 complementing host cells. Transfection was carried out by either use of Lipofectamine (Invitrogen) according to the vendor's recommendations, or using the Calcium Phosphate technique (Graham, F. L., van der Eb., A. J. A new technique for the assay of infectivity of human adenovirus 5 DNA. Virology 52, 456–467, 1973). In both cases viruses were obtained that expressed GFP as could be readily detected by fluorescence microscopy. For these experiments virus was rescued and initially grown in PERC6 cells that have no homology with the vector and in which no RCA should be produced, independently of whether the packaging signal is in its normal or inverted orientation.

One vector, designated AdMRKGFPpkgnginv, was expanded in PERC6 cells then used for serial passage experiments to test for emergence of RCA. The vector with inverted packaging signal was used to infect and serially passage in PERC6 cells, HER224 cells and 293 cells, and a parallel series of passages was carried out with a control vector, AdMRKEGFP, with packaging signal in the wild type orientation. It was expected that neither vector should produce RCA when passaged in PERC6 cells because of the lack of any homology to left or right of the E1 region. It was expected that passage of AdMRKEGFP in HER224 cells and 293 cells would result in emergence of RCA because of the presence of overlap homology on either side of E1. In the case of AdMRKGFPpkgninv grown in HER224 cells, although there are homologous sequences both to right and left of E1, the sequences to left of the E1 region (the packaging signal) are so oriented that, as detailed in the foregoing, recombination to left and to right of the expression cassette in E1 of the vector was predicted not to result in viable virus. In the case of the same vector grown in 293 cells there exists about 100 nt of homology (represented by the left ITR) that, according to the two-event theory advanced above (see discussion related to FIG. 5), might be sufficient to allow recombination and if such a recombination occurred along with a second recombination to the right of E1, the resulting RCA should be detectable after several passages in 293 cells. AdMRKEGFP was serially passaged in 293 cells and at various passages viral DNA was analyzed as in FIG. 11B or virus was used to infect A549 cells which are E1—and are permissive for RCA but not E1—Ad vectors. Surprisingly, no RCA were detectable following as many as 25 serial passages of the vector in 293 cells. Thus, the above results support that a lowering or elimination of RCA during recombinant adenoviral vector propagation is achieved in embodiments in which a segment of DNA comprising the packaging signal is in an inverted orientation along the DNA sequence of the adenoviral vector construct with respect to the nearest of a left ITR and a ITR of the vector. In some embodiments, this inverted segment includes all DNA sequences between the packaging signal, as it was originally oriented, and the point at which the E1 deletion begins (and, when present, as is typical, the inserted foreign DNA begins). This provides for greater probability of and extent of RCA reduction.

Further to this latter point, it is appreciated that the E1 deletion may be designed and implemented to leave in some nucleotides of the E1a and/or E1b genes, yet still provide for functional loss of the E1 region. In such situations there may be a number of intervening nucleotides between the 3' end of the packaging signal (in its original, non-inverted orientation) and the 5' starting point of where the particular E1 deletion begins. To the extent that these nucleotides remain in their original orientation when the packaging signal is being inverted, there is a theoretical increase in the likelihood of RCA production according to the two-event recombination theory discussed above. Thus, in various embodiments, to better assure reduced RCA production, the segment comprising the packaging signal that is being inverted may include less than 10, between 10 and 20, between 21 and 50, between 51 and 100, and between 100 and 200 nucleotides (base pairs).

As generally recognized in the art, the packaging signal itself needs to be within about 600 base pairs from the nearest ITR to function as a packaging signal (See Hearing et al., J. of Virology:61(8):2555–2558 (1987), and Susanne I. Schmid and Patrick Hearing, Cellular Components Interact with Adenovirus Type 5 Minimal Packaging Domains, J. of Virology, 72(8):6339–6347 (1998). Accordingly, in various embodiments of the present invention the inward-most end of the packaging signal (3' end if closest to the left ITR, and 5' end if closest to the right ITR) is within about 600 base pairs from the inward-most end of the closest ITR.

Further, in some embodiments of the present invention a length of non-inverted DNA sequence remains between the segment comprising the packaging signal in inverted orientation and the start of the DNA sequence comprising E1 deletion (i.e., the left end of the E1 deletion). Although this non-inverted DNA sequence may provide an opportunity for homologous recombination and consequent formation of RCA (assuming, per the two-event hypothesis that another recombination also occurs rightward of the E1 area), a relatively short sequence may nonetheless remain and the overall approach of the present invention, particularly inverting the major elements of the packaging signal with respect to the relevant terminal ITR, still provides for reduction or elimination of RCA.

Accordingly, some embodiments of the present invention are and/or utilize recombinant adenoviral nucleic acid sequences and vectors that comprise a non-inverted DNA sequence between the segment comprising the packaging signal in inverted orientation and the start of the DNA sequence comprising E1 deletion. In some embodiments, the length of this non-inverted DNA sequence is selected from the group of sequence length ranges consisting of: less than 10; between 10 and 20; between 21 and 50; and between 51 and 100 nucleotides (base pairs).

The present invention lends itself readily to the formulation of kits for use in generation of shuttle plasmids and for recombinant adenoviral vectors. Such kits comprise a carrier compartmentalized to receive in close confinement one or more containers. For example, kits suitable for generation of recombinant adenoviral vectors of the present invention are provided in a package comprising at least one component from each of the following groups, each suitably enclosed in a sealed container:

1. A shuttle plasmid, such as, not to be limiting pDCMH4LoxPkginv, pHCMVLacZPkginvlox, and pMRKGFPPkgnginv, and 2. An adenoviral genomic plasmid or vector, such as, not to be limiting pBHGlox E1,3Cre, pBHG10 (Microbix Biosystems), pBHGE3 (Microbix Biosystems), and pMRKAd5GFNR.

In some kits, a host cell also may be provided, such as, not to be limiting, 293 cells, HER224 cells, and 911 cells. Also, in some kits instructions are provided for preparation of the recombinant adenoviral vector by means of any of the methods provided above.

Among the shuttle plasmids of the present invention are those plasmids that are comprised both of a polycloning site and at least one integrase family type recombinase target site. Also, it is appreciated that the level of skill for production of shuttle plasmids, and for adenoviral vectors, is high, and many starting plasmids are commercially available. Consequently, a range of shuttle plasmids may be produced and have the features of the present invention, which include an origin of replication and an adenoviral DNA sequence comprising an inverted terminal repeat (ITR), a packaging signal in an inverted orientation with respect to the ITR, and a polycloning site.

Also, although "recombinant adenoviral vector" is defined to comprise an expression cassette, vector constructs of the present invention may include, instead of an expression cassette, a cloning site sequence such as a polycloning site, or an inserted coding region of a foreign DNA.

It should further be recognized that the examples above using the human adenovirus serotype 5 are not meant to be limiting. One skilled in the art would realize that similar plasmids, viruses and techniques could be utilized with a different human adenovirus serotype. An example, not meant to be limiting, of use of the present invention in a human adenovirus other than Ad5, follows.

EXAMPLE 7

The methods described above lend themselves readily to the production of kits useful for the construction of adenovirus vectors having inverted packaging signals. These kits include precursor plasmids that are commercially available. For example, not meant to be limiting, shuttle plasmids that are commercially available from Microbix Biosystems Inc. include the plasmids pDC311, pDC312, pDC315, pDC316 that are part of Kit D, pDC411, 412, 415 and 416 that are part of kit F, and pDC511, 512, 515 and 516 that are part of kit E, pDC315(io), pDC316(io) that are part of kit H, and pDC515(io) and 516(io) that are part of kit J. These plasmids may be used for rescue of Ad vectors by Cre mediated or FLP mediated recombination, and are readily converted to shuttle plasmids comprising an inverted packaging signal such as by a method as illustrated in FIG. 14. The resulting shuttle plasmids having an inverted packaging signal are then used according to methods known in the art, including specifically those taught in U.S. Pat. No. 6,379,943 B1, U.S. Pat. No. 6,140,087, U.S. patent application Ser. No. 09/978,464, and U.S. patent application Ser. No. 09/981,648, all of which are hereby incorporated by reference specifically for the recombination methods taught therein.

For example, as illustrated in FIG. 14A, pDCMH4LoxPkginv is digested with MluI and the MluI digested DNA is treated with the Klenow fragment of DNA polymerase to create a blunt end. The DNA is then digested with PvuI and the PvuI-MluI fragment is purified and inserted into PvuI and XbaI digested pDC311 wherein the XbaI site is similarly treated with the Klenow fragment of DNA polymerase. The resulting plasmid, pDC311inv, has an inverted packaging signal which will be rescued into recombinant adenovirus vectors when the shuttle plasmid is cotransfected into host cells with plasmids such as pBHGlox E1,3Cre.

The same process allows for modification of pDC312 of Kit D, and the above mentioned plasmids pDC411, 412, 511, and 512. FIG. 14B illustrates a similarly straightforward method for modification of the series of shuttle plasmids containing the MCMV promoter. In this case the PvuI-PacI fragment of pDCMH4LoxPkginv is substituted for the PvuI-PacI fragment of pDC315 to generate pDC315inv. The same simple process can be used to generate all other shuttle plasmids of Microbix Biosystems' kits D-J that contain the MCMV promoter.

The plasmids of kit F, namely pDC411, 412, 415 and 416, once converted to shuttle plasmids with inverted packaging signals as described above, can be used to generate recombinant viral vectors based on additional serotypes by means of homologous recombination as taught in U.S. Pat. No. 6,730,507. For example, not meant to be limiting, FIG. 15 illustrates a method for construction of Ad1 or Ad6 recombinant vectors with inverted packaging signals. In the example shown, pDC415inv having an inverted packaging signal (constructed by the methods outlined above) is cotransfected into 293 cells with ClaI digested Ad1 or Ad6 DNA. Homologous recombination between overlapping homologous viral sequences in pDC415inv and the left end of the large fragment of ClaI digested Ad1 or Ad6 DNA results in the desired vectors. It is apparent that any of the plasmids pDC411, 412, 415 or 416 or their derivatives with inverted packaging signals could be used in the cotransfection illustrated in FIG. 15, as could derivative plasmids having any of a variety of insertions of coding sequences or expression cassettes.

The above methods are not limited to adenovirus serotypes having close homology to Ad5. For example, not meant to be limiting, complementing E1 positive host cells for propagation of E1 deleted Ad12 viruses are available (HEKMH12 cells mentioned in Shaw, G., Morse, S., Ararat, M. and Graham, F. L. Preferential transformation of human neuronal cells by human adenoviruses and the origins of HEK 293 cells. FASEB J., 16: 869_871, 2002.); the entire Ad12 genome has been sequenced (GenBank Accession No. X73487) and the left end of Ad12 DNA has been cloned into bacterial plasmids (Kawarabayasi Y, Sugisaki H. Structure of viral DNA in a rat cell line transformed by the cloned EcoRI-C fragment of adenovirus 12. Nucleic Acids Res. 13: 6591–65604, 1985). Thus the left end of the Ad12 genome can be readily manipulated by the methods taught herein to generate a plasmid carrying Ad12 DNA comprising an inverted packaging signal and a deletion of E1 and further comprising insertions of foreign DNA including expression cassettes. Infectious recombinant Ad12 vectors can be obtained using methods similar to those described in FIG. 15 making use of a unique BstEII site near the left end of the Ad12 genome. Vectors can be rescued by homologous recombination as in FIG. 15 or BstEII digested plasmid DNA can be directly ligated to the large fragment of BstEII digested Ad12 DNA according to the method of Stow (Stow, N. D. Cloning of a DNA fragment from the left-hand terminus of the adenovirus type 2 genome and its use in site-directed mutagenesis. *J. Virol.* 37, 171–180, 1981). Alternatively homologous recombination in bacteria can be employed to construct recombinant Ad12 vector genomes.

EXAMPLE 8

This example and related discussion pertains to use of the present invention in human adenoviruse0s other than those described in the above examples, and in non-human adenoviruses. All or almost all Adenovirus genomes contain a packaging signal near the left end of the DNA, typically located between the 3' end of the left ITR and a few hundred bp of the left end, that results in polar packaging of the viral DNA into virions, starting from the left end of the genome. The actual size and sequence of the packaging signal can vary from one adenovirus to another but the location and functional properties of the packaging signal seem to be relatively highly conserved. For example in the case of Ad5 (and Ad2 which is nearly identical in sequence to Ad5 at the left end) the packaging signal is localized within a segment from approximately nt 200 to approximately nt 380 from the left end (see Hearing et al., Jl. of Virology:61, 2555–2558 (1987) and Grable and Hearing 1992, J. Virol. 64: 2047–2056 and references cited therein.). Furthermore in adenoviruses as diverse as porcine adenovirus (PAV), bovine adenovirus (BAV) and canine adenovirus (CAV) cis-acting sequences are found at the left end of the genome, between nt 212 and 319 for PAV-3 (Xing, L. and Tikkoo, S. K. Characterization of cis-acting sequences involved in packaging porcine adenovirus type 3. Virology 314: 650–661, 2003); between nt 224 and 540 for BAV-3 (Xing, L., Zhang, L., Van Kessel, J. and Tikkoo, S. K. Identification of cis-acting sequences required for selective packaging of bovine adenovirus type 3. J. Gen. Virol. 84: 2947–2956, 2003) and between nt 200 and 400 for CAV-2 (Soudais, C., Boutin, S. and Kremer, E. J. Characterization of cis-Acting Sequences Involved in Canine Adenovirus Packaging, Mol. Therapy, 3(4)631–640).

All of the above xenogenic (non-human) adenoviruses as well as additional ones have been developed as vectors as discussed in Chapter 16 of Adenoviral Vectors for Gene Therapy, David T. Curiel and Joanne T. Douglas, Academic Press, 2002, which is incorporated in its entirety. Like a number of human adenoviruses numerous xenogenic adenovirus genomes have been sequenced in their entirety, e.g. Canine adenovirus CAV2 (GenBank Accession No. U77082, incorporated by reference), Porcine adenovirus 3 (PAV3) GenBank Accession No. AF083132), Porcine adenovirus 5 (PAV5) (GenBank Accession No. AF289262), Bovine adenoviruses 3 and 4 (Accession Nos. BK000401 and NC002685 respectively) and Ovine adenovirus 7 (NC004037) and others. Furthermore, plasmid clones containing all or part of the viral genomes are available and in many cases E1 complementing cell lines are available. For example see Reddy P S, Idamakanti N, Chen Y, Whale T, Babiuk L A, Mehtali M, Tikoo S K. Replication-defective bovine adenovirus type 3 as an expression vector. J Virol. November 1999;73(11):9137–44., Kremer E J, Boutin S, Chillon M, Danos O. Canine adenovirus vectors: an alternative for adenovirus-mediated gene transfer. J Virol. January 2000; 74(1):505–12.

In addition, numerous simian adenovirus genomes have been fully sequenced, plasmid clones have been derived, and vector systems developed. In many cases simian adenovirus vectors with deletions of E1 can be propagated in 293 cells, for example see Farina S F, Gao G P, Xiang Z Q, Rux J J, Burnett R M, Alvira M R, Marsh J, Ertl H C, Wilson J M. Replication-defective vector based on a chimpanzee adenovirus. J Virol. December 2001; 75(23):11603–13.

These systems also can be readily modified according to the methods taught herein to generate vectors with inverted packaging signals for purposes of reducing the contamination levels of RCA in vector stocks. Although there may be some human and some xenogenic adenoviruses for which the general rule that the packaging signal resides within a well defined region at the left end of the genome does not hold, nonetheless, for a sufficient number of adenoviruses the present teachings are expected to provide for successful production of desired recombinant adenoviral vectors without undue experimentation. Similarly for xenogenic adenovirus vectors the art is sufficiently advanced and the systems sufficiently similar to those developed for Ad5 and Ad2 that the methods described in detail herein for Ad5 vectors for the inversion of the packaging signal of said vectors can readily be applied to the inversion of the packaging signal in additional human or xenogenic vectors.

It is appreciated that the locus and key components of the packaging signals are not known for all non-human adenoviruses. However, it is appreciated that the teachings of the present invention provide for a number of approaches to practicing the invention upon or after determination of the packaging signal region for any nonhuman species. Also, based on the teachings herein, knowledge of the precise packaging signal region is not required to practice the invention, since additional DNA sequences adjacent to the packaging signal also may be inverted with respect to the nearest ITR.

With regard to one example of such modification, it has been reported that sequences homologous to the nt 193–273 section of the Ad5 packaging signal are found in Ad7 and Ad12 (Hearing et al., Jl. of Virology; 61:2555–2558 (1987)). Using appropriate techniques such as those described above, a segment of Ad12 comprising this homologous packaging signal is inverted with respect to the left ITR of Ad12. Also using appropriate techniques such as those described above, the Ad12 E1 sequence is deleted, and an expression cassette comprising a foreign DNA gene of interest is inserted into the E1 region. Upon serial passaging to increase vector quantity, the desired recombinant adenoviral vector is propagated without detectable presence of RCA.

With regard to a second example of such modification, canine adenovirus CaDV2 (GenBank Accession No. U77082, incorporated by reference) comprises a packaging signal that includes an approximately 200 base pair sequence between the left ITR (which is about 198 nt) and the start of the E1 coding region (at about 500 nt) (See Chapter 16 of Adenoviral Vectors for Gene Therapy, and Claire Soudais, Sylvie Boutin, and Eric J. Kremer, Characterization of cis-Acting Sequences Involved in Canine Adenovirus Packaging, Mol. Therapy, 3(4)631–640). Using appropriate techniques such as those described above (and using DKCre, an appropriate canine cell culture), a segment of CaDV2 comprising this packaging signal is inverted with respect to the left ITR of CaDV2. Also using appropriate techniques such as those described above, the CaDV2 E1 sequence is deleted, and an expression cassette comprising a foreign DNA gene of interest is inserted into the E1 region. Upon serial passaging to increase vector quantity, the desired recombinant adenoviral vector is propagated in suitable canine adenovirus propagating culture cells without detectable presence of RCA.

It is appreciated that the exact locus and key components of the packaging signals for the majority of nonhuman adenoviruses is not known. However, it is appreciated that the teachings of the present invention provide for a number of approaches to practicing the invention upon or after determination of the packaging signal region for any nonhuman species. Also, based on the teachings herein, knowledge of the precise packaging signal region is not required to practice the invention, since additional DNA sequences adjacent to the packaging signal also may be inverted with respect to the nearest ITR.

Also, it is noted that a recombinant adenoviral vector comprising an inverted packaging signal may be produced and propagated using various methods as described above (and, where needed, in combination with what is known to those skilled in the art) wherein an expression cassette (typically comprising foreign DNA) is inserted into E3 but not into E1, and wherein in such vector a deletion in E1 has eliminated expression of E1A and E1B genes. For example, not meant to be limiting, U.S. Pat. No. 6,140,087 and Bett, A. J., Haddara, W., Prevec, L. and Graham, F. L. An efficient and flexible system for construction of adenovirus vectors with insertions or deletions in early regions 1 and 3. Proc. Natl. Acad. Sci. US 91: 8802–8806, 1994 teach methods for insertion of foreign DNA into the E3 region of a genomic plasmid that can then be used in homologous recombination with shuttle plasmids such as pDC411inv or pDC412inv to create a virus having an E1 deletion and insertion of said foreign DNA in E3.

While a number of embodiments of the present invention have been shown and described herein in the present context, such embodiments are provided by way of example only, and not of limitation. Numerous variations, changes and substitutions will occur to those of skilled in the art without departing from the invention herein. For example, the present invention need not be limited to best mode disclosed herein, since other applications can equally benefit from the teachings of the present invention. Accordingly, it is intended that the invention be limited only by the spirit and scope of the appended claims in accordance with relevant law as to their interpretation.

I claim as my invention:

1. A recombinant adenoviral nucleic acid sequence comprising an adonoviral vector comprising: a segment of DNA comprising an adenoviral packaging signal, the segment providing the packaging signal in an inverted orientation with respect to the nearest of a left adenoviral ITR and a right adenoviral ITR of the vector; a deletion in early region 1 (E1); and an insertion of foreign DNA in E1, wherein the packaging signal is functional and wherein the insertion of foreign DNA in E1 comprises an expression cassette.

2. The recombinant adenoviral nucleic acid sequence according to claim 1, wherein the packaging signal is positioned within about 600 nucleotides from the left adenoviral ITR.

3. The recombinant adenoviral nucleic acid sequence of claim 1, wherein the packaging signal is positioned within about 600 nucleotides from the right adenoviral ITR.

4. The recombinant adenoviral nucleic acid sequence of claim 1, wherein the insertion of foreign DNA comprises a cloning site comprising at least one site, each of said at least one site is selected from the group consisting of an endonuclease site and an integrase family recombinase target site.

5. A recombinant adenoviral nucleic acid sequence comprising an adenoviral vector comprising:
   a. a left-end adenoviral inverted terminal repeat (ITR) sequence;
   b. an adenoviral packaging signal inverted with respect to its normal orientation in relation to the nearest of the left-end adenoviral ITR and a right-end adenoviral inverted terminal repeat (ITR) sequence;
   c. a deletion in early region 1 (E1) to eliminate expression of E1A and E1B genes;
   d. an insertion of foreign DNA in E1, or in both E1 and E3, wherein foreign DNA inserted into E1, or each of the foreign DNA insertions in E1 and E3, comprises an expression cassette; and
   e. the right-end adenoviral inverted terminal repeat (ITR) sequence.

6. A recombinant adenoviral vector comprising an adenoviral packaging signal in an inverted orientation with respect to the nearest of a right and a left adenoviral inverted terminal repeat (ITR) sequence, and further comprising an insertion into early region 1 (E1) of foreign DNA comprising an expression cassette comprising an introduced DNA sequence, a promoter operatively linked to the introduced DNA sequence, and a termination sequence.

7. The recombinant adenoviral vector of claim 6, additionally comprising an insertion of foreign DNA in early region 3 (E3).

8. The recombinant adenoviral vector of claim 6 wherein the inverted packaging signal is disposed at the right end of the adenovirus DNA sequence adjacent to the right adenoviral ITR.

9. A system for propagation of a recombinant adenoviral vector comprising
   a. a culture vessel comprising culture media into which are added:
   b. a recombinant adenoviral vector comprising a nucleic acid sequence comprising:
      i. a left-end adenoviral inverted terminal repeat (ITR) sequence;
      ii. a deletion in early region 1 (E1) to eliminate expression of E1A and E1B genes;
      iii. an insertion of an expression cassette in E1, or in both E1 and E3;
      iv. an adenoviral packaging signal inverted with respect to a normal orientation in relation to the nearest of the left-end adenoviral ITR and a right-end adenoviral inverted terminal repeat (ITR) sequence; and
      v. the right-end adenoviral inverted terminal repeat (ITR) sequence, and
   c. a cell comprising an adenoviral DNA sequence expressing E1A and E1B genes.

10. The system of claim 9, the adenoviral DNA sequence of the cell lacking a left adenoviral ITR.

11. A method for producing a recombinant adenoviral vector comprising a gene of interest, said method not producing a vector having a functional E1 region, said method comprising:
   a. providing a complementing cell harboring a first nucleic acid comprising adenoviral nucleic acid sequences encoding functional E1A protein and functional E1B protein;
   b. transferring a second nucleic acid into said complementing cell, said second nucleic acid comprising a recombinant adenoviral nucleic acid sequence comprising functional adenoviral Inverted Terminal Repeats (ITRs) at or near both of its termini, and a functional adenoviral packaging signal inverted with respect to a normal orientation along the adenoviral DNA sequence with respect to the nearest of the adenoviral ITRs, the second nucleic acid further compirising a foreign DNA sequence in early region 1 (E1) comprising the gene of interest, and all sequences required for replication of said second nucleic acid which are not provided by said complementing cell;
   c. culturing said complementing cell; and
   d. harvesting the recombinant adenoviral vector produced from the complementing cell.

12. The method of claim 11, wherein the first nucleic acid lacks a left adenoviral ITR.

\* \* \* \* \*